US009382424B2

(12) United States Patent
Rachwal et al.

(10) Patent No.: US 9,382,424 B2
(45) Date of Patent: *Jul. 5, 2016

(54) HIGHLY-FLUORESCENT AND PHOTO-STABLE CHROMOPHORES FOR ENHANCED SOLAR HARVESTING EFFICIENCY

(71) Applicant: Nitto Denko Corporation, Ibaraki, Osaka (JP)

(72) Inventors: Stanislaw Rachwal, Oceanside, CA (US); Peng Wang, San Diego, CA (US); Bogumila Rachwal, Oceanside, CA (US); Hongxi Zhang, Temecula, CA (US); Michiharu Yamamoto, Carlsbad, CA (US)

(73) Assignee: Nitto Denko Corporation, Osaka (JP)

( * ) Notice: Subject to any disclaimer, the term of this patent is extended or adjusted under 35 U.S.C. 154(b) by 217 days.

This patent is subject to a terminal disclaimer.

(21) Appl. No.: 13/626,679

(22) Filed: Sep. 25, 2012

(65) Prior Publication Data

US 2013/0074927 A1  Mar. 28, 2013

Related U.S. Application Data

(60) Provisional application No. 61/539,392, filed on Sep. 26, 2011, provisional application No. 61/567,534, filed on Dec. 6, 2011, provisional application No. 61/662,825, filed on Jun. 21, 2012, provisional application No. 61/662,835, filed on Jun. 21, 2012.

(51) Int. Cl.
| | |
|---|---|
| C07D 249/18 | (2006.01) |
| C09B 11/02 | (2006.01) |
| C09B 57/00 | (2006.01) |
| H01L 31/055 | (2014.01) |
| H01L 51/00 | (2006.01) |

(52) U.S. Cl.
CPC ............... C09B 11/02 (2013.01); C09B 57/00 (2013.01); C09B 57/001 (2013.01); H01L 31/055 (2013.01); C07D 249/18 (2013.01); H01L 51/0071 (2013.01); Y02E 10/52 (2013.01)

(58) Field of Classification Search
CPC .. C07D 249/18; C07D 249/20; C07D 231/12; C07D 249/24; C08K 5/3475
USPC ........................................... 548/257; 428/690
See application file for complete search history.

(56) References Cited

U.S. PATENT DOCUMENTS

| | | |
|---|---|---|
| 3,239,406 A | 3/1966 | Coffman et al. |
| 3,915,979 A | 10/1975 | Chow et al. |
| 4,162,928 A | 7/1979 | Shepard, Jr. |
| 4,262,851 A | 4/1981 | Graser et al. |
| 4,297,490 A | 10/1981 | Neumann |
| 4,379,934 A | 4/1983 | Graser et al. |
| 4,419,427 A | 12/1983 | Graser et al. |
| 4,431,808 A | 2/1984 | Protiva et al. |
| 4,446,324 A | 5/1984 | Graser |
| 4,450,273 A | 5/1984 | Graser |
| 4,501,906 A | 2/1985 | Spietschka et al. |
| 4,594,420 A | 6/1986 | Spietschka et al. |
| 4,618,694 A | 10/1986 | Iden et al. |
| 4,667,036 A | 5/1987 | Iden et al. |
| 4,709,029 A | 11/1987 | Spietschka et al. |
| 4,725,690 A | 2/1988 | Graser |
| 4,746,741 A | 5/1988 | Staudenmayer et al. |
| 4,831,140 A | 5/1989 | Spietschka et al. |
| 4,845,223 A | 7/1989 | Seybold et al. |
| 4,968,571 A | 11/1990 | Gruenbaum et al. |
| 5,019,473 A | 5/1991 | Nguyen et al. |
| 5,028,504 A | 7/1991 | Rule et al. |
| 5,077,161 A | 12/1991 | Law |
| 5,123,966 A | 6/1992 | Dietz et al. |
| 5,141,837 A | 8/1992 | Nguyen et al. |
| 5,154,770 A | 10/1992 | Spietschka et al. |
| 5,248,774 A | 9/1993 | Dietz et al. |
| 5,264,034 A | 11/1993 | Dietz et al. |
| 5,466,807 A | 11/1995 | Dietz et al. |
| 5,472,494 A | 12/1995 | Hetzenegger et al. |
| 5,645,965 A | 7/1997 | Duff et al. |
| 5,693,808 A | 12/1997 | Langhals |

(Continued)

FOREIGN PATENT DOCUMENTS

| | | |
|---|---|---|
| CN | 1 473 187 | 2/2004 |
| CN | 1 671 675 | 9/2005 |

(Continued)

OTHER PUBLICATIONS

Baran, Derya, Abidin Balan, Beatriz-Meana Esteban, Helmut Neugebauer, Niyazi Serdar Sariciftci, Levent Toppare, "Spectroelectrochemical and Photovoltaic Characterization of a Solution-Processable n-andp Type Dopable Pyrrole-Bearing Conjugated Polymer.", Macromolecular Chemistry and Physics 2010, 211, 2602-2610.*

(Continued)

Primary Examiner — Alicia L Otton
Assistant Examiner — Sagar Patel
(74) Attorney, Agent, or Firm — Vedder Price P.C.

(57) ABSTRACT

The invention provides highly fluorescent materials comprising a single (n=0) or a series (n=1, 2, etc.) of benzo heterocyclic systems. The photo-stable highly luminescent chromophores are useful in various applications, including in wavelength conversion films. Wavelength conversion films have the potential to significantly enhance the solar harvesting efficiency of photovoltaic or solar cell devices.

15 Claims, 1 Drawing Sheet

(56) References Cited

U.S. PATENT DOCUMENTS

| | | | |
|---|---|---|---|
| 5,710,197 A | 1/1998 | Fischer et al. | |
| 5,808,073 A | 9/1998 | Böhm et al. | |
| 5,816,238 A | 10/1998 | Burns et al. | |
| 5,874,580 A | 2/1999 | Hao et al. | |
| 5,981,773 A | 11/1999 | Langhals et al. | |
| 6,063,181 A | 5/2000 | Böhm et al. | |
| 6,130,217 A | 10/2000 | Arnold et al. | |
| 6,136,976 A | 10/2000 | Böehm et al. | |
| 6,139,210 A | 10/2000 | Nelson et al. | |
| 6,166,210 A | 12/2000 | Langhals et al. | |
| 6,184,378 B1 | 2/2001 | Böhm et al. | |
| 6,326,494 B1 | 12/2001 | Böhm et al. | |
| 6,572,977 B1 | 6/2003 | Pavelka et al. | |
| 6,654,161 B2 | 11/2003 | Bass et al. | |
| 6,806,368 B2 | 10/2004 | Würthner et al. | |
| 6,924,427 B2 | 8/2005 | Eckert et al. | |
| 6,986,811 B2 | 1/2006 | Könemann et al. | |
| 7,714,099 B2 | 5/2010 | Morishita et al. | |
| 7,791,157 B2 | 9/2010 | Cho et al. | |
| 7,867,601 B2 | 1/2011 | Ikishima et al. | |
| 7,887,914 B2 | 2/2011 | Kobayashi et al. | |
| 7,943,845 B2 | 5/2011 | Hayes | |
| 8,158,450 B1 | 4/2012 | Sheats et al. | |
| 2004/0092246 A1 | 5/2004 | Cai et al. | |
| 2004/0115473 A1 | 6/2004 | Burroughes et al. | |
| 2005/0271566 A1 | 12/2005 | Yadav | |
| 2006/0041221 A1 | 2/2006 | Stypulkowski | |
| 2006/0052612 A1 | 3/2006 | Stossel et al. | |
| 2006/0083945 A1* | 4/2006 | Morishita et al. | 428/690 |
| 2007/0003783 A1 | 1/2007 | Morishita et al. | |
| 2007/0073052 A1 | 3/2007 | Velusamy et al. | |
| 2008/0087878 A1 | 4/2008 | Koenemann et al. | |
| 2008/0114170 A1 | 5/2008 | Konemann et al. | |
| 2008/0149165 A1 | 6/2008 | Hoeks et al. | |
| 2008/0167345 A1 | 7/2008 | Jones et al. | |
| 2008/0236667 A1 | 10/2008 | Naum et al. | |
| 2008/0245411 A1 | 10/2008 | Hammermann et al. | |
| 2008/0289681 A1 | 11/2008 | Adriani et al. | |
| 2009/0124625 A1 | 5/2009 | Bessis et al. | |
| 2009/0151785 A1 | 6/2009 | Naum et al. | |
| 2009/0275619 A1 | 11/2009 | Boueres et al. | |
| 2010/0012183 A1 | 1/2010 | Yeh | |
| 2010/0043875 A1 | 2/2010 | Bhaumik et al. | |
| 2010/0139769 A1 | 6/2010 | Mapel | |
| 2010/0154862 A1 | 6/2010 | Schiavoni et al. | |
| 2010/0186801 A1 | 7/2010 | Boehm et al. | |
| 2010/0224248 A1 | 9/2010 | Kenney et al. | |
| 2010/0249367 A1 | 9/2010 | Toppare et al. | |
| 2010/0278480 A1 | 11/2010 | Vasylyev | |
| 2010/0294339 A1 | 11/2010 | Hollars | |
| 2011/0011455 A1 | 1/2011 | Ji et al. | |
| 2011/0204292 A1 | 8/2011 | Imamura | |
| 2011/0253197 A1 | 10/2011 | Mapel et al. | |
| 2012/0222723 A1 | 9/2012 | Mayer et al. | |
| 2012/0227809 A1 | 9/2012 | Bharti et al. | |
| 2013/0074927 A1 | 3/2013 | Rachwal et al. | |
| 2013/0089946 A1* | 4/2013 | Zhang et al. | 438/86 |
| 2013/0139868 A1 | 6/2013 | Zhang et al. | |
| 2013/0284265 A1 | 10/2013 | Jiang et al. | |
| 2014/0083482 A1 | 3/2014 | Hebrink | |
| 2014/0311566 A1* | 10/2014 | Zhang et al. | 136/257 |
| 2015/0041042 A1 | 2/2015 | Zhang et al. | |
| 2015/0041052 A1 | 2/2015 | Zhang et al. | |

FOREIGN PATENT DOCUMENTS

| | | |
|---|---|---|
| CN | 101 148 495 | 3/2008 |
| CN | 101 289 447 | 10/2008 |
| CN | 101 343 352 | 1/2009 |
| CN | 101 671 428 | 3/2010 |
| CN | 101 768 138 | 7/2010 |
| CN | 101 775 123 | 7/2010 |
| CN | 101 935 389 | 1/2011 |
| CN | 102 464 794 | 5/2012 |
| DE | 28 51 513 | 6/1980 |
| DE | 34 00 991 | 7/1985 |
| DE | 10 2005 062 687 | 7/2007 |
| EP | 0284686 A1 | 2/1987 |
| EP | 0 692 517 | 1/1996 |
| EP | 2 080 785 | 7/2009 |
| EP | 2 194 106 | 6/2010 |
| EP | 2 261 300 | 12/2010 |
| EP | 2 333 017 | 6/2011 |
| EP | 2 354 204 | 8/2011 |
| EP | 2 355 162 | 8/2011 |
| EP | 2 557 137 | 2/2013 |
| EP | 2 557 606 | 2/2013 |
| EP | 2 578 075 | 4/2013 |
| FR | 2146136 | 2/1973 |
| JP | 44-008884 | 4/1969 |
| JP | 50-159483 | 12/1975 |
| JP | 53-90260 | 8/1978 |
| JP | 1-135776 | 5/1989 |
| JP | 11-220147 | 8/1999 |
| JP | 2001-000410 | 1/2001 |
| JP | 2001-094129 | 4/2001 |
| JP | 2005-258388 | 9/2005 |
| JP | 2006077171 A * | 3/2006 |
| JP | 2008-502674 | 1/2008 |
| JP | 2008-516008 | 5/2008 |
| JP | 2009-532452 | 9/2009 |
| JP | 2010-283282 | 12/2010 |
| JP | 2011-151094 | 8/2011 |
| JP | 2012-077116 | 4/2012 |
| WO | WO 02/22761 | 3/2002 |
| WO | WO 2004/092246 | 10/2004 |
| WO | WO 2005/054212 | 6/2005 |
| WO | WO 2006/041221 | 4/2006 |
| WO | WO 2006/088369 | 8/2006 |
| WO | WO 2008/110567 | 9/2008 |
| WO | WO 2009/011791 | 1/2009 |
| WO | WO 2009/115574 | 9/2009 |
| WO | WO 2010/046114 | 4/2010 |
| WO | 2010084067 A2 | 7/2010 |
| WO | WO 2010/114497 | 10/2010 |
| WO | WO 2010/118920 | 10/2010 |
| WO | WO 2011/068305 | 6/2011 |
| WO | WO 2011/072876 | 6/2011 |
| WO | 2011073316 A1 | 7/2011 |
| WO | WO 2012/024070 | 2/2012 |
| WO | WO 2012/043401 | 4/2012 |
| WO | WO 2012/068703 | 5/2012 |
| WO | WO 2012/094409 | 7/2012 |
| WO | WO 2012/134992 | 10/2012 |
| WO | WO 2013/049062 | 4/2013 |
| WO | WO 2013/052381 | 4/2013 |
| WO | WO 2013/067288 | 5/2013 |
| WO | WO 2013/085607 | 6/2013 |
| WO | WO 2013/116559 | 8/2013 |
| WO | WO 2013/116569 | 8/2013 |
| WO | 2013128465 A1 | 9/2013 |
| WO | WO 2014/160707 | 10/2014 |
| WO | WO 2014/197393 | 12/2014 |

OTHER PUBLICATIONS

Peng, B., A. Najari, B. Liu, P. Berrouard, D. Gendron, Y. He, K. Zhou, M. Leclerc and Y. Zou "A New Dithienylbenzotriazole-Based Poly(2,7-carbazole) for Efficient Photovoltaics", Macromolecular Chemistry and Physics 2010, 211, pp. 2026-2033.*

Pasker, F., S. M. Le Blanc, G. Schnakenburg, and S. Hoger "Thiophen-2-aryl-2H-benzotriazole-thiophene Oligomers with Adjustable Electronic Properties", Organic Letters, American Chemical Society 2011, 13 (9), pp. 2338-2341.*

Tanimoto, A., and T. Yamamota "Synthesis of n-Type Poly(benzotriazole)s having p-Conducting and Polymerizable Carbazole Pendants" Macromolecules 2006, 39: pp. 3546-3552.*

Akbaş o Ğ lu et al., "Electrochemical and Optical Studies of Furan and Thieno[3,2-B]Thiophene End Capped Benzotriazole Derivatives," Journal of Polymer Science Part A: Polymer Chemistry, Dec. 1, 2010, vol. 48, No. 23, pp. 5603-5610.

(56) References Cited

OTHER PUBLICATIONS

Balan et al., "Donor-Acceptor Polymer with Benzotriazole Moiety: Enhancing the Electrochromic Properties of the 'Donor Unit,'" Chemistry of Materials, 2008, vol. 20, No. 24, pp. 7510-7513.

Balan et al., "One Polymer for All: Benzotriazole Containing Donor-Acceptor Type Polymer as a Multi-Purpose Material", Chemical Communications, 2009, vol. 44, pp. 6768-6770.

Baran et al., "Processable Multipurpose Conjugated Polymer for Electrochromic and Photovoltaic Applications", Chemistry of Materials, 2010, vol. 22, pp. 2978-2987.

Baran et al., "Spectroelectrochemical and Photovoltaic Characterization of a Solution-Processable n-and-p Type Dopable Pyrrole-Bearing Conjugated Polymer", Macromolecular Chemistry and Physics, 2010, vol. 211, No. 24, pp. 2602-2610.

Celebi et al., "Enhancing Electrochromic and Kinetic Properties of poly(2,3-bis(4-tert-butylphenyl)-5,8-di(1H-pyrrol-2-yl) quinoxaline) by Copolymerizatio", Electrochimica Acta, Feb. 28, 2010, vol. 55, No. 7, pp. 2373-2376.

Ç etin et al., "A New p- and n-Dopable Selenophene Derivative and its Electrochromic Properties", Organic Electronics, Feb. 2009, vol. 10, No. 1, pp. 34-41.

Cui et al., "Incorporating Benzotriazole Moiety to Construct D-A-Π-A Organic Sensitizers for Solar Cells: Significant Enhancement of Open-Circuit Photovoltage with Long Alkyl Group", Chemistry of Materials, 2011, vol. 23, No. 19, pp. 4394-4401.

Içlu et al., "Donor-Acceptor Polymer Electrochromes with Tunable Colors and Performance," Chemistry of Materials, 2010, vol. 22, No. 13, pp. 4034-4044.

Kaya et al., "Solution Processable Benzotriazole and Fluorene Containing Copolymers for Photovoltaic Applications", Solar Energy Materials and Solar Cells, Apr. 2012, vol. 99, pp. 321-326.

Klampaftis et al., "Enhancing the Performance of Solar Cells via Luminescent Down-Shifing of the Incident Spectrum: A Review", Materials and Solar Cells, 2009, vol. 93, pp. 1182-1194.

Liu et al., "Synthesis and Electroluminescent Properties of a Phenothiazine-Based Polymer for Nondoped Polymer Light-Emitting Diodes with a Stable Orange-Red Emission," Journal of Polymer Science Part A: Polymer Chemistry, Nov. 1, 2007, vol. 45, No. 21, pp. 4867-4878.

Liu et al., "Synthesis and Photovoltaic Properties of a Solution-Processable Organic Molecule Containing Dithienylbenzotriazole and Triphenylamine," Synthetic Metals, May 2012, vol. 162, No. 7-8, pp. 630-635.

Mao et al., "Benzotriazole-Bridged Sensitizers Containing a Furan Moiety for Dye-Sensitized Solar Cells with High Open-Circuit Voltage Performance," Chemistry Asian Journal, 2012, pp. 982-991.

Maruyama et al., "Transformations of the Wavelength of the Light Incident Upon Solar Cells", Solar Energy Materials and Solar Cells, 2001, vol. 69, pp. 207.

Pasker et al., "Thiophene-2-aryl-2H-benzotriazole-thiophene Oligomers with Adjustable Electronic Properties," Organic Letters, 2011, vol. 13, No. 9, pp. 2338-2341.

Peng et al., "A New Dithienylbenzotriazole-Based Poly(2,7-carbazole) for Efficient Photovoltaics", Macromolecular Chemistry and Physics, 2010, vol. 211, No. 18, pp. 2026-2033.

Price et al., "Fluorine Substituted Conjugated Polymer of Medium Band Gap Yields 7% Efficiency in Polymer-Fullerene Solar Cells", Journal of the American Chemical Society, 2011, vol. 133, No. 12, pp. 4625-4631.

Richards et al., "Overcoming the Poor Short Wavelength Spectral Response of CdS/CdTe Photovoltaic Modules via Luminescence Down-Shifting: Ray-Tracing Simulations", Progress in Photovoltaics: Research and Applications, 2007, vol. 15, pp. 27-34.

Zhang et al., "Bulk-Heterojunction Solar Cells with Benzotriazole-Based Copolymers as Electron Donors: Largely Improved Photovoltaic Parameters by Using PFN/A1 Bilayer Cathode", Macromolecules, 2010, vol. 43, pp. 9771-9778.

Zhu et al., "Organic D-A-Π-A Solar Cell Sensitizers with Improved Stability and Spectral Response", Advanced Functional Materials, 2011, vol. 21, pp. 756-763.

Invitiation to Pay Additional Fees in PCT Application No. PCT/US2012/057118, dated Feb. 4, 2013.

International Search Report and Written Opinion in PCT Application No. PCT/US2012/057118, dated Apr. 22, 2013.

Bulut et al., "Benzotriazole Derivatives as Long Wavelength Photosensitizers for Diaryliodonium Salt Initiators", Journal of Polymer Science Part A: Polymer Chemistry, 2010, vol. 49, No. 3, pp. 729-733.

Ekiz et al., "Electrochemical Polymerization of (2-Dodecyl-4, 7-di(thiophen-2-yl)-2H-benzo[d][1,2,3] triazole): A Novel Matrix for Biomolecule Immobilization," Macromolecular Bioscience, Dec. 8, 2010, vol. 10, No. 12, pp. 1557-1565.

Falzon et al., "Designing Acceptor Polymers for Organic Photovoltaic Devices", The Journal of Physical Chemistry, 2011, vol. 115, No. 7, pp. 3178-3187.

Hizalan et al., "Spray Processable Ambipolar Benzotriazole Bearing Electrochromic Polymers with Multi-Colored and Transmissive States," Journal of Materials Chemistry, 2011, vol. 21, No. 6, pp. 1804-1809.

Hu et al., "Theoretical Investigation on the White-Light Emission from a Single-Polymer System with Simultaneous Blue and Orange Emission," Polymer, Nov. 2009, vol. 50, No. 25, pp. 6172-6185.

Hu et al., "Theoretical Investigation on the White-Light Emission from a Single-Polymer System with Simultaneous Blue and Orange Emission (Part II)," European Polymer Journal, Feb. 2011, vol. 47, No. 2, pp. 208-224.

Ishi-I et al., "Fluorescent Two-photon Absorption Benzothiadiazole Dyes Having Photoreleasing Quenchers," Chemistry Letters, 2009, vol. 38, No. 11, pp. 1042-1043.

Kato et al., "Novel 2,1,3-Benzothiadiazole-Based Red-Fluorescent Dyes with Enhanced Two-Photon Absorption Cross-Sections," Chemistry—A European Journal, Mar. 1, 2006, vol. 12, No. 8, pp. 2303-2317.

Karakus et al., "Electrochemical and Optical Properties of Solution Processable Benzotriazole and Benzothiadiazole Containing Copolymers," Synthetic Metals, Feb. 2012, vol. 162, No. 1-2, pp. 79-84.

Kato et al., "Strongly red-fluorescent novel donor-π-bridge-acceptor-π-bridge-donor (D-Π-A-Π-D) type 2,1,3-benzothiadiazoles with enhanced two-photon absorption cross-sections," Chemical Communications, 2004, vol. 20, pp. 2342-2343.

Kaya et al., "Electrochromic and Optical Studies of Solution Processable Benzotriazole and Fluorene Containing Copolymers," Organic Electronics, vol. 12, No. 1, Jan. 2011, pp. 202-209.

Shigeiwa, et al., "Two-Photon Absorption and Fluorescence Properties of Benzothiadiazole Dyes," Nonlinear Optics, Quantum Optics, 2005, vol. 34, No. 1-4, pp. 171-174.

Liu et al., "White Electroluminescence from a Star-like Polymer with an Orange Emissive Core and Four Blue Emissive Arms," Advanced Materials, 2008, vol. 20, No. 7, pp. 1357-1362.

Mikroyannidis et al., "Synthesis of Benzoselenadiazole-Based Small Molecule and Phenylenevinylene Copolymer and their Application for Efficient Bulk Heterojunction Solar Cells," Organic Electronics, Feb. 2010, vol. 11, No. 2, pp. 311-321.

Thomas et al., "Color Tuning in Benzo[1,2,5]thiadiazole-Based Small Molecules by Amino Conjugation/Deconjugation: Bright Red-Light-Emitting Diodes," Advanced Functional Materials, Jan. 2004, vol. 14, No. 1, pp. 83-90.

Velusamy et al., "Benzo[1,2,5]Selenadiazole Bridged Amines: Electro-Optical Properties," Tetrahedron Letters, Oct. 2005, vol. 46, No. 44, pp. 7647-7651.

Velusamy et al., "Organic Dyes Incorporating Low-Band-Gap Chromophores for Dye-Sensitized Solar Cells," Organic Letters, 2005, vol. 7, No. 10, pp. 1899-1902.

Yigitsoy et al., Benzyl Substituted Benzotriazole Containing Conjugated Polymers: Effect of Position of the Substituent on Electrochromic Properties, Synthetic Metals, vol. 160, No. 23-24, Dec. 2010, pp. 2534-2539.

(56) References Cited

OTHER PUBLICATIONS

Yang et al., "Theoretical Study of One-Photon and Two-Photon Absorption Properties for 2,1,3-Benzothiadiazole-Based Red-Fluorescent Dyes," Journal of Molecular Structure: Theochem, vol. 848, No. 1-3, Jan. 15, 2008, pp. 24-33.
Yasuda et al., "Benzothiadiazole-Triphenylamine Derivatives as Donor Materials for Bulk-Heterojunction Organic Solar Cells," Journal of Photopolymer Science and Technology, 2010, vol. 23, No. 3, pp. 307-312.
Yigitsoy et al., "Multichromic Polymers of Benzotriazole Derivatives: Effect of Benzyl Substitution," Electrochimica Acta, 2011, vol. 56, No. 5, pp. 2263-2268.
Zhang et al., "Copolymers from Benzodithiphene and Benzotriazole: Synthesis and Photovoltaic Applications", Polymer Chemistry, 2010, vol. 1, No. 9, pp. 1441-1447.
Zhang et al., "Synthesis and Photovoltaic Property of Alternating Copolymer Derived from 2,7-Carbazole and 4,7-Bis(2'-Thienyl)-2-Dodecyl-2,1,3-Benzotriazole," Polymer Preprints, 2011, vol. 52, No. 2, pp. 1000-1001.
Zhang et al., "Synthesis and Photovoltaic Properties of Dithienyl Benzotriazole Based Poly(phenylene vinylene)s", Journal of Applied Polymer Science, 2011, vol. 120, pp. 2534-2542.
Office Action and English Translation in corresponding Chinese Application No. 201280001373.X mailed on Jul. 17, 2014 in 32 pages.
Balan et al., "Electrochromic Device and Bulk Heterojunction Solar Cell Applications of Poly 4,7-bis(2,3-dihydrothieno[3,4-b][1,4]dioxin-5-yl)-2-dodecyl-2H-benzo[1,2,3]triazole (PBEBT)," Solar Energy Materials & Solar Cells, 2010, vol. 94, pp. 1797-1802.
Currie et al., "High-Efficiency Organic Solar Concentrators for Photovoltaics," Science, 2008, vol. 321, pp. 226.
Glaeser et al., "Improvement of Photon Collection in Cu(In,Ga)Se2 Solar Cells and Modules by Fluorescent Frequency Conversion," Thin Solid Films, 2007, vol. 515, pp. 5964-5967.
Hasobe et al., "Hierarchical Assembly of Porphyrins and Fullerenes for Solar Cells," The Electrochemical Society Interface, Summer 2006, pp. 47-51.
Hong et al., "Organic Dye-doped Thin Films for Wavelength Conversion and Their Effects on the Photovoltaic Characteristics of CdS/CdTe Solar cell," Japan Journal of Applied Physics, 2004, vol. 43, pp. 1421-1426.
Jones et al., "Tuning Orbital Energetics in Arylene Diimide Semiconductors, Materials Design for Ambient Stability of n-Type Charge Transport," Journal of American Chemical Society, 2007, vol. 129, pp. 15259-15278.
Krebs et al., "Product integration of compact roll-to-roll processed polymer solar cell modules: methods and manufacture using flexographic printing, slot-die coating and rotary screen printing," Journal Material Chemistry, 2010, 20, 8994-9001.
Lin et al., "High Photoelectric Conversion Efficiency of Metal Phthalocyanine/Fullerene Heterojunction Photovoltaic Device," International Journal of Molecular Sciences, 2011, vol. 12, pp. 476-505.
Lui et al., "A Dithienyl Benzotriazole-based Polyfluorene: Synthesis and Applications in Polymer Solar Cells and Red Light-Emitting Diodes," Macromolecular Chemistry and Physics, 2011, vol. 212, No. 14, pp. 1489-196.
Min et al., "Synthesis and Photovoltaic Properties of D-A Copolymers Based on Dithienosilole and Benzotriazole," Macromolecules, 2011, vol. 44, No. 19, pp. 7632-7638.
Muffler et al., "Colloid Attachment by ILGAR-layers: Creating Fluorescing Layers to Increase Quantum Efficiency of Solar Cells," Solar Energy Materials and Solar Cells, 2006, vol. 90, pp. 3143-3150.
Pasker et al., "Photovoltaic Response to Structural Modifications on a Series of Conjugated Polymers Based on 2-Aryl-2H-benzotriazoles," Polymer Chemistry, 2011, vol. 49, No. 23, pp. 5001-5011.
Singh-Rachford et al., "Photon Upconversion Based on Sensitized Triplet-Triplet Annihilation," Coordination Chemistry Reviews 254, 2010, pp. 2560-2573.

Xu et al., "Conjugated Polymers for Optoelectronic Applications," Macromolecular Symposia, 2008, pp. 161-170.
Yuan et al., "Efficient Synthesis of Regioisomerically Pure Bis(trufluoromethyl)-Substituted 3,4,9,10-Perylene Tetracarboxylic Bis(benzimidazole)," Organic Letters, 2009, vol. 11, No. 13, pp. 2808-2811.
Zhang et al., "Synthesis and Characterization of Perylene Tetracarboxylic Bisester Monoimide Derivatives," Dyes and Pigments Journal, 2008, vol. 76, pp. 810-816.
DuPont Teflon Films for Photovoltaic Modules (Dec. 2006).
Tedlar Polyvinyl Fluoride Film, Du Pont—Product and Performance Guide, Dec. 1995, pp. 6.
International Search Report and Written Opinion in PCT Application No. PCT/US2012/058062, dated Jun. 12, 2013, 22 pages.
International Preliminary Report on Patentability and Written Opinion in PCT Application No. PCT/US2012/058062, dated Apr. 8, 2014, 13 pages.
International Search Report and Written Opinion in PCT Application No. PCT/US2013/024225, dated May 7, 2013, 12 pages.
International Search Report and Written Opinion in PCT Application No. PCT/US2013/024212, dated Apr. 23, 2013, 15 pages.
International Search Report and Written Opinion in PCT Application No. PCT/US2012/053218, dated Apr. 22, 2013, 16 pages.
International Search Report and Written Opinion in PCT Application No. PCT/US2012/020209, dated Jul. 17, 2012, 14 pages.
First Office Action and English Translation in corresponding Chinese Appl. No. 201280001371.0 mailed on Feb. 4, 2015, 23 pages.
First Office Action in corresponding U.S. Appl. No. 13/626,679 mailed on Apr. 14, 2015, 25 pages.
Indian Journal of Pure and Applied Physics, vol. 33, pp. 169-178, (1995).
Japanese Office Action and Translation dated Feb. 28, 2015, which issued during prosecution of Japanese Application No. 2013-266062.
Fu, et al. Functional Polymers LII ** Synthesis and Polycondensation of 2(2,4,-Dihydroxyphenyl)2H-1,3-bis[4-carboxy (or 4-carbomethoxyy)2H-benzotriazole], Monatshefte fuer Chemie, 1988, 119:1200-1309.
Murugesan, et al. "Synthesis and characterizations of benzotriazole based donor-acceptor copolymers for organic photovoltaic applications" Synthetic Metals, 2012, 162:1037-1045.
Kamel, et al. "Studies on Some Benzotriazole Derivatives" Tetrahedron, 1964, 20:211-214.
Milata, et al. "4-Aminoethylene Derivatives of 2-Methylbenzotriazole" Collection of Czechoslovak Chemical Communications, 1990, 55(4):1038-1048.
Canada, et al. "On the Possibility of Chlorotropy in Aromatic Azoles: The Case of 1,2, 3-Triazoles and Benzotriazoles" Heterocycles, 1985, 23(9):2225-2228.
Sanna, et al. "1,2,3-Triazolo[4,5-H]Quinolines. III. Preparation and Antimicrobial Evaluation of 4-Ethyl 4,7, Dihydro 1(2)-R-1(2)H Triazolo [4,,5-H] Quinolin 7 One (Carboxylic Acis As Anti Infectives of the Urinary Tract" IL Farmaco, 1992, 47(7,8):1001-1019.
Katritzky, et al. "Influence of Structure on the Isomerization of Dialkylaminoalkylbenzotriazoles" Journal of Physical Organic Chemistry, 1990, 3:(5)289-294.
Katritzky, Perumal, et al. "An NMR Study of the Equilibria Involved with Benzotriazole, Carbonyl Compounds, and their Adducts" Journal of the Chemical Society, Perkin Transactions 2: Physical Organic Chemistry, 1990, 6:921-924.
Taiwan Office Action and Translation dated Jan. 20, 2016, which issued during prosecution of Taiwan Application No. 10520064870.
Fu, et al. Functional Polymer LII ** Synthesis and Polycondensation of 2(2,4,-Dihydroxyphenyl)2-H-1,3-bis[4-carboxy (or 4-carbomethoxy)2H-benzotriazole], Monatshefte fuer Chemic, 1988, 119:1299-1309.
Taiwan Office Action and Translation dated Jan. 20, 2016, which issued during prosecution of Taiwan Patent Application No. 101135970.

* cited by examiner

HIGHLY-FLUORESCENT AND PHOTO-STABLE CHROMOPHORES FOR ENHANCED SOLAR HARVESTING EFFICIENCY

CROSS-REFERENCE TO RELATED APPLICATIONS

This patent application claims the benefit of priority to U.S. Provisional Patent Application No. 61/539,392, filed Sep. 26, 2011, U.S. Provisional Patent Application No. 61/567,534, filed Dec. 6, 2011, U.S. Provisional Patent Application No. 61/662,825, filed Jun. 21, 2012, and U.S. Provisional Patent Application No. 61/662,835 filed Jun. 21, 2012. All of the foregoing applications are fully incorporated herein by reference for all purposes.

BACKGROUND

1. Field of the Invention

The present invention generally relates to photo-stable highly luminescent chromophores which are useful in various applications, including in wavelength conversion films. Wavelength conversion films have the potential to significantly enhance the solar harvesting efficiency of photovoltaic or solar cell devices.

2. Description of the Related Art

The utilization of solar energy offers a promising alternative energy source to the traditional fossil fuels, and therefore, the development of devices that can convert solar energy into electricity, such as photovoltaic devices (also known as solar cells), has drawn significant attention in recent years. Several different types of mature photovoltaic devices have been developed, including Silicon based device, III-V and II-VI PN junction devices, Copper-Indium-Gallium-Selenium (CIGS) thin film devices, organic sensitizer devices, organic thin film devices, and Cadmium Sulfide/Cadmium Telluride (CdS/CdTe) thin film devices, to name a few. More detail on these devices can be found in the literature, such as Lin et al., "High Photoelectric Conversion Efficiency of Metal Phthalocyanine/Fullerene Heterojunction Photovoltaic Device" (International Journal of Molecular Sciences, vol. 12, pp. 476, 2011). However, the photoelectric conversion efficiency of many of these devices still has room for improvement and development of techniques to improve this efficiency has been an ongoing challenge for many researchers.

One technique developed to improve the efficiency of photovoltaic devices is to utilize a wavelength conversion film. Many of the photovoltaic devices are unable to effectively utilize the entire spectrum of light as the materials on the device absorb certain wavelengths of light (typically the shorter UV wavelengths) instead of allowing the light to pass through to the photoconductive material layer where it is converted into electricity. Application of a wavelength conversion film absorbs the shorter wavelength photons and re-emits them at more favorable longer wavelengths, which can then be absorbed by the photoconductive layer in the device, and converted into electricity.

This phenomenon is often observed in the thin film CdS/CdTe and CIGS solar cells which both use CdS as the window layer. The low cost and high efficiency of these thin film solar cells has drawn significant attention in recent years, with typical commercial cells having photoelectric conversion efficiencies of 10-16%. However, the energy gap of CdS is approximately 2.41 eV, which causes light at wavelengths below 514 nm to be absorbed by CdS instead of passing through to the photoconductive layer where it can be converted into energy. This inability to utilize the entire spectrum of light effectively reduces the overall photoelectric conversion efficiency of the device.

There have been numerous reports disclosing the utilization of wavelength conversion materials to improve the performance of photovoltaic devices. For example, U.S. Patent Application Publication No. 2009/0151785 discloses a silicon based solar cell device which contains a wavelength down-shifting inorganic phosphor material. U.S. Patent Application Publication No. US 2011/0011455 discloses an integrated solar cell comprising a plasmonic layer, a wavelength conversion layer, and a photovoltaic layer. U.S. Pat. No. 7,791,157 discloses a solar cell with a wavelength conversion layer containing a quantum dot compound.

While there have been numerous disclosures of wavelength conversion inorganic mediums used in photovoltaic devices and solar cells, there has been very little work reported on the use of photo-luminescent organic mediums for efficiency improvements in photovoltaic devices. The use of an organic medium, as opposed to an inorganic medium, is attractive in that organic materials are typically cheaper and easier to use, making them a better economical choice. Some theoretical modeling and/or simulation of luminescent films applied to CdS/CdTe solar cells is described in the following literature, U.S. Patent Application Publication No. 2010/0186801, B. S. Richards and K. R. McIntosh in "Overcoming the Poor Short Wavelength Spectral Response of CdS/CdTe Photovoltaic Modules via Luminescence Down-Shifting: Ray-Tracing Simulations" (Progress in Photovoltaics: Research and Applications, vol. 15, pp. 27-34, 2007), and T. Maruyama and R. Kitamura in "Transformations of the wavelength of the light incident upon solar cells" (Solar Energy Materials and Solar Cells, vol. 69, pp. 207, 2001).

SUMMARY

Novel compounds of benzo heterocyclic system are disclosed. These compounds are useful as chromophores that provide desirable optical properties and good photo-stability.

Some embodiments provide a chromophore represented by formula I-a or formula I-b:

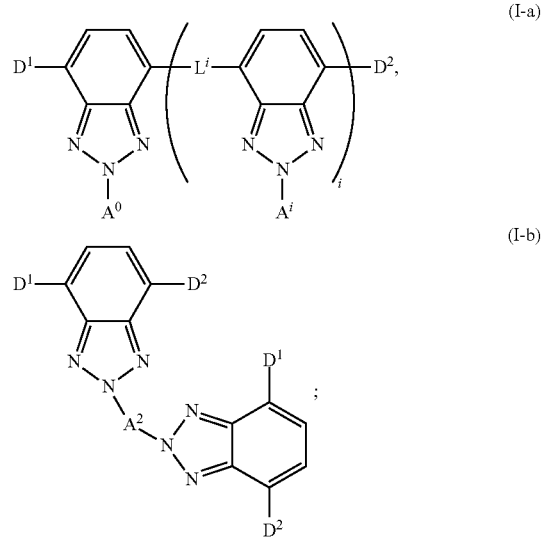

wherein i is an integer in the range of 0 to 100; $A^0$ and $A^i$ are each independently selected from the group consisting of optionally substituted alkyl, optionally substituted alkenyl, optionally substituted heteroalkyl, optionally substituted aryl, optionally substituted heteroaryl, optionally substituted amino, optionally substituted amido, optionally substituted cyclic amido, optionally substituted cyclic imido, optionally substituted alkoxy, and optionally substituted carboxy, and optionally substituted carbonyl.

$A^2$ is selected from the group consisting of optionally substituted alkylene, optionally substituted alkenylene, optionally substituted arylene, optionally substituted heteroarylene, ketone, ester, and

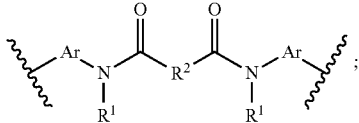

wherein Ar is optionally substituted aryl or optionally substituted heteroaryl.

$R^1$ is selected from the group consisting of H, alkyl, alkenyl, aryl, heteroaryl, aralkyl, alkaryl; and $R^2$ is selected from the group consisting of optionally substituted alkylene, optionally substituted alkenylene, optionally substituted arylene, optionally substituted heteroarylene, ketone, and ester; or $R^1$ and $R^2$ may be connected together to form a ring.

$D^1$ and $D^2$ are each independently selected from the group consisting of hydrogen, optionally substituted alkoxy, optionally substituted aryloxy, optionally substituted acyloxy, optionally substituted alkyl, optionally substituted aryl, optionally substituted heteroaryl, optionally substituted amino, amido, cyclic amido, and cyclic imido, provided that $D^1$ and $D^2$ are not both hydrogen.

$L^i$ is independently selected from the group consisting of optionally substituted alkylene, optionally substituted alkenylene, optionally substituted alkynylene, optionally substituted arylene, optionally substituted heteroarylene.

Some embodiments provide a compound represented by formula II-a or II-b:

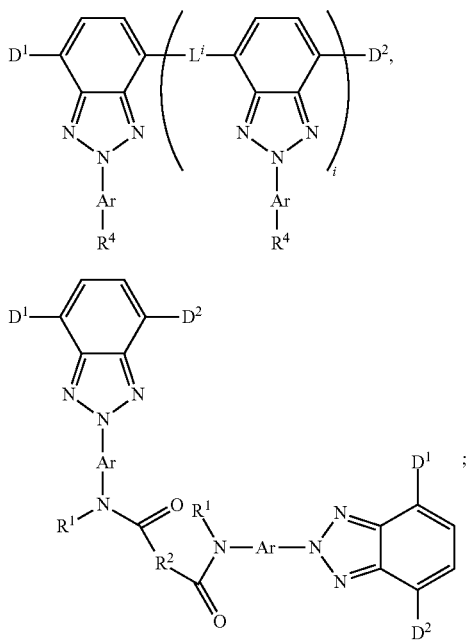

wherein i is an integer in the range of 0 to 100; Ar is optionally substituted aryl or optionally substituted heteroaryl; $R^4$ is

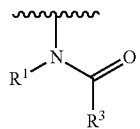

or optionally substituted cyclic imido; $R^1$ is each independently selected from the group consisting of H, alkyl, alkenyl, aryl, heteroaryl, aralkyl, alkaryl; $R^3$ is each independently selected from the group consisting of optionally substituted alkyl, optionally substituted alkenyl, optionally substituted aryl, optionally substituted heteroaryl; or R' and R" may be connected together to form a ring.

$R^2$ is selected from the group consisting of optionally substituted alkylene, optionally substituted alkenylene, optionally substituted arylene, optionally substituted heteroarylene.

$D^1$ and $D^2$ are each independently selected from the group consisting of hydrogen, optionally substituted alkoxy, optionally substituted aryloxy, optionally substituted acyloxy, optionally substituted alkyl, optionally substituted aryl, optionally substituted heteroaryl, optionally substituted amino, amido, cyclic amido, and cyclic imido, provided that $D^1$ and $D^2$ are not both hydrogen.

$L^i$ is independently selected from the group consisting of optionally substituted alkylene, optionally substituted alkenylene, optionally substituted alkynylene, optionally substituted arylene, optionally substituted heteroarylene.

Some embodiments provide a compound represented by formula III-a or III-b:

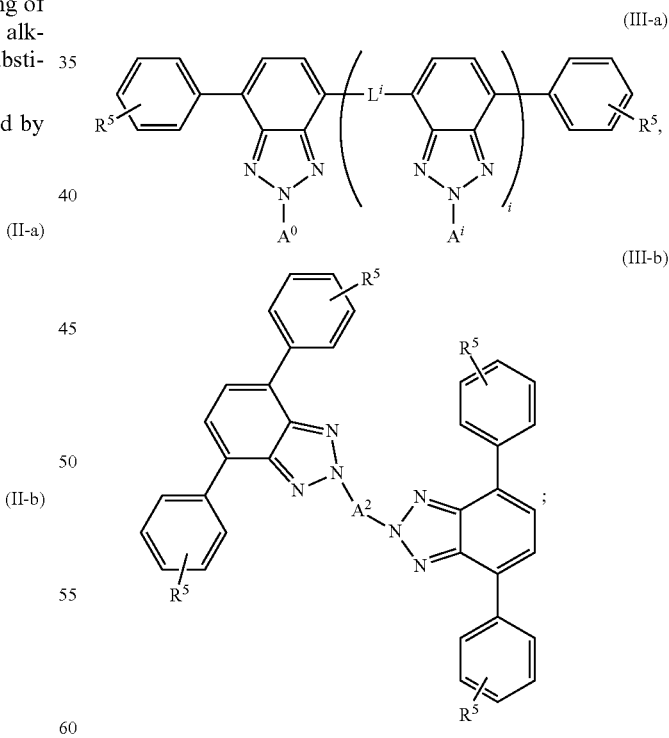

wherein i is an integer in the range of 0 to 100; $A^0$ and $A^i$ are each independently selected from the group consisting of optionally substituted alkyl, optionally substituted alkenyl, optionally substituted heteroalkyl, optionally substituted amido, optionally substituted alkoxy, optionally substituted cabonyl, and optionally substituted carboxy.

Each $R^5$ is independently selected from the group consisting of optionally substituted alkoxy, optionally substituted aryloxy, optionally substituted acyloxy, amino.

$A^2$ is selected from the group consisting of optionally substituted alkylene, optionally substituted alkenylene, optionally substituted arylene, optionally substituted heteroarylene, ketone, ester, and

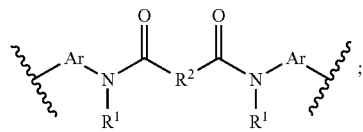

wherein Ar is optionally substituted aryl or optionally substituted heteroaryl, $R^1$ is selected from the group consisting of H, alkyl, alkenyl, aryl, heteroaryl, aralkyl, alkaryl; and $R^2$ is selected from the group consisting of optionally substituted alkylene, optionally substituted alkenylene, optionally substituted arylene, optionally substituted heteroarylene, ketone, and ester; or $R^1$ and $R^2$ may be connected together to form a ring.

$L^i$ is independently selected from the group consisting of optionally substituted alkylene, optionally substituted alkenylene, optionally substituted alkynylene, optionally substituted arylene, optionally substituted heteroarylene.

Some embodiments provide a chromophore represented by the formula (IV):

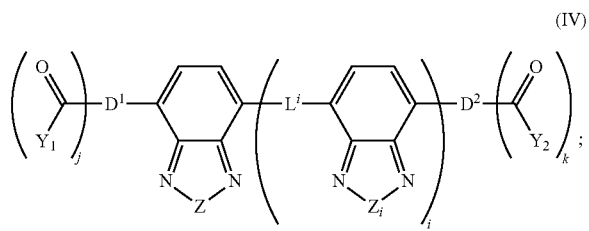

wherein i is an integer in the range of 0 to 100; Z and $Z_i$ are each independently selected from the group consisting of —O—, —S—, —Se—, —Te—, —$NR^6$—, —$CR^6$=$CR^6$—, and —$CR^6$=N—, wherein $R^6$ is hydrogen, optionally substitute $C_1$-$C_6$ alkyl, or optionally substituted $C_1$-$C_{10}$ aryl; and $D^1$ and $D^2$ are independently selected from the group consisting of optionally substituted alkoxy, optionally substituted aryloxy, optionally substituted acyloxy, optionally substituted alkyl, optionally substituted aryl, optionally substituted heteroaryl, optionally substituted amino, amido, cyclic amido, and cyclic imido; j is 0, 1 or 2, and k is 0, 1, or 2.

$Y_1$ and $Y_2$ are independently selected from the group consisting of optionally substituted aryl, optionally substituted alkyl, optionally substituted cycloalkyl, optionally substituted alkoxy, and optionally substituted amino; and $L^i$ is independently selected from the group consisting of optionally substituted alkylene, optionally substituted alkenylene, optionally substituted alkynylene, optionally substituted arylene, optionally substituted heteroarylene.

Some embodiments also provide a wavelength conversion luminescent medium comprising an optically transparent polymer matrix and at least one luminescent dye comprising a chromophore as disclosed herein.

Some embodiments also provide a photovoltaic module comprising at least one photovoltaic device or solar cell, and a wavelength conversion luminescent medium as disclosed herein, wherein the wavelength conversion luminescent medium is positioned such that the incident light passes through the wavelength conversion luminescent medium prior to reaching the photovoltaic device or solar cell.

Some embodiment provide a method for improving the performance of a photovoltaic device of solar cell, comprising applying a wavelength conversion luminescent medium as disclosed herein directly onto the light incident side of the photovoltaic device or solar cell, or encapsulate the wavelength conversion luminescent medium in the photovoltaic device or solar cell.

Further aspects, features and advantages of this invention will become apparent from the detailed description of the preferred embodiments which follow.

DETAILED DESCRIPTION OF THE EMBODIMENTS

Figure 1:
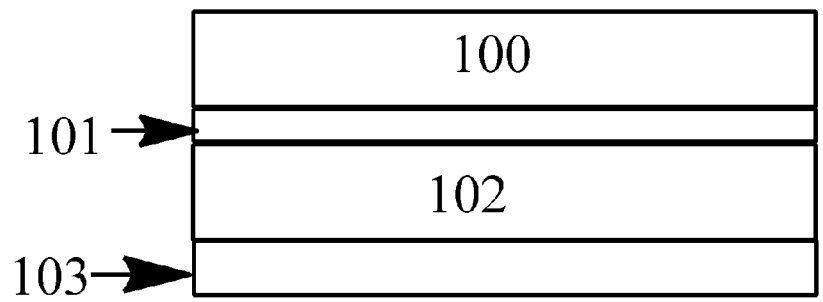
FIG. 1 illustrates a photovoltaic device or solar cell in which a thin film wavelength conversion luminescent medium is directly attached to the light incident surface of the device.

One of the useful properties of fluorescence (or photoluminescent) dyes is that they have the ability to absorb light photons of a particular wavelength, and re-emit the photons at a different wavelength. This phenomenon also makes them useful in the photovoltaic industry.

The chromophores represented by general formulae I-a, I-b, II-a, II-b, III-a, III-b, and IV are useful as fluorescent dyes in various applications, including in wavelength conversion films. As shown in the formulae, the dye comprises a benzo heterocyclic system. Additional detail and examples, without limiting the scope of the invention, on the types of compounds that can be used are described below.

The benzo heterocyclic system disclosed herein includes a 2H-benzo[d][1,2,3]triazole system. The atom numbering is displayed below:

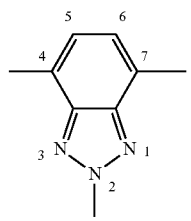

As used herein, an "electron donor group" is defined as any group which increases the electron density of the 2H-benzo[d][1,2,3]triazole system.

An "electron donor linker" is defined as any group that can link two 2H-benzo[d][1,2,3]triazole systems providing conjugation of their π orbitals, which can also increase or have neutral effect on the electron density of the 2H-benzo[d][1,2,3]triazole to which they are connected.

An "electron acceptor group" is defined as any group which decreases the electron density of the 2H-benzo[d][1,2,3]triazole system. The placement of an electron acceptor group at the N-2 position of the 2H-benzo[d][1,2,3]triazole ring system.

The term "alkyl" refers to a branched or straight fully saturated acyclic aliphatic hydrocarbon group (i.e. composed of carbon and hydrogen containing no double or triple bonds). Alkyls include, but are not limited to, methyl, ethyl, propyl, isopropyl, butyl, isobutyl, tertiary butyl, pentyl, hexyl, and the like.

The term "heteroaryl" used herein refers to an aromatic group comprising one or more heteroatoms, whether one ring or multiple fused rings. When two or more heteroatoms are present, they may be the same or different. In fused ring systems, the one or more heteroatoms may be present in only one of the rings. Examples of heteroaryl groups include, but are not limited to, benzothiazyl, benzoxazyl, quinazolinyl, quinolinyl, isoquinolinyl, quinoxalinyl, pyridinyl, pyrrolyl, oxazolyl, indolyl, thiazyl and the like.

The term "cycloalkyl" used herein refers to saturated aliphatic ring system radical having three to twenty carbon atoms including, but not limited to, cyclopropyl, cyclopentyl, cyclohexyl, cycloheptyl, and the like.

The term "alkenyl" used herein refers to a monovalent straight or branched chain radical of from two to twenty carbon atoms containing a carbon double bond including, but not limited to, 1-propenyl, 2-propenyl, 2-methyl-1-propenyl, 1-butenyl, 2-butenyl, and the like.

The term "alkynyl" used herein refers to a monovalent straight or branched chain radical of from two to twenty carbon atoms containing a carbon triple bond including, but not limited to, 1-propynyl, 1-butynyl, 2-butynyl, and the like.

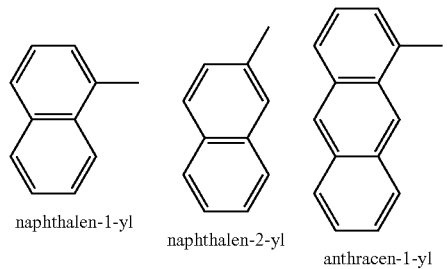

naphthalen-1-yl  naphthalen-2-yl  anthracen-1-yl

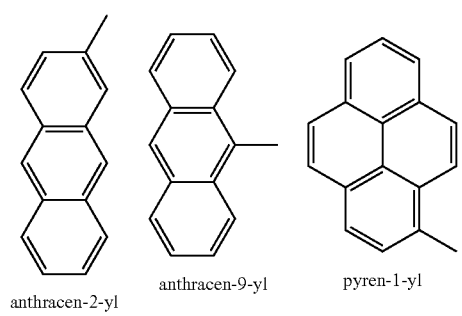

anthracen-2-yl  anthracen-9-yl  pyren-1-yl

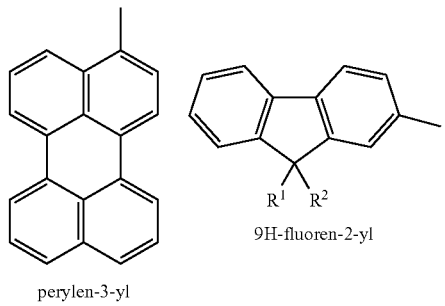

perylen-3-yl  9H-fluoren-2-yl

The term "aryl" used herein refers to homocyclic aromatic radical whether one ring or multiple fused rings. Examples of aryl groups include, but are not limited to, phenyl, naphthyl, phenanthrenyl, naphthacenyl, fluorenyl, pyrenyl, and the like. Further examples include:***

The term "heteroaryl" used herein refers to an aromatic group comprising one or more heteroatoms, whether one ring or multiple fused rings. When two or more heteroatoms are present, they may be the same or different. In fused ring systems, the one or more heteroatoms may be present in only one of the rings. Examples of heteroaryl groups include, but are not limited to, benzothiazyl, benzoxazyl, quinazolinyl, quinolinyl, isoquinolinyl, quinoxalinyl, pyridinyl, pyrrolyl, oxazolyl, indolyl, thiazyl and the like.

The term "alkaryl" or "alkylaryl" used herein refers to an alkyl-substituted aryl radical. Examples of alkaryl include, but are not limited to, ethylphenyl, 9,9-dihexyl-9H-fluorene, and the like.

The term "aralkyl" or "arylalkyl" used herein refers to an aryl-substituted alkyl radical. Examples of aralkyl include, but are not limited to, phenylpropyl, phenylethyl, and the like.

The term "heteroaryl" used herein refers to an aromatic ring system radical in which one or more ring atoms are heteroatoms, whether one ring or multiple fused rings. When two or more heteroatoms are present, they may be the same or different. In fused ring systems, the one or more heteroatoms may be present in only one of the rings. Examples of heteroaryl groups include, but are not limited to, benzothiazyl, benzoxazyl, quinazolinyl, quinolinyl, isoquinolinyl, quinoxalinyl, pyridinyl, pyridazinyl, pyrimidinyl, pyrazinyl, pyrrolyl, oxazolyl, indolyl, and the like. Further examples of substituted and unsubstituted heteroaryl rings include:

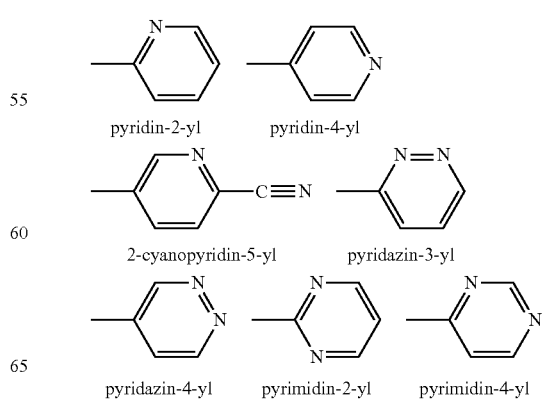

pyridin-2-yl  pyridin-4-yl 2-cyanopyridin-5-yl  pyridazin-3-yl pyridazin-4-yl  pyrimidin-2-yl  pyrimidin-4-yl

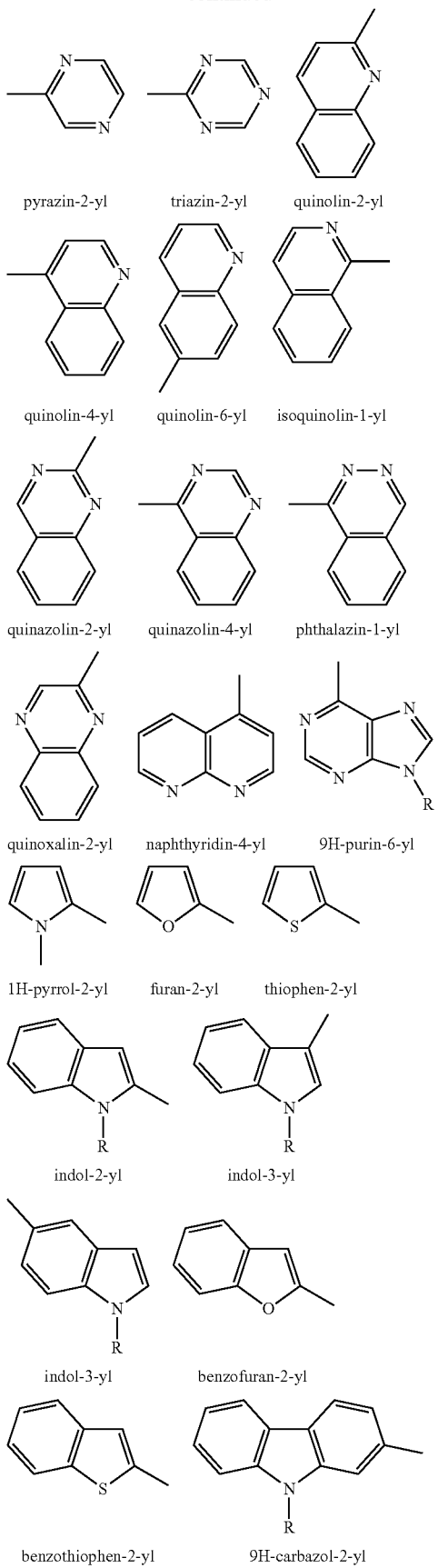
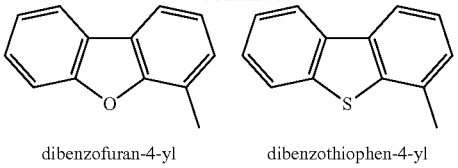

dibenzofuran-4-yl    dibenzothiophen-4-yl

The term "alkoxy" used herein refers to straight or branched chain alkyl radical covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like.

The term "heteroatom" used herein refers to S (sulfur), N (nitrogen), and O (oxygen).

The term "cyclic amino" used herein refers to either secondary or tertiary amines in a cyclic moiety. Examples of cyclic amino groups include, but are not limited to, aziridinyl, piperidinyl, N-methylpiperidinyl, and the like.

The term "cyclic imido" used herein refers to an imide in the radical of which the two carbonyl carbons are connected by a carbon chain. Examples of cyclic imide groups include, but are not limited to, 1,8-naphthalimide, pyrrolidine-2,5-dione, 1H-pyrrole-2,5-dione, and the likes.

The term "aryloxy" used herein refers to an aryl radical covalently bonded to the parent molecule through an —O— linkage.

The term "acyloxy" used herein refers to a radical R—C(=O)O—.

The term "carbamoyl" used herein refers to —NHC(=O)R.

The term "keto" and "carbonyl" used herein refers to C=O.

The term "carboxy" used herein refers to —COOH.
The term "ester" used herein refers to C(=O)O.
The term "amido" used herein refers to —NRC(=O)R'.
The term "amino" used herein refers to —NR'R"

As used herein, a substituted group is derived from the unsubstituted parent structure in which there has been an exchange of one or more hydrogen atoms for another atom or group. When substituted, the substituent group(s) is (are) one or more group(s) individually and independently selected from $C_1$-$C_6$ alkyl, $C_1$-$C_6$ alkenyl, $C_1$-$C_6$ alkynyl, $C_3$-$C_7$ cycloalkyl (optionally substituted with halo, alkyl, alkoxy, carboxyl, haloalkyl, CN, —$SO_2$-alkyl, —$CF_3$, and —$OCF_3$), cycloalkyl geminally attached, $C_1$-$C_6$ heteroalkyl, $C_3$-$C_{10}$ heterocycloalkyl (e.g., tetrahydrofuryl) (optionally substituted with halo, alkyl, alkoxy, carboxyl, CN, —$SO_2$-alkyl, —$CF_3$, and —$OCF_3$), aryl (optionally substituted with halo, alkyl, aryl optionally substituted with $C_1$-$C_6$ alkyl, arylalkyl, alkoxy, aryloxy, carboxyl, amino, imido, amido (carbamoyl), optionally substituted cyclic imido, cyclic amido, CN, —NH—C(=O)-alkyl, —$CF_3$, and —$OCF_3$), arylalkyl (optionally substituted with halo, alkyl, alkoxy, aryl, carboxyl, CN, —$SO_2$-alkyl, —$CF_3$, and —$OCF_3$), heteroaryl (optionally substituted with halo, alkyl, alkoxy, aryl, heteroaryl, aralkyl, carboxyl, CN, —$SO_2$-alkyl, —$CF_3$, and —$OCF_3$), halo (e.g., chloro, bromo, iodo and fluoro), cyano, hydroxy, optionally substituted cyclic imido, amino, imido, amido, —$CF_3$, $C_1$-$C_6$ alkoxy, aryloxy, acyloxy, sulfhydryl (mercapto), halo($C_1$-$C_6$)alkyl, $C_1$-$C_6$ alkylthio, arylthio, mono- and di-($C_1$-$C_6$)alkyl amino, quaternary ammonium salts, amino($C_1$-$C_6$)alkoxy, hydroxy($C_1$-$C_6$)alkylamino, amino($C_1$-$C_6$)alkylthio, cyanoamino, nitro, carbamoyl, keto (oxy), carbonyl, carboxy, glycolyl, glycyl, hydrazino, guanyl, sulfamyl, sulfonyl, sulfinyl, thiocarbonyl, thiocarboxy, sulfonamide, ester, C-amide, N-amide, N-carbamate, O-carbamate, urea and combinations thereof. Wherever a substituent is described as "optionally substituted" that substituent can be substituted with the above substituents.

Formulae I-a and I-b

Some embodiments provide a chromophore having one of the structures below:

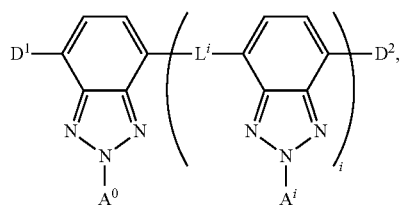

(I-a)

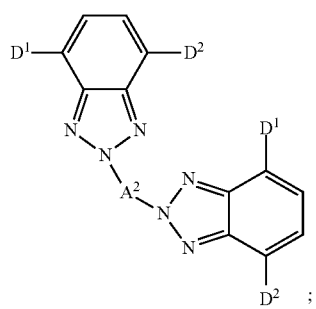

(I-b)

wherein $D^1$ and $D^2$ are electron donating groups, $L^i$ is an electron donor linker, and $A^0$ and $A^i$ are electron acceptor groups. In some embodiments, where more than one electron donor group is present, the other electron donor groups may be occupied by another electron donor, a hydrogen atom, or another neutral substituent. In some embodiments, at least one of the $D^1$, $D^2$, and $L^i$ is a group which increases the electron density of the 2H-benzo[d][1,2,3]triazole system to which it is attached.

In formulae I-a and I-b, i is an integer in the range of 0 to 100. In some embodiments, i is an integer in the range of 0 to 50, 0 to 30, 0 to 10, 0 to 5, or 0 to 3. In some embodiments, i is 0, 1, 2, 3, 4, 5, 6, 7, 8, 9, or 10.

In formulae I-a and I-b, $A^0$ and $A^i$ are each independently selected from the group consisting of optionally substituted alkyl, optionally substituted alkenyl, optionally substituted heteroalkyl, optionally substituted aryl, optionally substituted heteroaryl, optionally substituted amino, optionally substituted amido, optionally substituted cyclic amido, optionally substituted cyclic imido, optionally substituted alkoxy, and optionally substituted carboxy, and optionally substituted carbonyl.

In some embodiments, $A^0$ and $A^i$ are each independently selected from the group consisting of optionally substituted heteroaryl, optionally substituted aryl, optionally substituted cyclic imido, optionally substituted $C_{1-8}$ alkyl, and optionally substituted $C_{1-8}$ alkenyl; wherein the substituent for optionally substituted heteroaryl is selected from the group consisting of alkyl, aryl and halogen; the substituent for optionally substituted aryl is —$NR^1$—$C(=O)R^2$ or optionally substituted cyclic imido, wherein $R^1$ and $R^2$ are as described above.

In some embodiments, $A^0$ and $A^i$ are each independently phenyl substituted with a moiety selected from the group consisting of —$NR^1$—$C(=O)R^2$ and optionally substituted cyclic imido, wherein $R^1$ and $R^2$ are as described above.

In some embodiments, $A^0$ and $A^i$ are each optionally substituted heteroaryl or optionally substituted cyclic imido; wherein the substituent for optionally substituted heteroaryl and optionally substituted cyclic imido is selected from the group consisting of alkyl, aryl and halogen. In some embodiments, at least one of the $A^0$ and $A^i$ is selected from the group consisting of: optionally substituted pyridinyl, optionally substituted pyridazinyl, optionally substituted pyrimidinyl, optionally substituted pyrazinyl, optionally substituted triazinyl, optionally substituted quinolinyl, optionally substituted isoquinolinyl, optionally substituted quinazolinyl, optionally substituted phthalazinyl, optionally substituted quinoxalinyl, optionally substituted naphthyridinyl, and optionally substituted purinyl.

In other embodiments, $A^0$ and $A^i$ are each optionally substituted alkyl. In other embodiments, $A^0$ and $A^i$ are each optionally substituted alkenyl. In some embodiments, at least one of the $A^0$ and $A^i$ is selected from the group consisting of:

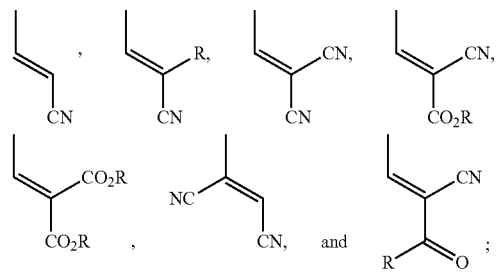

wherein R is optionally substituted alkyl.

In formula I-a and I-b, $A^2$ is selected from the group consisting of optionally substituted alkylene, optionally substituted alkenylene, optionally substituted arylene, optionally substituted heteroarylene, ketone, ester, and

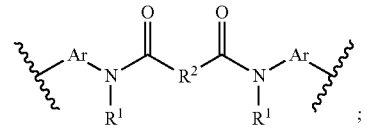

wherein Ar is optionally substituted aryl or optionally substituted heteroaryl. $R^1$ is selected from the group consisting of H, alkyl, alkenyl, aryl, heteroaryl, aralkyl, alkaryl; and $R^2$ is selected from the group consisting of optionally substituted alkylene, optionally substituted alkenylene, optionally substituted arylene, optionally substituted heteroarylene, ketone, and ester; or $R^1$ and $R^2$ may be connected together to form a ring.

In some embodiments, $A^2$ is selected from the group consisting of optionally substituted arylene, optionally substituted heteroarylene, and

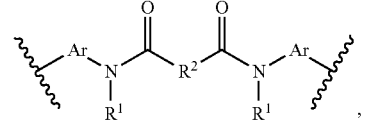

wherein Ar, $R^1$ and $R^2$ are as described above.

In formulae I-a and I-b, $D^1$ and $D^2$ are each independently selected from the group consisting of hydrogen, optionally substituted alkoxy, optionally substituted aryloxy, optionally substituted acyloxy, optionally substituted alkyl, optionally substituted aryl, optionally substituted heteroaryl, optionally substituted amino, amido, cyclic amido, and cyclic imido, provided that $D^1$ and $D^2$ are not both hydrogen.

In some embodiments, $D^1$ and $D^2$ are each independently selected from the group consisting of hydrogen, optionally substituted aryl, optionally substituted heteroaryl, and amino, provided that $D^1$ and $D^2$ are not both hydrogen. In some embodiments, $D^1$ and $D^2$ are each independently selected from the group consisting of hydrogen, optionally substituted aryl, optionally substituted heteroaryl, and diphenylamino, provided that $D^1$ and $D^2$ are not both hydrogen.

In some embodiments, $D^1$ and $D^2$ are each independently optionally substituted aryl. In some embodiments, $D^1$ and $D^2$ are each independently phenyl optionally substituted by alkoxy or amino. In other embodiments, $D^1$ and $D^2$ are each independently selected from hydrogen, optionally substituted benzofuranyl, optionally substituted thiophenyl, optionally substituted furanyl, dihydrothienodioxinyl, optionally substituted benzothiophenyl, and optionally substituted dibenzothiophenyl, provided that $D^1$ and $D^2$ are not both hydrogen.

In some embodiments, the substituent for optionally substituted aryl and optionally substituted heteroaryl may be selected from the group consisting of alkoxy, aryloxy, aryl, heteroaryl, and amino.

In formulae I-a and I-b, $L^i$ is independently selected from the group consisting of optionally substituted alkylene, optionally substituted alkenylene, optionally substituted alkynylene, optionally substituted arylene, optionally substituted heteroarylene. In some embodiments, $L^i$ is selected from the group consisting of optionally substituted heteroarylene and optionally substituted arylene.

In some embodiments, at least one of the $L^i$ is selected from the group consisting of: 1,2-ethylene, acetylene, 1,4-phenylene, 1,1'-biphenyl-4,4'-diyl, naphthalene-2,6-diyl, naphthalene-1,4-diyl, 9H-fluorene-2,7-diyl, perylene-3,9-diyl, perylene-3,10-diyl, or pyrene-1,6-diyl, 1H-pyrrole-2,5-diyl, furan-2,5-diyl, thiophen-2,5-diyl, thieno[3,2-b]thiophene-2,5-diyl, benzo[c]thiophene-1,3-diyl, dibenzo[b,d]thiophene-2,8-diyl, 9H-carbozole-3,6-diyl, 9H-carbozole-2,7-diyl, dibenzo[b,d]furan-2,8-diyl, 10H-phenothiazine-3,7-diyl, and 10H-phenothiazine-2,8-diyl; wherein each moiety is optionally substituted.

Formulae II-a and II-b

Some embodiments provide a chromophore having one of the structures below:

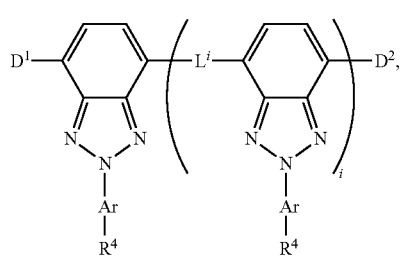

(II-a)

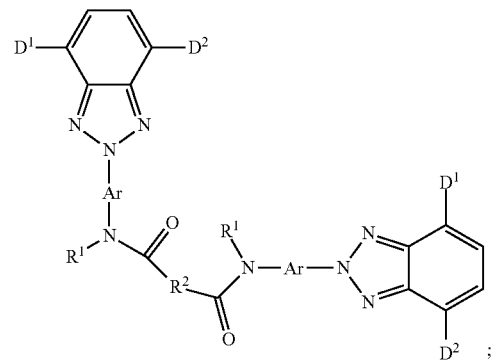

(II-b)

wherein i is an integer in the range of 0 to 100. In some embodiments, i is an integer in the range of 0 to 50, 0 to 30, 0 to 10, 0 to 5, or 0 to 3. In some embodiments, i is 0, 1, 2, 3, 4, 5, 6, 7, 8, 9, or 10.

In formulae II-a and II-b, Ar is optionally substituted aryl or optionally substituted heteroaryl. In some embodiments, aryl substituted with an amido or a cyclic imido group at the N-2 position of the 2H-benzo[d][1,2,3]triazole ring system provides unexpected and improved benefits.

In formulae II-a and II-b, $R^4$ is

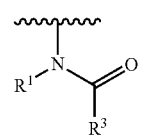

or optionally substituted cyclic imido; $R^1$ is each independently selected from the group consisting of H, alkyl, alkenyl, aryl, heteroaryl, aralkyl, alkaryl; $R^3$ is each independently selected from the group consisting of optionally substituted alkyl, optionally substituted alkenyl, optionally substituted aryl, optionally substituted heteroaryl; or R' and R" may be connected together to form a ring.

In some embodiments, $R^4$ is optionally substituted cyclic imido selected from the group consisting of:

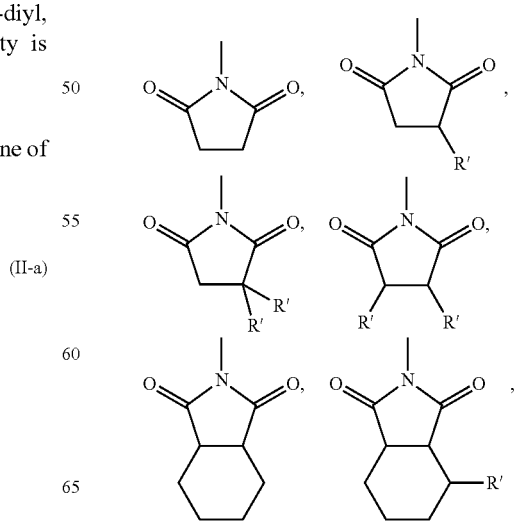

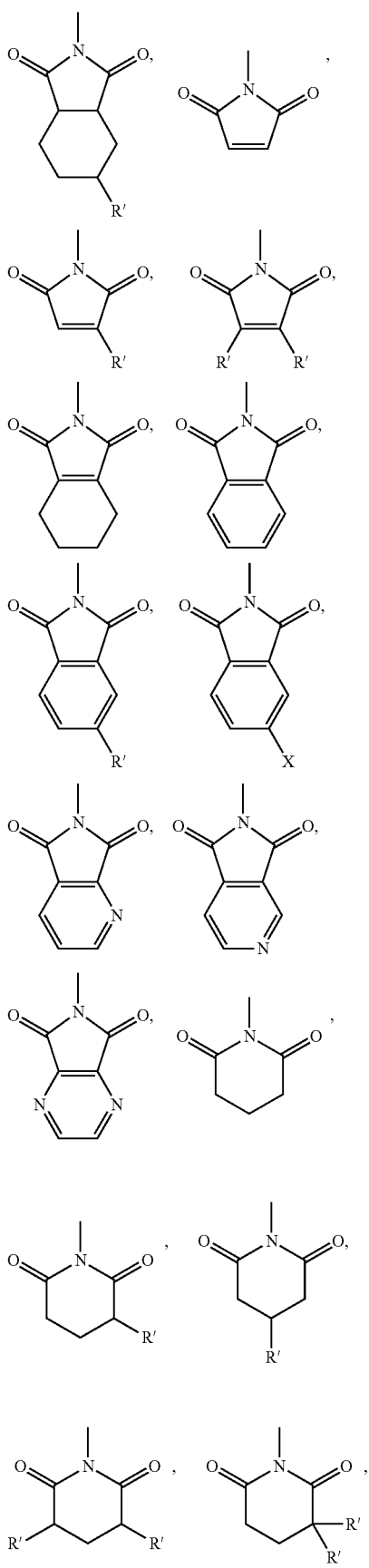

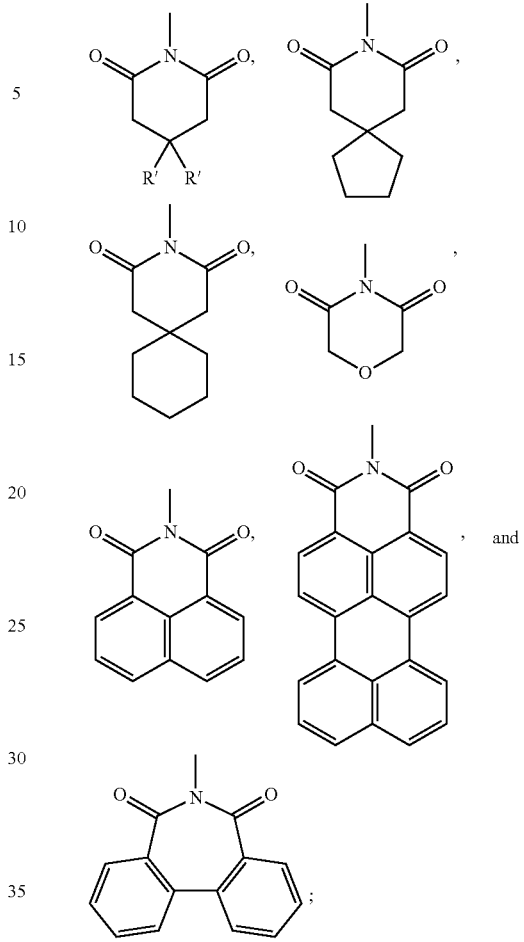

and wherein R' is each optionally substituted alkyl or optionally substituted aryl; and X is optionally substituted heteroalkyl.

In formulae II-a and II-b, $R^2$ is selected from the group consisting of optionally substituted alkylene, optionally substituted alkenylene, optionally substituted arylene, optionally substituted heteroarylene.

In formulae II-a and II-b, $D^1$ and $D^2$ are each independently selected from the group consisting of hydrogen, optionally substituted alkoxy, optionally substituted aryloxy, optionally substituted acyloxy, optionally substituted alkyl, optionally substituted aryl, optionally substituted heteroaryl, optionally substituted amino, amido, cyclic amido, and cyclic imido, provided that $D^1$ and $D^2$ are not both hydrogen.

In formulae II-a and II-b, $L^i$ is independently selected from the group consisting of optionally substituted alkylene, optionally substituted alkenylene, optionally substituted alkynylene, optionally substituted arylene, optionally substituted heteroarylene.

In some embodiments, at least one of the $L^i$ is selected from the group consisting of: 1,2-ethylene, acetylene, 1,4-phenylene, 1,1'-biphenyl-4,4'-diyl, naphthalene-2,6-diyl, naphthalene-1,4-diyl, 9H-fluorene-2,7-diyl, perylene-3,9-diyl, perylene-3,10-diyl, or pyrene-1,6-diyl, 1H-pyrrole-2,5-diyl, furan-2,5-diyl, thiophen-2,5-diyl, thieno[3,2-b]thiophene-2,5-diyl, benzo[c]thiophene-1,3-diyl, dibenzo[b,d]thiophene-2,8-diyl, 9H-carbozole-3,6-diyl, 9H-carbozole-2,7-diyl, dibenzo[b,d]furan-2,8-diyl, 10H-phenothiazine-3,7-diyl, and 10H-phenothiazine-2,8-diyl; wherein each moiety is optionally substituted.

Formulae III-a and III-b

Some embodiments provide a chromophore having one of the structures below:

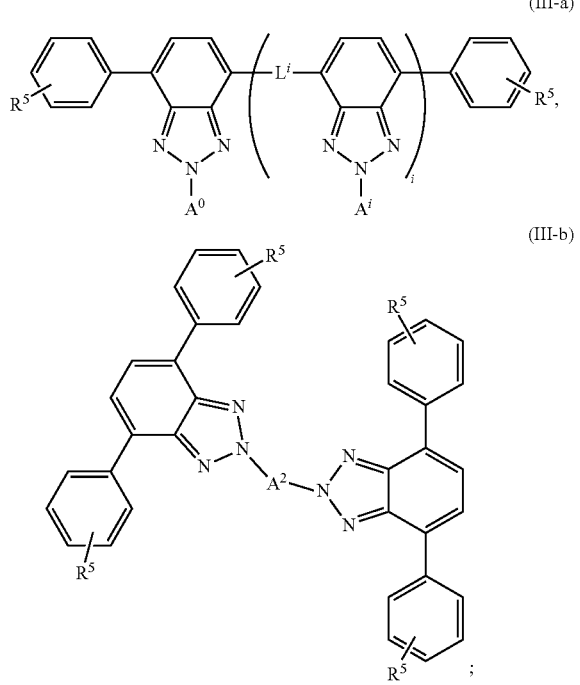

The placement of an alkyl group in formulae (III-a) and (III-b) at the N-2 position of the 2H-benzo[d][1,2,3]triazole ring system along with substituted phenyls at the C-4 and C-7 positions provides unexpected and improved benefits. In formula III-a and III-b, i is an integer in the range of 0 to 100. In some embodiments, i is an integer in the range of 0 to 50, 0 to 30, 0 to 10, 0 to 5, or 0 to 3. In some embodiments, i is 0, 1, 2, 3, 4, 5, 6, 7, 8, 9, or 10.

In formula III-a and III-b, $A^0$ and $A^i$ are each independently selected from the group consisting of optionally substituted alkyl, optionally substituted alkenyl, optionally substituted heteroalkyl, optionally substituted amido, optionally substituted alkoxy, optionally substituted cabonyl, and optionally substituted carboxy.

In some embodiments, $A^0$ and $A^i$ are each independently unsubstituted alkyl or alkyl substituted by a moiety selected from the group consisting of: —NRR″, —OR, —COOR, —COR, —CONHR, —CONRR″, halo and —CN; wherein R is $C_1$-$C_{20}$ alkyl, and R″ is hydrogen or $C_1$-$C_{20}$ alkyl. In some embodiments, the optionally substituted alkyl may be optionally substituted $C_1$-$C_{40}$ alkyl. In some embodiments, $A^0$ and the $A^i$ are each independently $C_1$-$C_{40}$ alkyl or $C_1$-$C_{20}$ haloalkyl.

In some embodiments, $A^0$ and $A^i$ are each independently $C_1$-$C_{20}$ haloalkyl, $C_1$-$C_{40}$ arylalkyl, or $C_1$-$C_{20}$ alkenyl.

In formulae III-a and III-b, each $R^5$ is independently selected from the group consisting of optionally substituted alkoxy, optionally substituted aryloxy, optionally substituted acyloxy, and amino. In some embodiments, $R^5$ may attach to phenyl ring at ortho and/or para position. In some embodiments, $R^5$ may be alkoxy represented by the formula $OC_nH_{2n+1}$ where n=1-40. In some embodiments, $R^5$ may be aryloxy represented by the following formulae: ArO or O—CR—OAr where R is alkyl, substituted alkyl, aryl, or heteroaryl, and Ar is any substituted or unsubstituted aryl, or substituted or unsubstituted heteroaryl. In some embodiments, $R^5$ may be acyloxy represented by the formula $OCOC_nH_{2n+1}$ where n=1-40.

In formulae III-a and III-b, $A^2$ is selected from the group consisting of optionally substituted alkylene, optionally substituted alkenylene, optionally substituted arylene, optionally substituted heteroarylene, ketone, ester, and

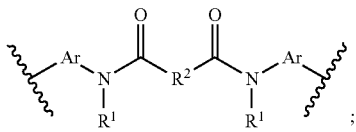

wherein Ar is optionally substituted aryl or optionally substituted heteroaryl, $R^1$ is selected from the group consisting of H, alkyl, alkenyl, aryl, heteroaryl, aralkyl, alkaryl; and $R^2$ is selected from the group consisting of optionally substituted alkylene, optionally substituted alkenylene, optionally substituted arylene, optionally substituted heteroarylene, ketone, and ester; or $R^1$ and $R^2$ may be connected together to form a ring.

In formulae III-a and III-b, $L^i$ is independently selected from the group consisting of optionally substituted alkylene, optionally substituted alkenylene, optionally substituted alkynylene, optionally substituted arylene, optionally substituted heteroarylene.

In some embodiments, at least one of the $L^i$ is selected from the group consisting of: 1,2-ethylene, acetylene, 1,4-phenylene, 1,1'-biphenyl-4,4'-diyl, naphthalene-2,6-diyl, naphthalene-1,4-diyl, 9H-fluorene-2,7-diyl, perylene-3,9-diyl, perylene-3,10-diyl, or pyrene-1,6-diyl, 1H-pyrrole-2,5-diyl, furan-2,5-diyl, thiophen-2,5-diyl, thieno[3,2-b]thiophene-2,5-diyl, benzo[c]thiophene-1,3-diyl, dibenzo[b,d]thiophene-2,8-diyl, 9H-carbozole-3,6-diyl, 9H-carbozole-2,7-diyl, dibenzo[b,d]furan-2,8-diyl, 10H-phenothiazine-3,7-diyl, and 10H-phenothiazine-2,8-diyl; wherein each moiety is optionally substituted.

Formula IV

Some embodiments provide a chromophore having the structure below:

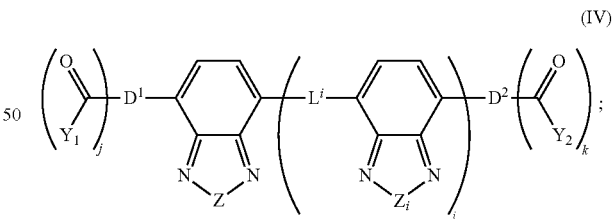

wherein i is an integer in the range of 0 to 100. In some embodiments, i is an integer in the range of 0 to 50, 0 to 30, 0 to 10, 0 to 5, or 0 to 3. In some embodiments, i is 0, 1, 2, 3, 4, 5, 6, 7, 8, 9, or 10.

In formula IV, Z and $Z_i$ are each independently selected from the group consisting of —O—, —S—, —Se—, —Te—, —$NR^6$—, —$CR^6$=$CR^6$—, and —$CR^6$=N—, wherein $R^6$ is hydrogen, optionally substitute $C_1$-$C_6$ alkyl, or optionally substituted $C_1$-$C_{10}$ aryl; and In formula IV, $D^1$ and $D^2$ are independently selected from the group consisting of optionally substituted alkoxy, optionally substituted aryloxy, optionally substituted acyloxy, optionally substituted alkyl, optionally substituted aryl, optionally substituted heteroaryl, optionally substituted amino, amido, cyclic amido, and cyclic imido; j is 0, 1 or 2, and k is 0, 1, or 2. In some embodiments, the —C(=O)Y$_1$ and —C(=O)Y$_2$ groups may attach to the substituent(s) of the optionally substituted moiety for D$^1$ and D$^2$.

In formula IV, Y$_1$ and Y$_2$ are independently selected from the group consisting of optionally substituted aryl, optionally substituted alkyl, optionally substituted cycloalkyl, optionally substituted alkoxy, and optionally substituted amino; and In formula IV, L$^i$ is independently selected from the group consisting of optionally substituted alkylene, optionally substituted alkenylene, optionally substituted alkynylene, optionally substituted arylene, optionally substituted heteroarylene.

In some embodiments, at least one of the L$^i$ is selected from the group consisting of: 1,2-ethylene, acetylene, 1,4-phenylene, 1,1'-biphenyl-4,4'-diyl, naphthalene-2,6-diyl, naphthalene-1,4-diyl, 9H-fluorene-2,7-diyl, perylene-3,9-diyl, perylene-3,10-diyl, or pyrene-1,6-diyl, 1H-pyrrole-2,5-diyl, furan-2,5-diyl, thiophen-2,5-diyl, thieno[3,2-b]thiophene-2,5-diyl, benzo[c]thiophene-1,3-diyl, dibenzo[b,d]thiophene-2,8-diyl, 9H-carbozole-3,6-diyl, 9H-carbozole-2,7-diyl, dibenzo[b,d]furan-2,8-diyl, 10H-phenothiazine-3,7-diyl, and 10H-phenothiazine-2,8-diyl; wherein each moiety is optionally substituted.

With regard to L$^i$ in any of the formulae above, the electron linker represents a conjugated electron system, which may be neutral or serve as an electron donor itself. In some embodiments, some examples are provided below, which may or may not contain additional attached substituents.

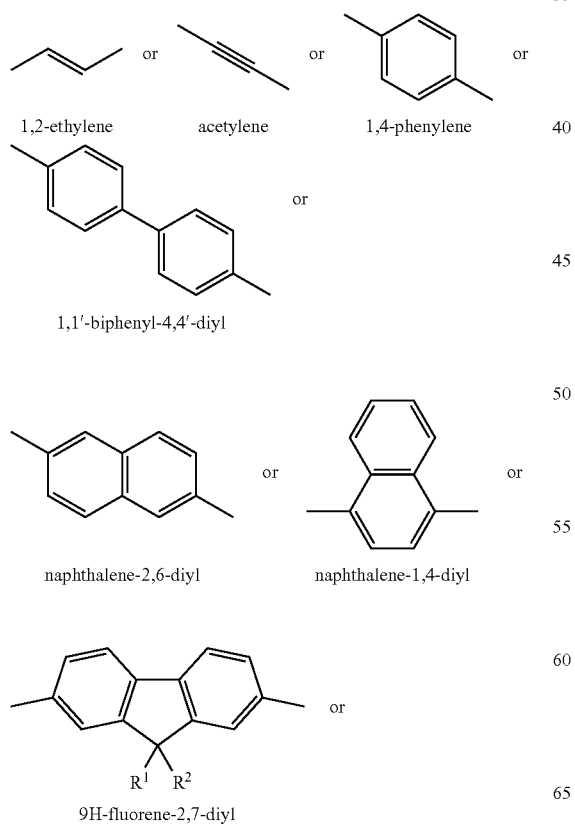

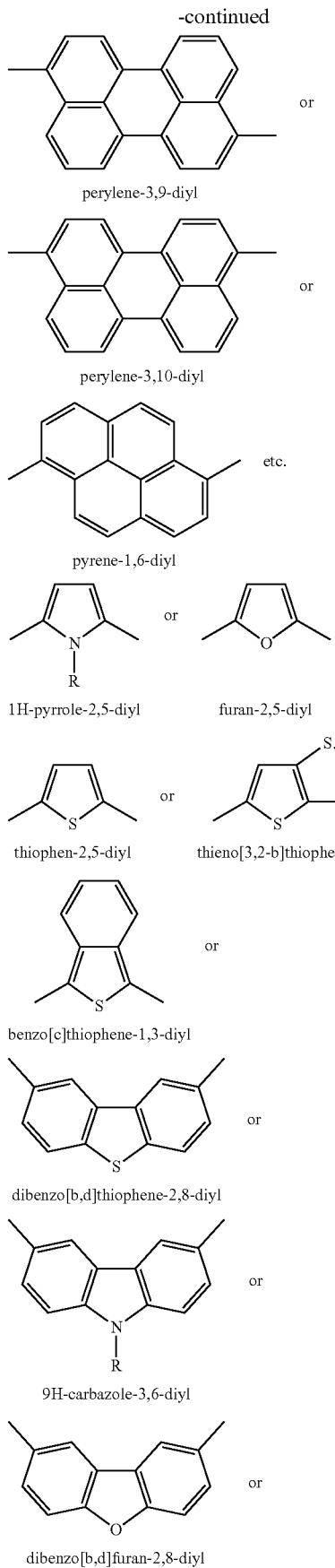

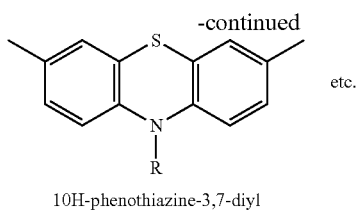

10H-phenothiazine-3,7-diyl

Wavelength Conversion Luminescent Medium

The chromophores disclosed herein are useful and may be suitable for providing a fluorescence film for use in improving long wavelength conversion efficiency and provide high fluorescence quantum efficiency. The chromophores can provide a wavelength conversion luminescent medium that provides excellent light conversion effects. The wavelength conversion luminescent medium receives as input at least one photon having a first wavelength, and provides as output at least one photon having a second wavelength which is longer (higher) than the first wavelength.

The wavelength conversion luminescent medium comprises an optically transparent polymer matrix and at least one organic luminescent dye comprising a chromophore disclosed herein. In some embodiments, the polymer matrix is form from a substance selected from the group consisting of polyethylene terephthalate, polymethyl methacrylate, polyvinyl butyral, ethylene vinyl acetate, ethylene tetrafluoroethylene, polyimide, amorphous polycarbonate, polystyrene, siloxane sol-gel, polyurethane, polyacrylate, and combinations thereof.

In some embodiments, the luminescent dye is present in the polymer matrix in an amount in the range of about 0.01 wt % to about 3 wt %, about 0.03 wt % to about 2 wt %, about 0.05 wt % to about 1 wt %, about 0.1 wt % to about 0.9 wt %, or about 0.2 wt % to about 0.7 wt %. In an embodiment of the medium, the luminescent dye is present in the polymer matrix in an amount of about 0.5 wt %.

In some embodiments, the refractive index of the polymer matrix material is in the range of about 1.4 to about 1.7, about 1.45 to about 1.65, or about 1.45 to about 1.55. In some embodiments, the refractive index of the polymer matrix material is about 1.5.

In some embodiments, a wavelength conversion luminescent medium is fabricated into a thin film structure by (i) preparing a polymer solution with dissolved polymer powder in a solvent such as tetrachloroethylene (TCE), cyclopentanone, dioxane, etc., at a predetermined ratio; (ii) preparing a luminescent dye containing a polymer mixture by mixing the polymer solution with the luminescent dye at a predetermined weight ratio to obtain a dye-containing polymer solution, (iii) forming a dye/polymer thin film by directly casting the dye-containing polymer solution onto a glass substrate, then heat treating the substrate from room temperature up to 100° C. in 2 hours, completely removing the remaining solvent by further vacuum heating at 130° C. overnight, and (iv) peeling off the dye/polymer thin film under the water and then drying out the free-standing polymer film before use; (v) the film thickness can be controlled by varying the dye/polymer solution concentration and evaporation speed.

The luminescent thin film thickness may vary over a wide range. In some embodiments, the luminescent thin film thickness is between about 0.1 m to about 1 mm, about 0.5 m to about 1 mm, or about 1 m to about 0.8 mm. In some embodiments, the luminescent thin film thickness is between about 5 m to about 0.5 mm.

Wavelength conversion mediums are useful in various applications, such as optical light collection systems, fluorescence-based solar collectors, fluorescence-activated displays, and single-molecule spectroscopy, to name a few. The use of the organic wavelength down-shifting luminescent medium as disclosed herein, significantly enhances the photoelectric conversion efficiency of photovoltaic devices or solar cells by greater than 0.5% when applied directly to the light incident surface of the device or encapsulated directly into the device during fabrication.

Photovoltaic Module and Method

Another aspect of the invention provides a photovoltaic module for the conversion of solar light energy into electricity, the photovoltaic module comprises at least one photovoltaic device or solar cell, and a wavelength conversion luminescent medium as described herein. The at least one photovoltaic device or solar cell is adapted to convert incident solar light energy into electricity. The wavelength conversion luminescent medium is positioned such that the incident light passes through the wavelength conversion luminescent medium prior to reaching the photovoltaic device or solar cell. The photovoltaic module utilizes the wavelength conversion luminescent medium to enhance the photoelectric conversion efficiency of a photovoltaic device.

Many of these photovoltaic devices or solar cells utilize materials on the light incident side of the device which absorb certain wavelengths of the solar spectrum, typically the shorter ultra violet (UV) wavelengths, instead of allowing the light to pass through to the photoconductive material of the device. This UV absorption effectively reduces the efficiency of the device. The use of a down-shifting medium in these photovoltaic devices and solar cells, when applied to the light incident side of the device, causes the shorter wavelength light to become excited and re-emitted from the medium at a longer (higher) more favorable wavelength, which can then be utilized by the photovoltaic device or solar cell, effectively enhancing the photoelectric conversion efficiency by allowing a wider spectrum of solar energy to be converted into electricity.

The use of luminescent down-shifting materials to improve the efficiency of photovoltaic devices and solar cells has been disclosed in several publications, including U.S. Pat. No. 7,791,157, and U.S. Patent Application Publication Nos. 2009/0151785, 2010/0294339, and 2010/0012183. All of these publications include example embodiments of luminescent down-shifting mediums applied to a photovoltaic device or solar cell in which the medium is composed of an inorganic material. Advantageously, the use of an organic medium, instead of an inorganic medium, to enhance the efficiency of photovoltaic devices or solar cells has the potential to significantly lower the device cost as these organic materials are much cheaper to synthesize and apply.

Another aspect of the disclosure is a method for improving the performance of a photovoltaic device or solar cell comprising applying a wavelength conversion luminescent medium directly onto the light incident side of the solar cell or photovoltaic device.

Yet another aspect of the disclosure provides a method for improving the performance of a photovoltaic device or solar cell, comprising incorporating a wavelength conversion luminescent medium directly into the photovoltaic device or solar cell during its fabrication, such that the luminescent medium is encapsulated between the photovoltaic device or solar cell and a cover substrate on the light incident side.

In some embodiments, the luminescent film 100 is directly attached onto the light incident surface 102 of a solar cell 103, as shown in FIG. 1. FIG. 1 illustrates a photovoltaic device or solar cell in which a thin film wavelength conversion luminescent medium 100 is directly attached to the light incident surface of the device 102. A refractive index matching liquid or optical adhesive 101 is applied between the luminescent film and the light incident surface of the solar cell 103 to ensure better light out-coupling efficiency.

In some embodiments, a refractive index matching liquid or optical adhesive 101 is applied between the luminescent film and the front substrate of the solar cell to ensure better light out-coupling efficiency.

Figure 2:
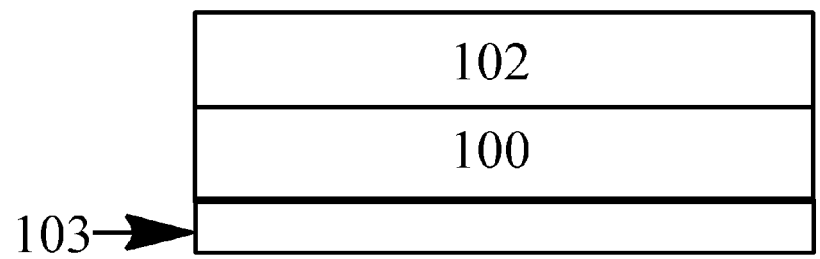
FIG. 2 illustrates a photovoltaic device or solar cell in which a thin film wavelength conversion luminescent medium is fabricated directly into the module as the encapsulation layer between the optically transparent light incident surface of the module and the photovoltaic device or solar cell.

In some embodiments, the luminescent film 100 is directly applied as the encapsulation layer during solar cell fabrication, as shown in FIG. 2. The luminescent film 100 is encapsulated between the solar cell module 103 and its front cover substrate 102. FIG. 2 illustrates a photovoltaic device or solar cell in which a thin film wavelength conversion luminescent medium 100 is fabricated directly into the module as the encapsulation layer between the optically transparent light incident surface of the module 102 and the photovoltaic device or solar cell 103.

In some embodiments, the solar cell is a CdS/CdTe solar cell. In another embodiment the solar cell is a CIGS solar cell. In an embodiment the solar cell is selected from the group consisting of an amorphous Silicon solar cell, a microcrystalline Silicon solar cell, or a crystalline Silicon solar cell.

In some embodiments, the solar cell efficiency is measured with and without the thin film organic down-shifting luminescent medium under one sun irradiation (AM1.5G) by using a Newport solar simulator system. The efficiency enhancement of the solar cell with the luminescent medium is determined by the equation below:

Efficiency Enhancement=$(\eta_{cell+luminescent\ film}-\eta_{cell})/\eta_{cell}*100\%$ In some embodiments, a crystalline Silicon solar cell is modified with a wavelength conversion luminescent medium according to the method disclosed herein, and the efficiency enhancement is determined to be greater than 0.2%. In an embodiment, the efficiency enhancement is determined to be greater than 0.4%. In an embodiment, the efficiency enhancement is determined to be greater than 0.5%. In an embodiment, the efficiency enhancement is determined to be greater than 0.8%. In an embodiment, the efficiency enhancement is determined to be greater than 1.0%.

In some embodiments, a CdS/CdTe solar cell with an efficiency $\eta_{cell}$ of 11.3%, which is similar to the efficiency level achieved in most commercially available CdS/CdTe cells, is modified with a wavelength conversion luminescent medium according to the method disclosed herein, and the efficiency enhancement is determined to be greater than about 2%. In an embodiment, the efficiency enhancement is determined to be greater than about 6%. In an embodiment, the efficiency enhancement is determined to be greater than about 10%. In an embodiment, the efficiency enhancement is determined to be greater than about 12%. In an embodiment, the efficiency enhancement is determined to be greater than about 14%.

In some embodiments, a CIGS solar cell with an efficiency □cell of 14.0%, which is slightly higher than the efficiency level achieved in most commercially available CIGS cells, is modified with a wavelength conversion luminescent medium according to the method disclosed herein, and the efficiency enhancement is determined to be greater than about 6%. In an embodiment, the efficiency enhancement is determined to be greater than about 7%. In an embodiment, the efficiency enhancement is determined to be greater than about 10%. In an embodiment, the efficiency enhancement is determined to be greater than about 11%.

In some embodiments, a photovoltaic device or solar cell comprises at least one device selected from the group consisting of a Cadmium Sulfide/Cadmium Telluride solar cell, a Copper Indium Gallium Diselenide solar cell, an amorphous Silicon solar cell, a microcrystalline Silicon solar cell, or a crystalline Silicon solar cell.

For purposes of summarizing aspects of the invention and the advantages achieved over the related art, certain objects and advantages of the invention are described in this disclosure. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the examples which follow.

EXAMPLES

The embodiments will be explained with respect to preferred embodiments which are not intended to limit the present invention. In the present disclosure, the listed substituent groups include both further substituted and unsubstituted groups unless specified otherwise. Further, in the present disclosure where conditions and/or structures are not specified, the skilled artisan in the art can readily provide such conditions and/or structures, in view of the present disclosure, as a matter of routine experimentation guided by the present disclosure.

For each example compound, the maximum absorption and fluorescence emission wavelength were measured in a solution and/or in a polyvinylbutyral (PVB) film. For example, in a dichloromethane solution of the obtained chromophore Example 1 (4,7-bis(4-(N,N-diphenylamino)phenyl)-2-(pyridin-4-yl)-2H-benzo[d][1,2,3]triazole), the maximum absorption of the chromophore was 451 nm and the maximum fluorescence absorption was 593 nm upon 470 nm light illumination. For example, in a dichloromethane (DCM) solution comprising chromophore Example 48, the maximum absorption of the chromophore was 448 nm and the maximum fluorescence emission was 618 nm upon 470 nm light illumination. In a PVB film (having 0.3 wt % chromophore) comprising chromophore Example 48, the maximum absorption of the chromophore was 456 nm and the maximum fluorescence emission was 562 nm upon 470 nm light illumination. The wavelength differences between maximum absorption and maximum fluorescence is an improved property that is useful for new optical light collection systems and fluorescence-based solar collectors.

Additionally, Examples 1-32 compounds are based on the structure of formula (I-a) and (I-b). Examples 33-41 compounds are based on the structure of formula (II-a) and (II-b). Examples 42-47 compounds are based on the structure of formula (III-a) and (III-b). Examples 48-59 are based on the structure of formula (IV-a).

Example Synthesis and Spectral Data

Intermediate A

Common Intermediate A is synthesized using a two step procedure.

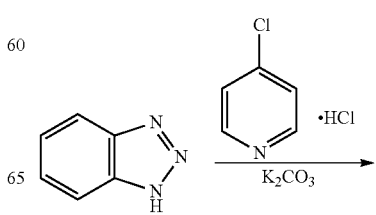

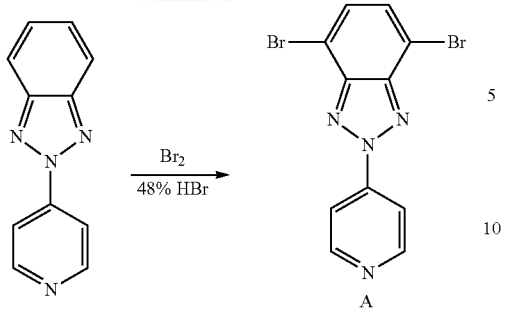
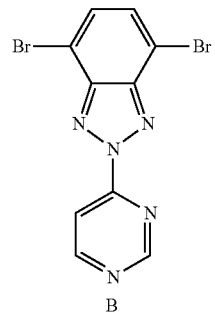

Step 1: Synthesis of 2-(Pyridin-4-yl)-2H-benzo[d][1,2,3]triazole

A mixture of 4-chloropyridinium hydrochloride (25.0 g, 166 mmol), benzotriazole (29.6 g, 249 mmol), potassium carbonate (69.1 g, 500 mmol), and dimethylformamide (500 mL) was stirred and heated under argon at 130° C. for 3 days. After cooling, the solid was filtered off, and the solvent was evaporated under reduced pressure. The residue was treated with dichloromethane (200 mL), filtered and chromatographed using a column filled with silica gel (500 mL) and hexane/ethyl acetate (1:1) as an eluent. Fractions containing the desired product were combined, and the solvent was distilled off. The residue was triturated with ethanol, the solid was filtered off and dried in a vacuum oven to give 2-(pyridin-4-yl)-2H-benzo[d][1,2,3]triazole, 6.45 (20%). 1H NMR (400 MHz, CDCl$_3$): δ 8.80 (m, 2H, pyridine), 8.26 (m, 2H, pyridine), 7.93 (m, 2H, benzotriazole), 7.46 (m, 2H, benzotriazole).

Step 2: Synthesis of Intermediate A—4,7-Dibromo-2-(pyridin-4-yl)-2H-benzo[d][1,2,3]triazole)

A mixture of 2-(pyridin-4-yl)-2H-benzo[d][1,2,3]triazole (6.42 g, 32.7 mmol), bromine (5.20 mL, 100 mmol) and 48% HBr (50 mL) was heated at 120° C. for 40 hours. The reaction mixture was poured into ice/water (500 mL), treated with 5N NaOH to pH 8, and the excess of bromine was removed by addition of 1M sodium thiosulfate (test with KI/starch paper). After stirring for 30 min, the solid was filtered off, washed with water and dried in a vacuum oven. The crude product was purified by column chromatography (silica gel, dichloromethane/ethyl acetate 9:1) and washing with ethyl acetate (50 mL) to give 4,7-dibromo-2-(pyridin-4-yl)-2H-benzo[d][1,2,3]triazole (Intermediate A) 5.00 g (43%). $^1$H NMR (400 MHz, CDCl$_3$): δ 8.85 (m, 2H, pyridine), 8.33 (m, 2H, pyridine), 7.53 (s, 2H, benzotriazole).

Intermediate B

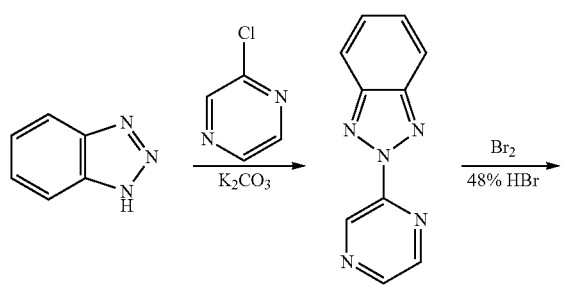

A similar two-step procedure as that of Intermediate A was applied to give 2-(pyrazin-2-yl)-2H-benzo[d][1,2,3]triazole (23% yield) in the first step and 4,7-dibromo-2-(pyrazin-2-yl)-2H-benzo[d][1,2,3]triazole (Intermediate B, 26%) in the second step. $^1$H NMR (400 MHz, CDCl$_3$): δ 9.75 (d, J=1.5 Hz, 1H, pyrazine), 8.81 (d, J=2.2 Hz, 1H, pyrazine), 8.71 (dd, J=2.5 and 1.5 Hz, 1H, pyrazine), 7.56 (s, 2H, benzotriazole).

Intermediate C

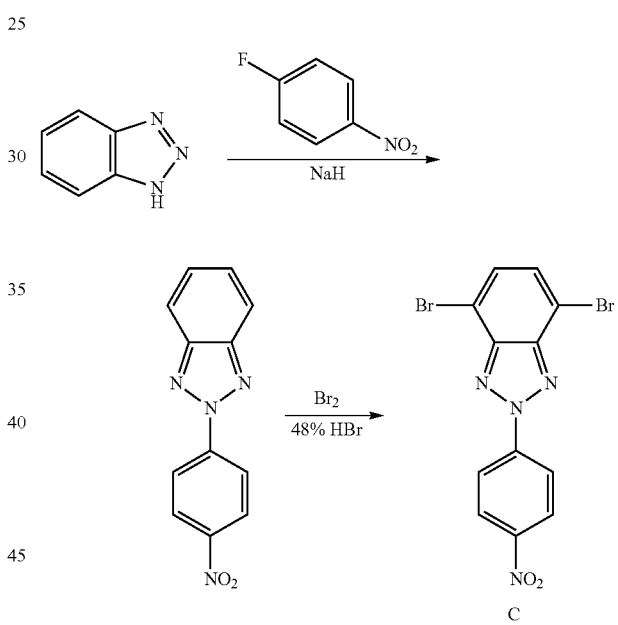

A similar two-step procedure as that of Intermediate A was applied to give 2-(4-nitrophenyl)-2H-benzo[d][1,2,3]triazole (16% yield) in the first step and 4,7-dibromo-2-(4-nitrophenyl)-2H-benzo[d][1,2,3]triazole (Intermediate C, 75%) in the second step. $^1$H NMR (400 MHz, CDCl$_3$): δ 8.65 (m, 2H, 4-nitrophenyl), 8.44 (m, 2H, 4-nitrophenyl), 7.54 (s, 2H, benzotriazole).

Intermediate D

Common Intermediate D is synthesized in a two step process.

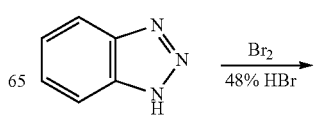

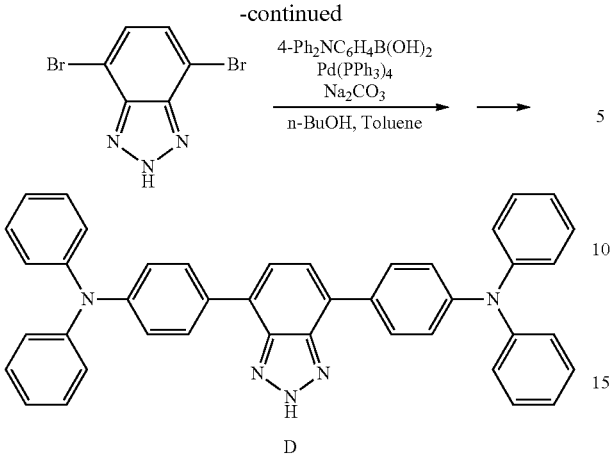

Step 1: Synthesis of 4,7-Dibromo-2H-benzo[d][1,2,3]triazole

A mixture of benzotriazole (5.96 g, 50 mmol), bromine (7.7 mL, 150 mmol) and 48% HBr (30 mL) was heated at 120° C. for 24 hours. The reaction mixture was poured into ice/water (200 mL), neutralized with 5N NaOH, and the excess of bromine was removed by addition of 1M sodium thiosulfate (test with KI/starch paper). After stirring for 30 minutes, the solid was filtered off, washed with water and dried in a vacuum oven. The crude product was purified by column chromatography (silica gel, dichloromethane/ethyl acetate 75:25) and washing with ethyl acetate (50 mL) to 4,7-dibromo-2H-benzo[d][1,2,3]triazole 2.65 g (19%).

Step 2: Synthesis of Intermediate D-4,7-Bis(4-(N,N-diphenylamino)phenyl)-2H-benzo[d][1,2,3]triazole A mixture of 4,7-dibromo-2H-benzo[d][1,2,3]triazole (1.37 g, 5.5 mmol), 4-(diphenylamino)phenylboronic acid (3.47 g, 12 mmol), sodium carbonate (5.30 g, 50 mmol) in water (10 mL), tetrakis(triphenylphosphine)palladium (0) (1.15 g, 1.0 mmol), n-butanol (80 mL), and toluene (10 mL) was stirred and heated under argon at 120° C. for 4 days. The reaction mixture was poured into water (300 mL), stirred for 15 minutes, and extracted with dichloromethane (2×300 mL). The solution was dried over anhydrous sodium sulfate, the solvent was removed under reduced pressure, and the residue was chromatographed (silica gel, dichloromethane/ethyl acetate 95:5) to give 4,7-bis(4-(N,N-diphenylamino)phenyl)-2H-benzo[d][1,2,3]triazole (Intermediate D), 1.85 g (56%). $^1$H NMR (400 MHz, CDCl$_3$): δ 7.58 (s, 2H, benzotriazole), 7.16-7.23 (m, 16H, p-phenylene and Ph), 7.07 (t, J=7.3, 4H, Ph), 7.02 (bs, 1H, N—H).

Intermediates E and F

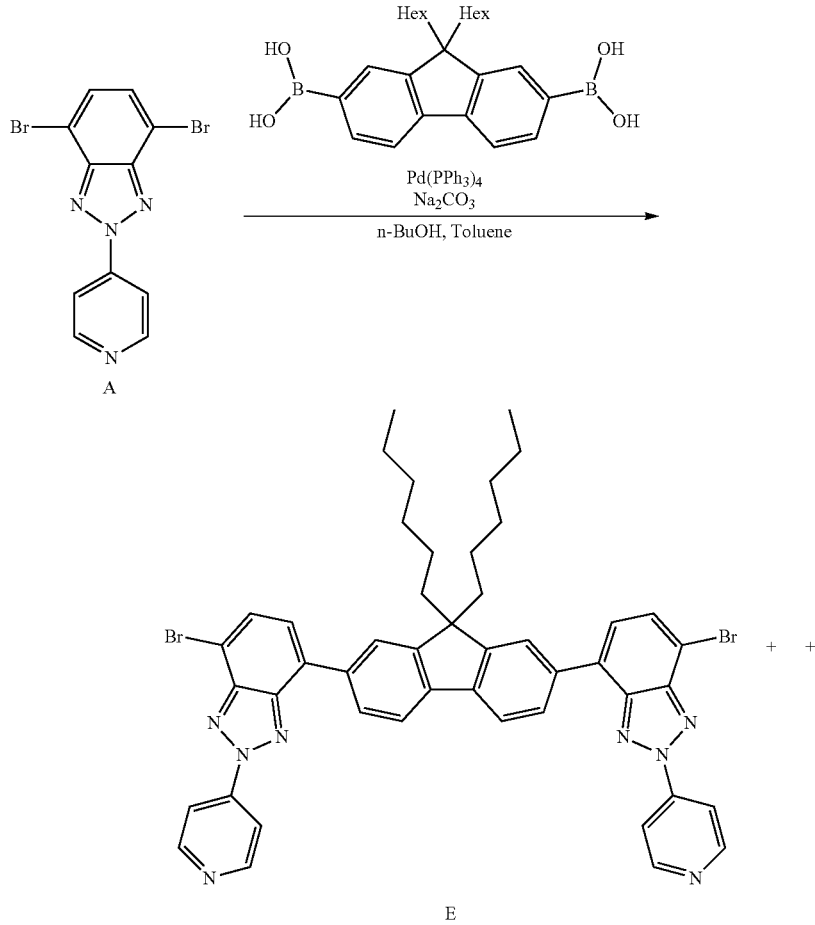

-continued

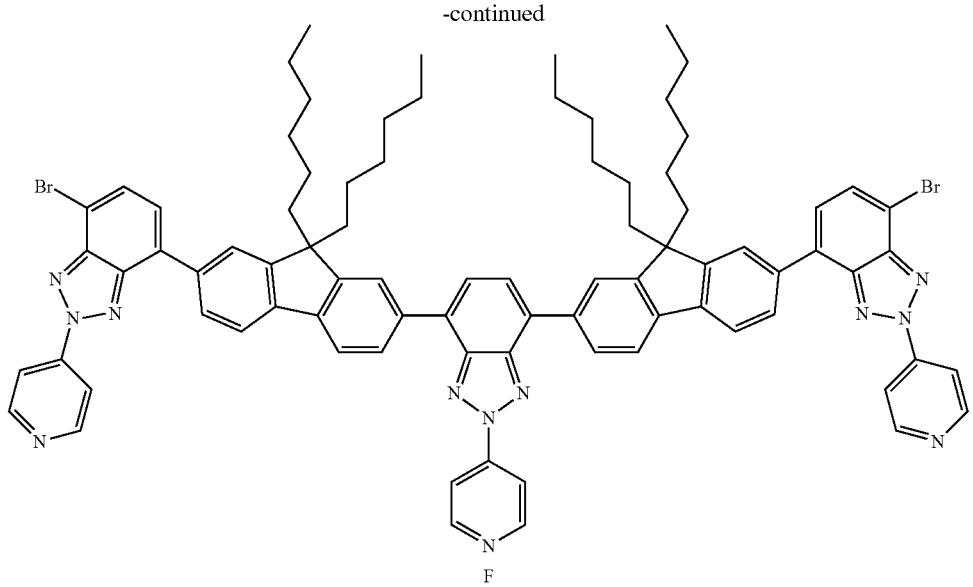

F

A mixture of Intermediate A (90%, 13.77 g, 35 mmol), 9,9-dihexylfluorene-2,7-diboronic acid (5.06 g, 12 mmol), sodium carbonate (4.24 g, 40 mmol) in water (25 mL), tetrakis(triphenylphosphine)palladium (0) (2.00 g, 1.72 mmol), n-butanol (60 mL), and toluene (80 mL) was stirred and heated under argon at 110° C. for 48 hours. The reaction mixture was poured into water (300 mL), treated with 5N NaOH (30 mL), stirred for 1 hour, and extracted with dichloromethane (4×400 mL). The volatiles were removed under reduced pressure, and the residue was chromatographed (silica gel, dichloromethane/tetrahydrofuran 9:1). The first fraction gave recovered starting material Intermediate A (5.00 g, 36%).

The material from the second fraction was washed with acetone (20 mL) and dried in a vacuum oven to give 2,7-bis (7-bromo-2-(pyridin-4-yl)-2H-benzo[d][1,2,3]triazol-4-yl)-9,9-dihexylfluorene (Intermediate E), yellow crystals, 4.52 g (purity 90%, yield 39%). $^1$H NMR (400 MHz, CDCl$_3$): δ 8.84 (m, 4H, pyridine), 8.36 (m, 4H, pyridine), 8.10 (s, 2H, fluorene), 8.06 (d, 2H, benzotriazole), 7.93 (d, J=8.0 Hz, 2H, benzotriazole), 7.77 (d, J=7.7 Hz, 2H, fluorene), 7.59 (d, J=7.7 Hz, 2H, fluorene), 2.15 (m, 4H, hexyl), 1.13-1.15 (m, 12H, hexyl), 0.89 (m, 4H, hexyl), 0.72 (t, J=6.6 Hz, 6H, hexyl).

The third fraction gave Intermediate F, yellow crystals, 1.65 g (purity 80%, yield 39%). $^1$H NMR (400 MHz, CDCl$_3$): δ 8.84 (m, 4H, pyridine), 8.36 (m, 4H, pyridine), 8.10 (s, 2H, fluorene), 8.06 (d, 2H, benzotriazole), 7.93 (d, J=8.0 Hz, 2H, benzotriazole), 7.77 (d, J=7.7 Hz, 2H, fluorene), 7.59 (d, J=7.7 Hz, 2H, fluorene), 2.15 (m, 4H, hexyl), 1.13-1.15 (m, 12H, hexyl), 0.89 (m, 4H, hexyl), 0.72 (t, J=6.6 Hz, 6H, hexyl).

Intermediate G

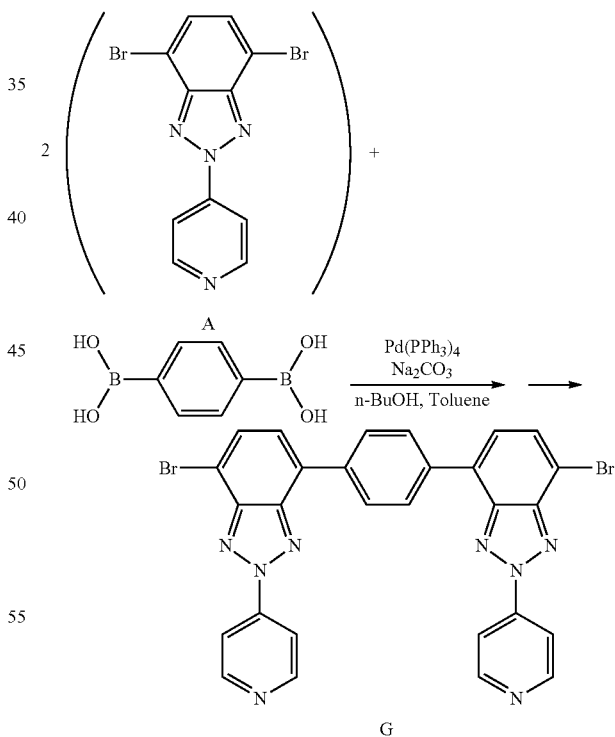

G

A mixture of Intermediate A (90%, 2.40 g, 6.14 mmol), 1,4-benzenediboronic acid (248 mg, 1.5 mmol), sodium carbonate (530 g, 5 mmol) in water (4 mL), tetrakis(triphenylphosphine)palladium (0) (500 mg, 0.43 mmol), n-butanol (20 mL), and toluene (20 mL) was stirred and heated under argon at 110° C. for 68 hours. The reaction mixture was poured into water (300 mL), treated with 5N NaOH (50 mL), stirred for 1 hour, and extracted with dichloromethane (3×200 mL, low solubility in dichloromethane). The volatiles were removed under reduced pressure, and the residue was chromatographed (silica gel, chloroform/tetrahydrofuran 9:1). The obtained product was triturated with ethyl acetate (30 mL), filtered off and dried in a vacuum oven to give 1,4-bis (7-bromo-2-(pyridin-4-yl)-2H-benzo[d][1,2,3]triazol-4-yl) benzene (Intermediate G), yellow crystals, 610 mg (purity 80%, yield 65%). $^1$H NMR (400 MHz, CDCl$_3$): δ 8.86 (m, 4H, pyridine), 8.39 (m, 4H, pyridine), 8.26 (s, 4H, benzotriazole), 7.79 (d, J=7.7 Hz, 2H, benzene), 7.62 (d, J=7.7 Hz, 2H, benzene).

Example 1

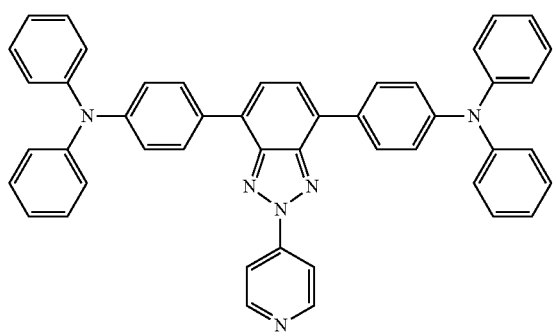

A mixture of Intermediate A (purity 90%, 1.95 g, 5 mmol), sodium carbonate (2.69 g, 25 mmol), 4-(diphenylamino)phenylboronic acid (3.47 g, 12 mmol), tetrakis(triphenylphosphine)palladium (0) (0.58 g, 0.5 mmol), water (20 mL), dioxane (80 mL), and toluene (10 mL) was heated under argon at 110° C. for 48 hours. The reaction mixture was poured into water (200 mL), diluted with dichloromethane (200 mL), treated with 2N NaOH (50 mL), stirred for 1 hour, and the dichloromethane layer was separated. The aqueous phase was washed with dichloromethane (200 mL). Both dichloromethane solutions were combined, dried over anhydrous sodium sulfate, and the solvent was removed under reduced pressure. The crude product was purified by column chromatography and recrystallization from ethyl acetate/ethanol (1:1) to give 4,7-bis(4-(N,N-diphenylamino)phenyl)-2-(pyridin-4-yl)-2H-benzo[d][1,2,3]triazole (Example 1), orange crystals, 1.71 g (50%). $^1$H NMR (400 MHz, CDCl$_3$): δ 8.80 (m, 2H, pyridine), 8.34 (m, 2H, pyridine), 8.06 (d, J=8.7 Hz, 4H, p-phenylene), 7.67 (s, 2H, benzotriazole), 7.31 (m, 8H, Ph), 7.21 (m, 12H, p-phenylene and Ph), 7.08 (tt, J=7.3 and 2.2 Hz, 4H, Ph). UV-vis spectrum (dichloromethane): $\lambda_{max}$=451 nm. Fluorimetry (dichloromethane): $\lambda_{max}$=593 nm.

Example 2

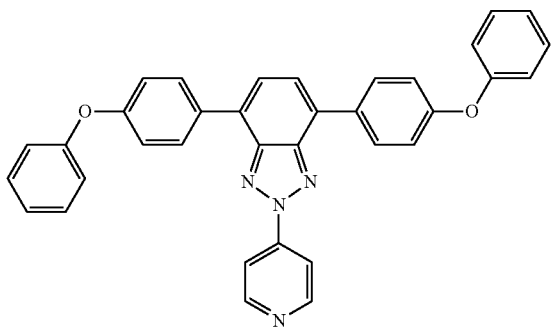

A mixture of Intermediate A (704 mg, 2 mmol), 4-phenoxyphenylboronic acid (2.14 g, 10 mmol), tetrakis(triphenylphosphine)palladium (0) (0.50 g, 0.43 mmol), sodium carbonate (2.12 g, 20 mmol) in water (8 mL), n-butanol (20 mL), toluene (20 mL), and acetone (5 mL) is heated under argon at 110° C. for 16 hours. The reaction mixture is poured into water (100 mL), diluted with dichloromethane (100 mL), stirred for 1 hour, and the dichloromethane layer is separated. The aqueous phase is washed with dichloromethane (100 mL). Both dichloromethane solutions are combined, dried over anhydrous sodium sulfate, and the solvent is removed under reduced pressure. The crude product is purified by column chromatography (silica gel, dichloromethane/ethyl acetate 9:1) and recrystallization from ethyl acetate to give 4,7-bis(4-phenoxyphenyl)-2-(pyridin-4-yl)-2H-benzo[d][1,2,3]triazole (Example 2), yellow-green crystals, 865 mg (81%). $^1$H NMR (400 MHz, CDCl$_3$): δ 8.82 (m, 2H, pyridine), 8.35 (m, 2H, pyridine), 8.12 (d, J=8.7 Hz, 4H, p-phenylene), 7.69 (s, 2H, benzotriazole), 7.40 (m, 4H, Ph), 7.18 (d, J=8.7 Hz, 4H, p-phenylene), 7.17 (m, 2H, Ph), 7.13 (m, 4H, Ph). UV-vis spectrum (dichloromethane): $\lambda_{max}$=386 nm. Fluorimetry (dichloromethane): $\lambda_{max}$=499 nm.

Example 3

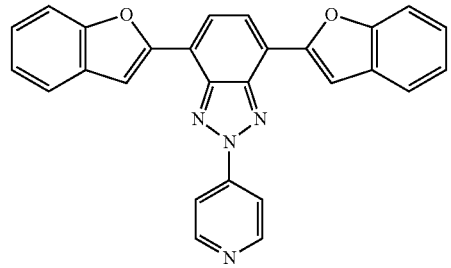

A mixture of Intermediate A (1.41 g, 4 mmol), benzofuran-2-ylboronic acid (1.60 g, 9.8 mmol), tetrakis(triphenylphosphine)palladium (0) (0.50 g, 0.43 mmol), sodium carbonate (2.12 g, 20 mmol) in water (10 mL), n-butanol (25 mL), and toluene (25 mL) is heated under argon at 110° C. for 3 days. The reaction mixture is poured into water (200 mL), diluted with dichloromethane (100 mL), and stirred for 1 hour. The solid is filtered off, washed with water (50 mL) followed by dichloromethane (20 mL) and dried to give 4,7-di(benzofuran-2-yl)-2-(pyridin-4-yl)-2H-benzo[d][1,2,3]triazole (Example 3), yellow crystals, 745 mg (43%). $^1$H NMR (400 MHz, CDCl$_3$): δ 8.92 (m, 2H, pyridine), 8.47 (m, 2H, pyridine), 8.16 (s, 2H, benzotriazole), 8.01 (s, 2H, benzofuran), 7.74 (d, J=7.4 Hz, 2H, benzofuran), 7.59 (d, J=7.4 Hz, 2H, benzofuran), 7.37 (td, J=7.7 and 1.1 Hz, 2H, benzofuran), 7.30 (td, J=7.5 and 1.1 Hz, 2H, benzofuran). UV-vis spectrum (dichloromethane): $\lambda_{max}$=436 nm. Fluorimetry (dichloromethane): $\lambda_{max}$=481 nm.

Examples 4, 5, and 6

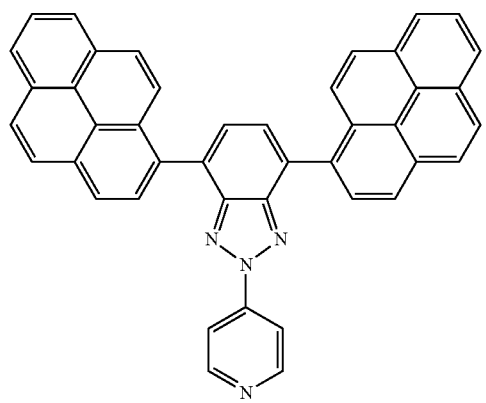

4

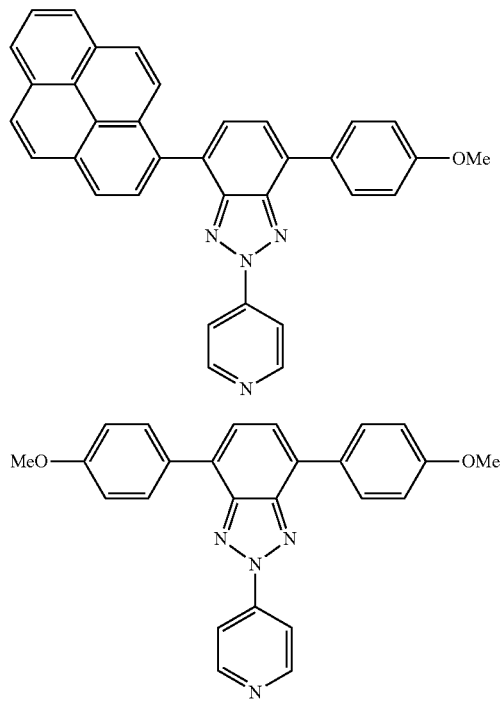

5

6

A mixture of Intermediate A (1.41 g, 4 mmol), pyrene-1-boronic acid (1.23 g, 5.0 mmol), 4-methoxyphenylboronic acid (0.76 g, 5.0 mmol), sodium carbonate (2.12 g, 20 mmol) in water (10 mL), tetrakis(triphenylphosphine)palladium (0) (0.50 g, 0.43 mmol), n-butanol (30 mL), and toluene (20 mL) was heated under argon at 110° C. for 4 hours. Thin layer chromatography (TLC) of the reaction mixture indicated no starting material left. The reaction mixture was poured into water (200 mL) and extracted with dichloromethane (3×200 mL). The extract was dried over anhydrous sodium carbonate, and the volatiles were removed under reduced pressure. The residue was chromatographed (silica gel, dichloromethane/ethyl acetate 95:5). The first fraction gave 4,7-di(pyren-1-yl)-2-(pyridin-4-yl)-2H-benzo[d][1,2,3]triazole (Example 4) (610 mg, 25%) as orange crystals. $^1$H NMR (400 MHz, CDCl$_3$): δ 8.60 (m, 2H, pyridine), 8.38 (m, 4H, pyrene), 8.22-8.29 (m, 6H, pyrene), 8.20 (m, 4H, pyrene), 8.05-8.10 (m, 6H, pyrene and pyridine), 7.90 (s, 2H, benzotriazole). UV-vis spectrum (dichloromethane): $\lambda_{max}$=381 nm. Fluorimetry (dichloromethane): $\lambda_{max}$=524 nm.

The second fraction gave 4-(4-methoxyphenyl)-7-(pyren-1-yl)-2-(pyridin-4-yl)-2H-benzo[d][1,2,3]triazole (Example 5) (980 mg, 49%) as orange-yellow crystals. $^1$H NMR (400 MHz, CDCl$_3$): δ 8.70 (m, 2H, pyridine), 8.32 (d, J=7.7 Hz, 1H, pyrene), 8.12-8.27 (m, 10H, pyrene, 4-methoxyphenyl, and pyridine), 8.02 (m, 2H, pyrene), 7.79 (d, J=7.3 Hz, 1H, benzotriazole), 7.73 (d, J=7.4 Hz, 1H, benzotriazole), 7.15 (d, J=8.8 Hz, 2H, 4-methoxyphenyl), 3.95 (s, 3H, methoxy). UV-vis spectrum (dichloromethane): $\lambda_{max}$=386 nm. Fluorimetry (dichloromethane): $\lambda_{max}$=527 nm.

The third fraction gave 4,7-bis(4-methoxyphenyl)-2-(pyridin-4-yl)-2H-benzo[d][1,2,3]triazole (Example 6) (160 mg, 10%) as yellow crystals. $^1$H NMR (400 MHz, CDCl$_3$): δ 8.81 (m, 2H, pyridine), 8.35 (m, 2H, pyridine), 8.08 (d, J=9.0 Hz, 2H, 4-methoxyphenyl), 7.64 (s, 2H, benzotriazole), 7.09 (d, J=9.0 Hz, 2H, 4-methoxyphenyl), 3.91 (s, 3H, methoxy). UV-vis spectrum (dichloromethane): $\lambda_{max}$=394 nm. Fluorimetry (dichloromethane): $\lambda_{max}$=512 nm.

Example 7

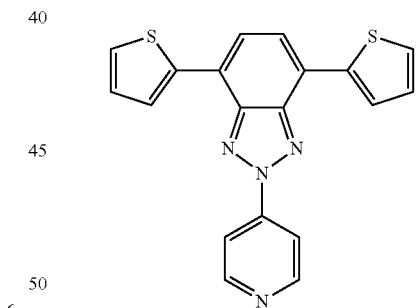

7

A mixture of intermediate A (1.60 g, 4 mmol), 2-thienylboronic acid (2.56 g, 20 mmol), tetrakis(triphenylphosphine) palladium (0) (0.84 g, 0.73 mmol), sodium carbonate (5.30 g, 50 mmol) in water (20 mL), and dimethoxyethane (80 mL) was heated under argon at 100° C. for 3 days. The reaction mixture was poured into water (150 mL), treated with 2N NaOH to pH 13, stirred for 30 minutes, and extracted with dichloromethane (3×100 mL). The extract was dried over anhydrous sodium sulfate, the volatiles were removed under reduced pressure, and the residue was chromatographed (silica gel, dichloromethane/ethyl acetate 95:5) to give 2-(pyridin-4-yl)-4,7-di(thiophen-2-yl)-2H-benzo[d][1,2,3]triazole (Example 7) as yellow crystals, 360 mg (22%). 1H NMR (400 MHz, CDCl$_3$): δ 8.85 (m, 2H, pyridine), 8.39 (m, 2H, pyridine), 8.17 (d, J=3.7 Hz, 2H, thiophene), 7.70 (s, 2H, benzotriazole), 7.43 (dd, J=5.1 and 1.1 Hz, 2H, thiophene), 7.22 (dd, J=5.1 and 3.6 Hz, 2H, thiophene). UV-vis spectrum (dichloromethane): $\lambda_{max}$=420 nm. Fluorimetry (dichloromethane): $\lambda_{max}$=522 nm.

Example 8

Example 8 is synthesized in a two step process.

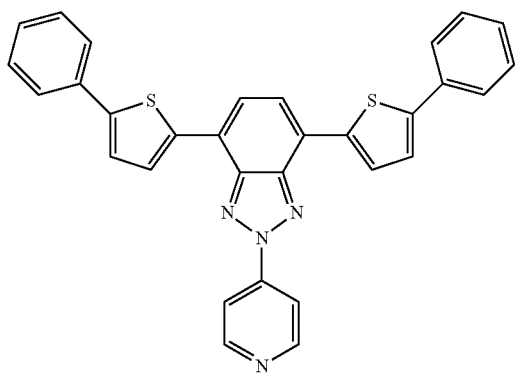

Step 1: Synthesis of tributyl(5-phenylthiophen-2-yl)stannane 2.5M n-BuLi in hexane (16 mL, 40 mmol) was added in small portions to a solution of 2-phenylthiophene (5.00 g, 31 mmol) and tetramethylethylenediamine (6.0 mL, 40 mmol) in tetrahydrofuran (50 mL) stirred under argon and cooled in a dry ice/acetone bath. The reaction mixture was heated to 30° C., stirred at this temperature for 1 hour, and cooled back in the dry ice/acetone bath. Tributylstannyl chloride (9.49 mL), 35 mmol was then added, the mixture was allowed to warm up, and it was left at room temperature for 20 hours. The volatiles were removed under reduced pressure. The residue was diluted with hexane (100 mL), filtered, and chromatographed using a column filled with silica gel (500 mL) washed with 2% triethylamine in hexane (500 mL) to give tributyl(5-phenylthiophen-2-yl)stannate (10.26 g) of purity 80%. Yield: 59%.

Step 2: Synthesis of Example 8-4,7-Bis(5-phenylthiophen-2-yl)-2-(pyridin-4-yl)-2H-benzo[d][1,2,3] triazole A mixture of Intermediate A (1.41 g, 4.0 mmol), 80% tributyl(5-phenylthiophen-2-yl)stannate (6.74 g, 12 mmol), bis(triphenylphosphine)palladium(II) dichloride (0.55 g, 0.78 mmol), and anhydrous dimethylformamide (20 mL) was stirred under argon and heated at 75° C. for 20 hours. The reaction mixture was poured into water (100 mL), diluted with dichloromethane (200 mL), treated with 5N NaOH to pH 14, stirred for 1 hour, and extracted with dichloromethane (2 x 400 mL, low solubility). The volatiles were removed under reduced pressure, and the crude product was purified by column chromatography (silica gel, dichloromethane/ethyl acetate 9:1) and washing with ethyl acetate (150 mL) to give 4,7-bis(5-phenylthiophen-2-yl)-2-(pyridin-4-yl)-2H-benzo[d][1,2,3]triazole (Example 8) as red crystals, 1.78 g (87%). $^1$H NMR (400 MHz, CDCl$_3$): δ 8.87 (m, 2H, pyridine), 8.39 (m, 2H, pyridine), 8.14 (d, J=4.0 Hz, 2H, thiophene), 7.70 (d, J=7.3 Hz, 4H, Ph), 7.67 (s, 2H, benzotriazole), 7.41-7.45 (m, 6H, Ph and thiophene), 7.33 (t, J=7.3 Hz, 2H, Ph). UV-vis spectrum (dichloromethane): $\lambda_{max}$=468 nm. Fluorimetry (dichloromethane): $\lambda_{max}$=564 nm.

Example 9

Example 9 is synthesized in a two step process.

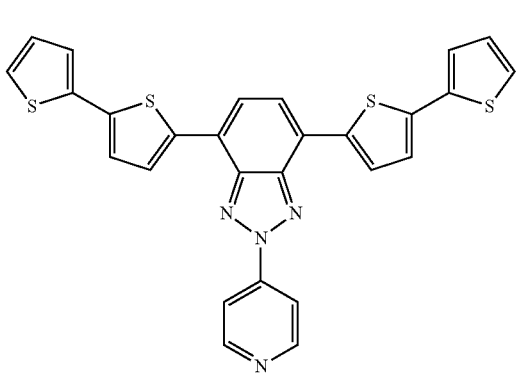

Step 1: Synthesis of [2,2'-Bithiophen]-5-yltributylstannane

Starting from 2,2'-bithiophene and applying a procedure similar to that for chromophore Example 8 (Step 1) led to [2,2'-bithiophen]-5-yltributylstannane of purity 50% that was used in the next step without further purification.

Step 2: Synthesis of Example 9—4,7-Di([2,2'-bithiophen]-5-yl)-2-(pyridin-4-yl)-2H-benzo[d][1,2,3]triazole A mixture of Intermediate A (704 mg, 2.0 mmol), 50% [2,2'-bithiophen]-5-yltributylstannane (2.50 g, 5.5 mmol), bis (triphenylphosphine)palladium(II) dichloride (200 mg, 0.28 mmol), and anhydrous dimethylformamide (20 mL) was stirred under argon and heated at 90° C. for 1 hour. TLC indicated no starting material left. Heating at 90° C. was continued for an additional 2 hours. The volatiles were removed under reduced pressure, and the crude product was purified by column chromatography using silica gel and dichloromethane/ethyl acetate (9:1) as an eluent. The obtained product was washed with ethyl acetate (50 mL) and dried in a vacuum oven to give 4,7-di([2,2'-bithiophen]-5-yl)-2-(pyridin-4-yl)-2H-benzo[d][1,2,3]triazole (Example 9) as red crystals, 150 mg (14%). $^1$H NMR (400 MHz, CDCl$_3$): δ 8.88 (m, 2H, pyridine), 8.40 (m, 2H, pyridine), 8.09 (d, J=4.0 Hz, 2H, thiophene), 7.65 (s, 2H, benzotriazole), 7.31 (dd, J=3.7 and 1.1 Hz, 2H, thiophene), 7.29 (m, 2H, thiophene), 7.27 (m, 2H, thiophene), 7.08 (dd, J=5.2 and 3.7 Hz, 2H, thiophene). UV-vis spectrum (dichloromethane): $\lambda_{max}$=478 nm. Fluorimetry (dichloromethane): $\lambda_{max}$=584 nm.

Example 10

Example 10 is synthesized in a two step process.

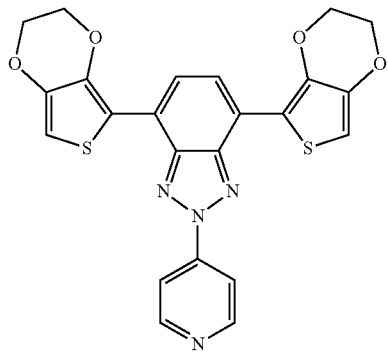

Step 1: Synthesis of tributyl(2,3-dihydrothieno[3,4-b][1,4]dioxin-5-yl)stannane 1.5M n-BuLi in hexane (53 mL, 80 mmol) was added in small portions to a solution of 2,3-dihydrothieno[3,4-b][1,4]dioxine (10.00 g, 80 mmol) and tetramethylethylenediamine (12.0 mL, 80 mmol) in tetrahydrofuran (100 mL) stirred under argon and cooled in a dry ice/acetone bath. The reaction mixture was heated to 35° C., stirred at this temperature for 1 hour, and then cooled in a dry ice/acetone bath. Tributylstannyl chloride (20.3 mL), 75 mmol was then added, the mixture was allowed to warm up, and it was left at room temperature for 16 hours. The volatiles were removed under reduced pressure. The residue was diluted with toluene (100 mL) and chromatographed using a column filled with silica gel (500 mL) washed with 2% triethylamine in hexane (500 mL) to give tributyl(2,3-dihydrothieno[3,4-b][1,4]dioxin-5-yl)stannane (12.17 g, 40%) of high purity. $^1$H NMR (400 MHz, CDCl$_3$): δ 6.57 (s, 1H, thiophene), 4.15 (m, 4H, OCH$_2$CH$_2$O), 1.53 (m, 6H, Bu), 1.32 (quintet, J=7.3 Hz, 6H, Bu), 1.09 (m, 6H, Bu), 0.88 (t, J=7.3 Hz, 9H, Bu).

Step 2: Synthesis of Example 10—4,7-bis(2,3-dihydrothieno[3,4-b][1,4]dioxin-5-yl)-2-(pyridin-4-yl)-2H-benzo[d][1,2,3]triazole A mixture of Intermediate A (0.71 g, 2.0 mmol), tributyl(2,3-dihydrothieno[3,4-b][1,4]dioxin-5-yl)stannane (2.27 g, 5.0 mmol), bis(triphenylphosphine)palladium(II) dichloride (0.20 g, 0.28 mmol), and anhydrous dimethylformamide (20 mL) was stirred under argon and heated at 100° C. for 4 hours. The volatiles were removed under reduced pressure, and the crude product was purified by column chromatography (silica gel, dichloromethane/ethyl acetate 75:25) and washing with ethanol (20 mL) to give 4,7-bis(2,3-dihydrothieno[3,4-b][1,4]dioxin-5-yl)-2-(pyridin-4-yl)-2H-benzo[d][1,2,3]triazole (Example 10) as orange crystals, 0.47 g (49%). $^1$H NMR (400 MHz, CDCl$_3$): δ 8.82 (m, 2H, pyridine), 8.37 (m, 2H, pyridine), 8.20 (s, 2H, benzotriazole), 6.53 (s, 2H, thiophene), 4.39 (s, 4H, OCH$_2$CH$_2$O), 4.30 (s, 4H, OCH$_2$CH$_2$O). UV-vis spectrum (dichloromethane): $\lambda_{max}$=448 nm. Fluorimetry (dichloromethane): $\lambda_{max}$=559 nm.

Example 11

Example 11 was synthesized using two different methods.

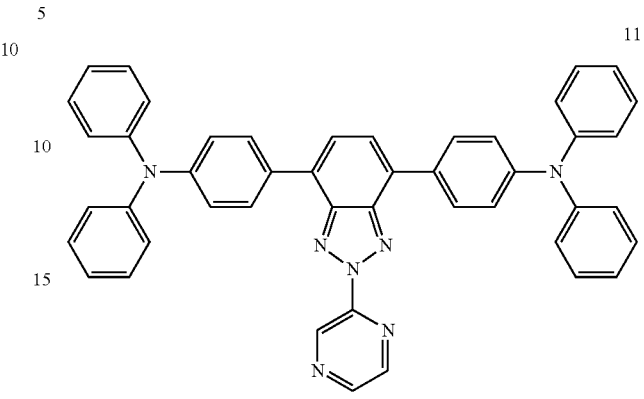

Method 1: A mixture of Intermediate B (purity 80%, 1.00 g, 2.26 mmol), 4-(diphenylamino)phenylboronic acid (1.72 g, 6 mmol), sodium carbonate (2.69 g, 25 mmol) in water (10 mL), tetrakis(triphenylphosphine)palladium (0) (0.58 g, 0.5 mmol), n-butanol (40 mL), and toluene (10 mL) was heated under argon at 120° C. for 48 hours. The reaction mixture is poured into water (200 mL), stirred for 2 hours, and extracted with dichloromethane (2×100 mL). The volatiles were removed under reduced pressure, and the residue was chromatographed (silica gel, toluene). The separated product was recrystallized from ethanol to give 4,7-bis(4-(N,N-diphenylamino)phenyl)-2-(pyrazin-2-yl)-2H-benzo[d][1,2,3]triazole (Example 11) as red crystals, 0.35 g (23%). $^1$H NMR (400 MHz, CDCl$_3$): δ 9.73 (s, 1H, pyrazine), 8.72 (d, J=2.5 Hz, 1H, pyrazine), 8.65 (d, J=2.5 Hz, 1H, pyrazine), 8.03 (d, J=8.8 Hz, 4H, p-phenylene), 7.68 (s, 2H, benzotriazole), 7.31 (m, 8H, Ph), 7.18-7.31 (m, 20H, p-phenylene and Ph), 7.06 (m, 4H, Ph). UV-vis spectrum (dichloromethane): $\lambda_{max}$=455 nm. Fluorimetry (dichloromethane): $\lambda_{max}$=610 nm.

Method 2: A mixture of Intermediate D (724 mg, 1.2 mmol), 2-chloropyrazine (0.27 mL, 3.0 mmol), potassium carbonate (1.33 g, 10 mmol), and dimethylformamide (12 mL) was stirred under argon and heated at 120° C. for 20 hours. The volatiles were removed under reduced pressure, and the residue was chromatographed using silica gel and hexane/dichloromethane/ethyl acetate (50:48:2) as an eluent to give Example 11 (580 mg, 70%).

Example 12

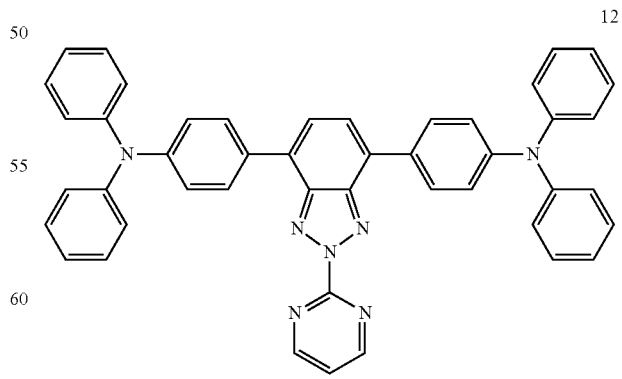

A mixture of Intermediate D (500 mg, 0.82 mmol), 2-chloropyrimidine (343 mg, 3.0 mmol), 60% NaH (60 mg, 1.5 mmol), and dimethylformamide (10 mL) was stirred under argon and heated at 120° C. for 20 hours. The reaction mixture was poured into water (100 mL) and extracted with dichloromethane (4×100 mL). The extract was dried over anhydrous sodium sulfate, the volatiles were removed under reduced pressure, and the residue was chromatographed using silica gel and dichloromethane/ethyl acetate (95:5) as an eluent. The obtained product was recrystallized from ethanol to give 4,7-bis(4-(N,N-diphenylamino)phenyl)-2-(pyrimidin-2-yl)-2H-benzo[d][1,2,3]triazole (Example 12), orange crystals, 340 mg (61%). $^{1}$H NMR (400 MHz, CDCl$_3$): δ 8.99 (d, J=5.1 Hz, 2H, pyrimidine), 8.02 (d, J=8.8 Hz, 4H, p-phenylene), 7.66 (s, 2H, benzotriazole), 7.47 (t, J=4.8 Hz, 1H, pyrimidine), 7.28 (m, 8H, Ph), 7.21 (d, J=8.4 Hz, 4H, p-phenylene), 7.18 (m, 8H, Ph), 7.05 (tt, J=7.3 and 1.1 Hz, 4H, Ph). UV-vis spectrum (dichloromethane): $\lambda_{max}$=451 nm. Fluorimetry (dichloromethane): $\lambda_{max}$=600 nm.

Examples 13 and 14

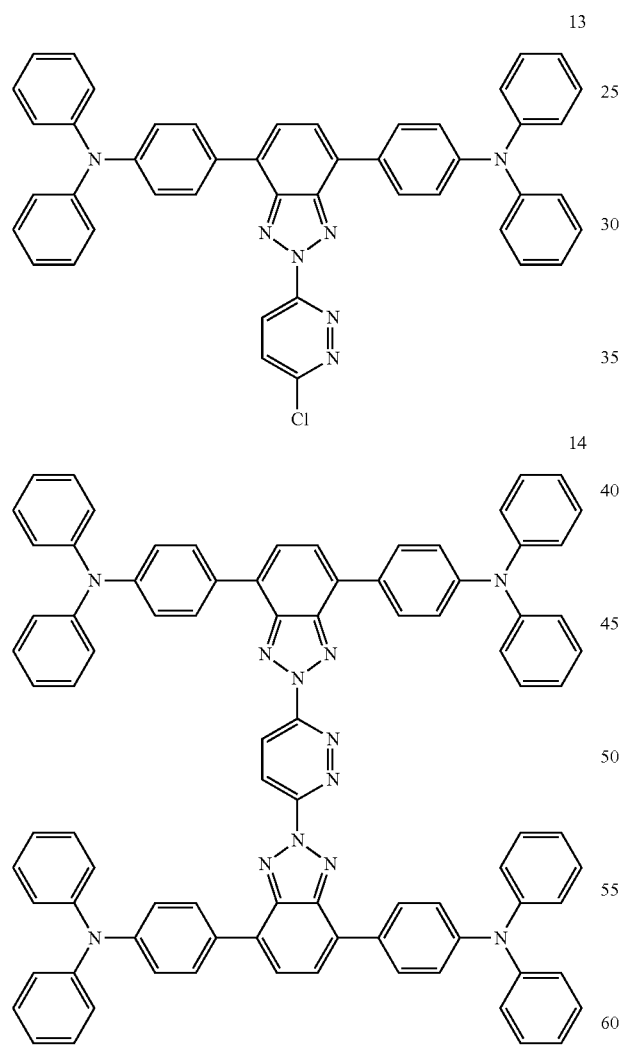

A mixture of Intermediate D (0.90 g, 1.49 mmol), 3,6-dichloropyridazine (1.49 g, 3.0 mmol), potassium carbonate (0.69 g, 5 mmol), and dimethylformamide (12 mL) was stirred under argon and heated at 60° C. for 16 hours. According to TLC, a small amount of the starting material remained. The reaction mixture was poured onto crushed ice (100 g), acidified to pH 5 with acetic acid, and stirred for 1 hour. The precipitate was filtered off, washed with water, and dried in a vacuum oven. The crude product was chromatographed using silica gel and dichloromethane/ethyl acetate (95:5) as an eluent. The first fraction gave Example 14, deep-red crystals, 330 mg (17%). 1H NMR (400 MHz, CDCl$_3$): δ 8.82 (d, s, 2H, pyrazine), 8.08 (d, J=8.8 Hz, 8H, p-phenylene), 7.71 (s, 4H, benzotriazole), 7.31 (m, 16H, Ph), 7.21 (m, 24H, Ph and p-phenylene), 7.08 (t, J=7.3 Hz, Ph). UV-vis spectrum (dichloromethane): $\lambda_{max}$=475 nm. Fluorimetry (dichloromethane): $\lambda_{max}$=641 nm.

The second fraction gave 4,7-bis(4-(N,N-diphenylamino)phenyl)-2-(6-chloropyridazin-3-yl)-2H-benzo[d][1,2,3]triazole (Example 13), bright-red crystals, 490 mg (46%). $^1$H NMR (400 MHz, CDCl$_3$): δ 8.57 (d, J=9.1 Hz, 1H, pyrazine), 8.02 (d, J=8.8 Hz, 4H, p-phenylene), 7.75 (d, J=9.1 Hz, 1H, pyrazine), 7.69 (s, 2H, benzotriazole), 7.30 (m, 8H, Ph), 7.20 (m, 12H, Ph and p-phenylene), 7.18 (m, 8H, Ph), 7.07 (tt, J=7.3 and 1.1 Hz, 4H, Ph). UV-vis spectrum (dichloromethane): $\lambda_{max}$=469 nm. Fluorimetry (dichloromethane): $\lambda_{max}$=618 nm.

Example 15

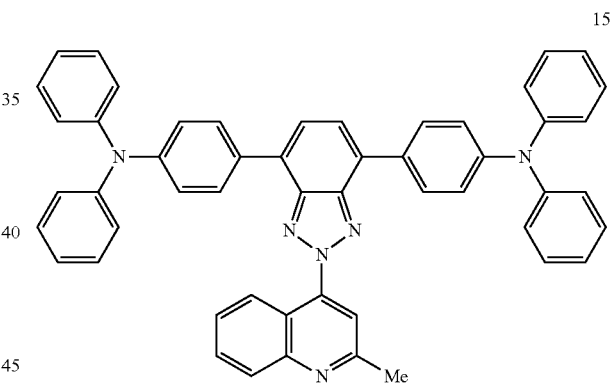

A mixture of Intermediate D (605 mg, 1.0 mmol), 4-chloroquinaldine (266 mg, 1.5 mmol), 60% NaH (60 mg, 1.5 mmol), and dimethylformamide (15 mL) was stirred under argon and heated at 160° C. for 4 days. The volatiles were removed under reduced pressure, and the residue was chromatographed using silica gel and hexane/ethyl acetate (2:1) as an eluent. The obtained product was recrystallized from ethanol to give 4,7-bis(4-(N,N-diphenylamino)phenyl)-2-(2-methylquinolin-4-yl)-2H-benzo[d][1,2,3]triazole (Example 15) as orange crystals, 520 mg (70%). 1H NMR (400 MHz, CDCl$_3$): δ 8.73 (d, J=8.4 Hz, 1H, quinaldine), 8.13 (d, J=8.4 Hz, 1H, quinaldine), 8.07 (d, J=8.8 Hz, 4H, p-phenylene), 7.98 (s, 1H, quinaldine), 7.77 (ddd, J=8.4, 7.0 and 1.1 Hz, 1H, quinaldine), 7.73 (s, 2H, benzotriazole), 7.60 (ddd, J=8.4, 7.3 and 1.1 Hz, 1H, quinaldine), 7.25-7.30 (m, 8H, Ph), 7.21 (d, J=8.4 Hz, 4H, p-phenylene), 7.16-7.19 (m, 8H, Ph), 7.05 (tt, J=7.3 and 1.1 Hz, 4H, Ph), 2.86 (s, 3H, quinaldine). UV-vis spectrum (dichloromethane): $\lambda_{max}$=438 nm. Fluorimetry (dichloromethane): $\lambda_{max}$=617 nm.

Example 16

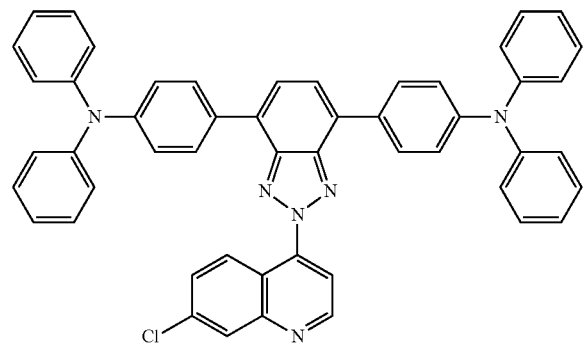

16

Starting from Intermediate D (605 mg, 1.0 mmol), 4,7-dichloroquinoline (297 mg, 1.5 mmol), 60% NaH (60 mg, 1.5 mmol), and applying a procedure similar to that for chromophore Example 15, 4,7-bis(4-(N,N-diphenylamino)phenyl)-2-(7-chloroquinolin-4-yl)-2H-benzo[d][1,2,3]triazole (Example 16), 180 mg (23%) was obtained as orange crystals. $^1$H NMR (400 MHz, CDCl$_3$): δ 9.09 (d, J=4.7 Hz, 1H, quinoline), 8.93 (d, J=9.2 Hz, 1H, quinoline), 8.23 (d, J=2.2 Hz, 1H, quinoline), 8.16 (d, J=4.7 Hz, 1H, quinoline) 8.06 (d, J=8.8 Hz, 4H, p-phenylene), 7.73 (s, 2H, benzotriazole), 7.63 (dd, J=9.1 and 2.2 Hz, 1H, quinoline), 7.25-7.30 (m, 8H, Ph), 7.21 (d, J=8.4 Hz, 4H, p-phenylene), 7.16-7.19 (m, 8H, Ph), 7.06 (tt, J=7.3 and 1.1 Hz, 4H, Ph). UV-vis spectrum (dichloromethane): $\lambda_{max}$=448 nm. Fluorimetry (dichloromethane): $\lambda_{max}$=631 nm.

Example 17

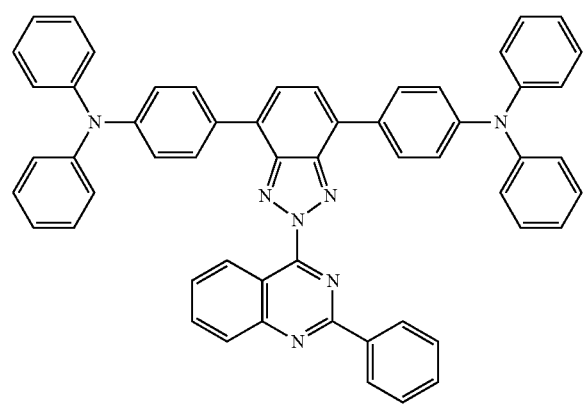

17

A mixture of Intermediate D (605 mg, 1.0 mmol), 4-chloro-2-phenylquinoline (481 mg, 2.0 mmol), 60% NaH (80 mg, 2.0 mmol), and dimethylformamide (15 mL) was stirred under argon and heated at 50° C. for 3 hours. After cooling, the mixture was diluted with chlorobenzene (50 mL) and treated with a piece of dry ice to reduce the pH. The volatiles were removed under reduced pressure, and the residue was chromatographed using silica gel and hexane/dichloromethane (2:1) as an eluent to give 4,7-bis(4-(N,N-diphenylamino)phenyl)-2-(2-phenylquinolin-4-yl)-2H-benzo[d][1,2,3]triazole (Example 17) as orange-pink crystals, 640 mg (79%). $^1$H NMR (400 MHz, CDCl$_3$): δ 8.70 (m, 3H, 2-phenylquinazolin-4-yl), 8.22 (d, J=8.4 Hz, 1H, 2-phenylquinazolin-4-yl), 8.12 (d, J=8.8 Hz, 4H, p-phenylene), 7.97 (ddd, J=8.4, 6.9 and 1.4 Hz, 1H, 2-phenylquinazolin-4-yl), 7.76 (s, 2H, benzotriazole), 7.68 (ddd, J=8.5, 7.0 and 1.1 Hz, 1H, 2-phenylquinazolin-4-yl), 7.53 (m, 3H, 2-phenylquinazolin-4-yl), 7.25-7.30 (m, 8H, Ph), 7.21 (d, J=8.4 Hz, 4H, p-phenylene), 7.16-7.19 (m, 8H, Ph), 7.05 (tt, J=7.3 and 1.1 Hz, 4H, Ph), 2.86 (s, 3H, quinaldine). UV-vis spectrum (dichloromethane): $\lambda_{max}$=452 nm. Fluorimetry (dichloromethane): $\lambda_{max}$=654 nm.

Example 18

Example 18 is synthesized in a two step process.

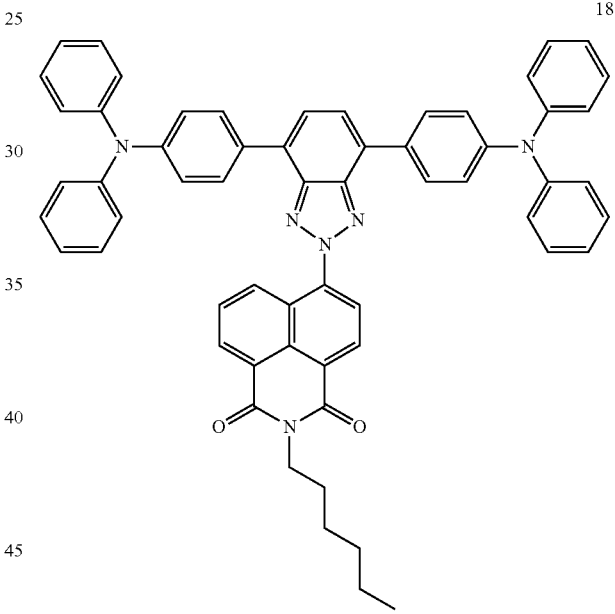

18

Step 1: Synthesis of 6-Bromo-2-hexyl-1H-benzo[de]isoquinoline-1,3(2H)-dione

A mixture of 4-bromo-1,8-naphthalic anhydride (21.40 g, 77.2 mmol), n-hexylamine (13.1 mL, 100 mmol), toluene (200 mL), and chloroform (200 mL) was heated to boil for 1 hour. Precipitate formed making stirring difficult. The mixture was acidified with acetic acid, and heating was continued at 90° C. with distillation of chloroform. After all precipitate dissolved, the reaction mixture was poured onto crushed ice (300 g) and acidified with concentrated HCl to pH 1. After the ice melted, the solid was filtered off and dried. The crude product was purified by column chromatography (silica gel, hexane/ethyl acetate 2:1) to give 6-bromo-2-hexyl-1H-benzo[de]isoquinoline-1,3(2H)-dione (20.66 g, 74%).

Step 2: Synthesis of Example 18—6-(4,7-bis(4-(N,N-diphenylamino)phenyl)-2H-benzo[d][1,2,3]triazol-2-yl)-2-hexyl-1H-benzo[de]isoquinoline-1,3(2H)-dione A mixture of Intermediate D (1.00 g, 1.65 mmol), 6-bromo-2-hexyl-1H-benzo[de]isoquinoline-1,3(2H)-dione (720 mg, 2.0 mmol), potassium carbonate (276 mg, 2.0 mmol), CuI (382 mg, 2.0 mmol), and dimethylformamide (12 mL) was stirred under argon and heated at 160° C. for 3 days. After cooling, the reaction mixture was diluted with ethyl acetate (100 mL), washed with water (3×50 mL), dried over magnesium sulfate, and the solvent was removed under reduced pressure. The crude product was purified by column chromatography (silica gel, hexane/dichloromethane 1:1) and washing with ethanol to give 6-(4,7-bis(4-(N,N-diphenylamino)phenyl)-2H-benzo[d][1,2,3]triazol-2-yl)-2-hexyl-1H-benzo[de]isoquinoline-1,3(2H)-dione (Example 18), brown-violet crystals, 445 mg (30%). $^1$H NMR (400 MHz, CDCl$_3$): δ 9.08 (dd, J=8.4 and 1.1 Hz, 1H, naphthalene), 8.74 (d, J=7.6 Hz, 1H, naphthalene), 7.69 (dd, J=7.3 and 1.1 Hz, 1H, naphthalene), 8.43 (d, J=8.1 Hz, 1H, naphthalene), 8.07 (d, J=8.8 Hz, 4H, p-phenylene), 7.85 (dd, J=8.4 and 7.3 Hz, 1H, naphthalene), 7.74 (s, 2H, benzotriazole), 7.28 (m, 8H, Ph), 7.21 (d, J=8.4 Hz, 4H, p-phenylene), 7.18 (m, 8H, Ph), 7.05 (tt, J=7.3 and 1.1 Hz, 4H, Ph). UV-vis spectrum (dichloromethane): $\lambda_{max}$=381 nm. Fluorimetry (dichloromethane): $\lambda_{max}$=481 nm.

Example 19

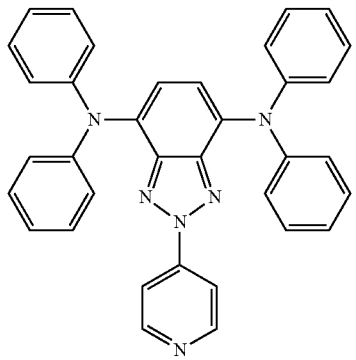

A mixture of Intermediate A (1.05 g, 3.0 mmol), diphenylamine (2.03 g, 12.0 mmol), potassium carbonate (1.66 g, 12.0 mmol), CuI (1.14 g, 6.0 mmol), and dimethylformamide (20 mL) was stirred under argon and heated at 160° C. for 3 days. After cooling, the reaction mixture was poured into water (100 mL) and stirred for 15 minutes. The precipitate was filtered off and washed with water (50 mL). A suspension of this solid in dichloromethane (100 mL) was treated with concentrated ammonium hydroxide (20 mL) and stirred for 1 hour. The dichloromethane layer was separated, dried over sodium sulfate and chromatographed (silica gel, dichloromethane/ethyl acetate 9:1). The obtained product was recrystallized from ethanol to give 4,7-bis(N,N-diphenylamino)-2-(pyridin-4-yl)-2H-benzo[d][1,2,3]triazole (Example 19), orange crystals, 55 mg (3%). $^1$H NMR (400 MHz, CDCl$_3$): δ 8.57 (m, 2H, pyridine), 7.64 (m, 2H, pyridine), 7.28 (m, 8H, Ph), 7.15 (m, 8H, Ph), 7.06 (t, J=7.3 Hz, 4H, Ph), 6.96 (s, 2H, benzotriazole. UV-vis spectrum (dichloromethane): $\lambda_{max}$=471 nm. Fluorimetry (dichloromethane): $\lambda_{max}$=640 nm.

Example 20

Example 20 is synthesized in a two step process.

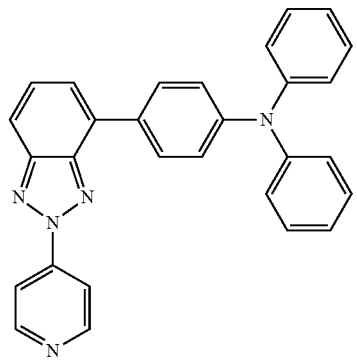

Step 1: Synthesis of 4-bromo-7-(N,N-diphenylamino)phenyl-2-(pyridin-4-yl)-2H-benzo[d][1,2,3]triazole A mixture of Intermediate A (purity 80%, 1.38 g, 3.1 mmol), sodium carbonate (0.80 g, 7.5 mmol) in water (4 mL), 4-(diphenylamino)phenylboronic acid (0.58 g, 2.0 mmol), tetrakis(triphenylphosphine)palladium (0) (0.58 g, 0.5 mmol), n-butanol (30 mL), and toluene (20 mL) was heated under argon at 110° C. for 3 hours. After cooling, the reaction mixture was poured into water (200 mL), stirred for 1 hour and extracted with dichloromethane (2×200 mL). The extract was concentrated under reduced pressure and chromatographed using a column packed with silica gel and dichloromethane/ethyl acetate (9:1) as an eluent. The first fraction gave dye Example 1 (0.12 g, 11%). The second fraction gave 4-bromo-7-(N,N-diphenylamino)phenyl-2-(pyridin-4-yl)-2H-benzo[d][1,2,3]triazole (0.79 g, 76%). $^1$H NMR (400 MHz, CDCl$_3$): δ 8.82 (m, 2H, pyridine), 8.33 (m, 2H, pyridine), 7.96 (d, J=8.4 Hz, 2H, p-phenylene), 7.69 (d, J=7.7 Hz, 1H, benzotriazole), 7.46 (d, J=7.7 Hz, 1H, benzotriazole), 7.30 (m, 4H, Ph), 7.19 (m, 6H, p-phenylene and Ph), 7.08 (t, J=7.3 Hz, 2H, Ph).

Step 2: Synthesis of Example 20—4-(N,N-diphenylamino)phenyl-2-(pyridin-4-yl)-2H-benzo[d][1,2,3]triazole Sodium borohydride (256 mg, 8.0 mmol) was added in small portions within 2 hours to a stirred solution of 4-bromo-7-(N,N-diphenylamino)phenyl-2-(pyridin-4-yl)-2H-benzo[d][1,2,3]triazole (200 mg, 0.38 mmol) and cuprous chloride (99 mg, 1.0 mmol) in dichloromethane/methanol (1:1, 20 mL). After stirring for another 2 hours, the mixture was acidified with 5N HCl and stirred for 30 minutes. The reaction mixture was poured into water (100 mL), neutralized with 5N NaOH and extracted with dichloromethane (2×100 mL). The extract was dried over anhydrous sodium carbonate, the solvent was evaporated, and the residue was chromatographed (silica gel, dichloromethane/ethyl acetate 9:1) to give yellow crystals of 4-(N,N-diphenylamino)phenyl-2-(pyridin-4-yl)-2H-benzo[d][1,2,3]triazole (Example 20, 100 mg, 60%). 1H NMR (400 MHz, CDCl$_3$): δ 8.80 (m, 2H, pyridine), 8.30 (m, 2H, pyridine), 8.05 (d, J=8.4 Hz, 2H, p-phenylene), 7.83 (dd, J=8.4 and 1.1 Hz, 1H, benzotriazole), 7.59 (dd, J=7.3 and 1.1 Hz, 1H, benzotriazole), 7.51 (dd, J=8.4 and 7.0 Hz, 1H, benzotriazole), 7.30 (m, 4H, Ph), 7.20 (m, 6H, p-phenylene and Ph), 7.08 (t, J=7.3 Hz, 2H, Ph). UV-vis spectrum (dichloromethane): $\lambda_{max}$=400 nm. Fluorimetry (dichloromethane): $\lambda_{max}$=577 nm.

Example 21

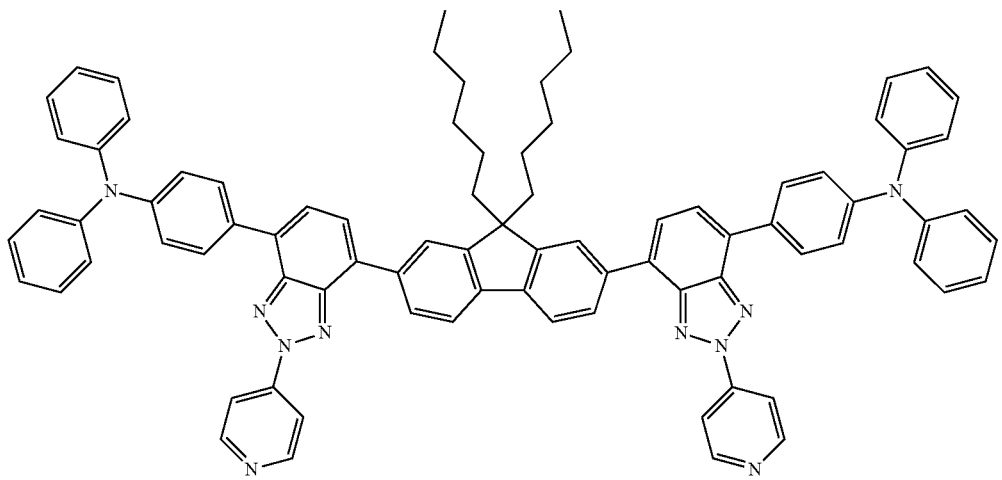

A mixture of Intermediate E (90%, 400 mg, 0.41 mmol), sodium carbonate (1.06 g, 10 mmol) in water (5 mL), 4-(diphenylamino)phenylboronic acid (1.00 g, 2.26 mmol), tetrakis(triphenylphosphine)palladium (0) (0.50 g, 0.43 mmol), n-butanol (20 mL), and toluene (10 mL) was heated under argon at 100° C. for 4 hours. The reaction mixture was poured into water (200 mL), diluted with dichloromethane (100 mL), stirred for 1 hour, and the dichloromethane layer was separated. The aqueous phase was washed with dichloromethane (100 mL). Both dichloromethane solutions were combined, dried over anhydrous sodium sulfate, and the solvent was removed under reduced pressure. The crude product was purified by column chromatography (silica gel, dichloromethane/ethyl acetate 1:1) and recrystallization from ethanol to give 2,7-bis(7-(4-(diphenylamino)phenyl)-2-(pyridin-4-yl)-2H-benzo[d][1,2,3]triazol-4-yl)-9,9-dihexyl-9H-fluorene (Example 21), orange crystals, 350 mg (71%). $^1$H NMR (400 MHz, CDCl$_3$): δ 8.82 (m, 4H, pyridine), 8.37 (m, 4H, pyridine), 8.21 (d, J=1.1 Hz, 2H, fluorene), 8.14 (dd, J=8.1 and 1.5 Hz, 2H, fluorene), 8.09 (d, J=8.8 Hz, 4H, p-phenylene), 7.94 (d, J=8.0 Hz, 2H, fluorene), 7.81 (d, J=7.3 Hz, 2H, benzotriazole), 7.74 (d, J=7.3 Hz, 2H, benzotriazole), 7.30-7.34 (m, 8H, Ph), 7.25 (d, J=8.8 Hz, 4H, p-phenylene), 7.21 (m, 8H, Ph), 7.09 (tt, J=7.3 and 1.1 Hz, 4H, Ph), 2.19 (m, 4H, hexyl), 1.12 (m, 12H, hexyl), 0.95 (m, 4H, hexyl), 0.73 (t, J=6.6 Hz, 6H, hexyl). UV-vis spectrum (dichloromethane): λ$_{max}$=449 nm. Fluorimetry (dichloromethane): λ$_{max}$=585 nm.

Example 22

Example 22 is synthesized in a two step process.

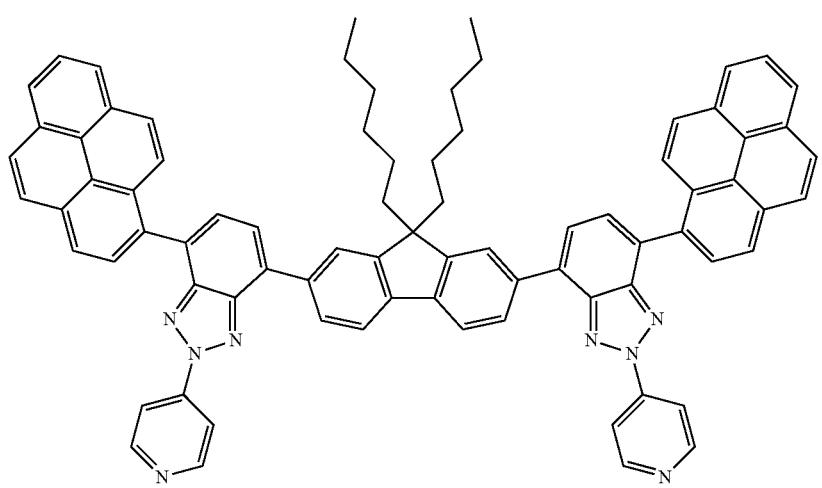

Step 1: Synthesis of 4-Bromo-7-(4-(pyren-1-yl)-2-(pyridin-4-yl)-2H-benzo[d][1,2,3]triazole A mixture of Intermediate A (1.41 g, 4 mmol), pyrene-1-boronic acid (0.49 g, 2.0 mmol), tetrakis(triphenylphosphine)palladium (0) (0.50 g, 0.43 mmol), sodium carbonate (2.12 g, 20 mmol) in water (10 mL), n-butanol (30 mL), and toluene (30 mL) was heated under argon at 110° C. for 5 hours. The reaction mixture was poured into water (200 mL), treated with 5 N NaOH (20 mL), stirred for 1 hour, and extracted with dichloromethane (2×200 mL). The extract was dried over anhydrous sodium carbonate, and the volatiles were removed under reduced pressure. The residue was chromatographed (silica gel, dichloromethane/tetrahydrofuran 9:10) to give 4-bromo-7-(4-(pyren-1-yl)phenyl)-2-(pyridin-4-yl)-2H-benzo[d][1,2,3]triazole (purity 90%, 650 mg, 53% yield) as yellow crystals. $^1$H NMR (400 MHz, CDCl$_3$): δ 8.72 (m, 2H, pyridine), 8.31 (d, J=7.7 Hz, 1H, pyrene), 8.24 (dd, J=7.7 and 1.1 Hz, 1H, pyrene), 8.16-8.20 (m, 6H, pyrene and pyridine), 8.04 (t, J=7.7 Hz, 1H, pyrene), 8.00 (m, 2H, pyrene), 7.86 (d, J=7.7 Hz, 1H, benzotriazole), 7.86 (d, J=7.3 Hz, 1H, benzotriazole).

Step 2: Synthesis of Example 22—2,7-bis(7-(pyren-1-yl)-2-(pyridin-4-yl)-2H-benzo[d][1,2,3]triazol-4-yl)-9,9-dihexyl-9H-fluorene A mixture of 4-bromo-7-(4-(pyren-1-yl)phenyl)-2-(pyridin-4-yl)-2H-benzo[d][1,2,3]triazole (90%, 460 mg, 0.87 mmol), 9,9-dihexylfluorene-2,7-diboronic acid (169 mg, 0.40 mmol), sodium carbonate (530 mg, 5 mmol) in water (3 mL), tetrakis(triphenylphosphine)palladium (0) (250 mg, 0.21 mmol), n-butanol (20 mL), and toluene (20 mL) was heated under argon at 110° C. for 20 hours. The reaction mixture was poured into water (200 mL), diluted with dichloromethane (100 mL), stirred for 1 hour, and the dichloromethane layer was separated. The aqueous phase was washed with dichloromethane (100 mL). Both dichloromethane solutions were combined, and the solvent was removed under reduced pressure. The crude product was purified by column chromatography (silica gel, dichloromethane/ethyl acetate 75:25) and recrystallization from toluene to give 2,7-bis(7-(pyren-1-yl)-2-(pyridin-4-yl)-2H-benzo[d][1,2,3]triazol-4-yl)-9,9-dihexyl-9H-fluorene (Example 22), yellow crystals, 232 mg (52%). $^1$H NMR (400 MHz, CDCl$_3$): δ 8.73 (m, 4H, pyridine), 8.36 (d, J=7.7 Hz, 2H), 8.33 (d, J=1.1 Hz, 2H), 8.30 (d, J=7.7 Hz, 2H), 8.23-8.28 (m, 8H), 8.16-8.22 (m, 8H), 8.02-8.07 (m, 6H), 7.98 (d, J=6.9 Hz, 2H), 7.82 (d, J=7.3 Hz, 2H), 2.26 (m, 4H), 1.25 (m, 4H), 1.18 (m, 8H), 1.02 (m, 4H), 0.77 (t, J=6.7 Hz, 6H). UV-vis spectrum (dichloromethane): $\lambda_{max}$=419 nm. Fluorimetry (dichloromethane): $\lambda_{max}$=525 nm.

Example 23

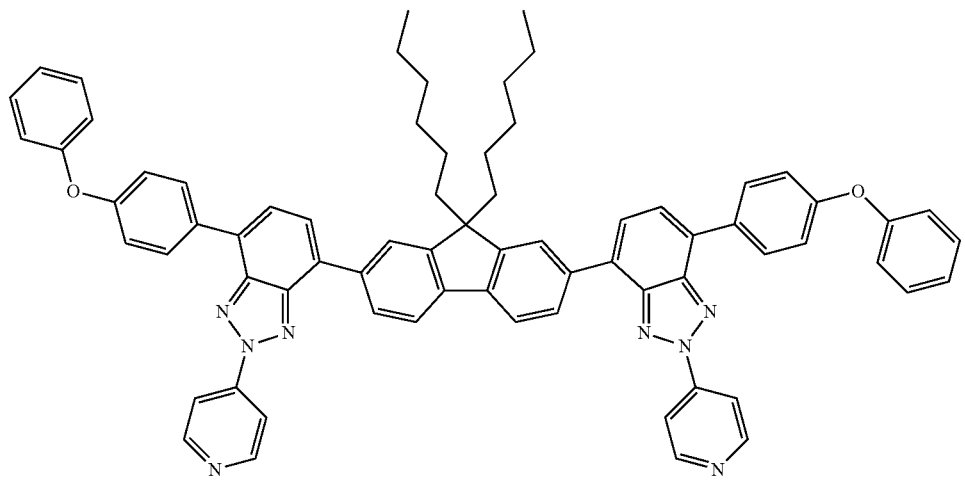

A mixture of Intermediate E (70%, 370 mg, 0.29 mmol), sodium carbonate (1.06 g, 10 mmol) in water (5 mL), 4-phenoxyphenylboronic acid (428 mg, 2.00 mmol), tetrakis(triphenylphosphine)palladium (0) (0.50 g, 0.43 mmol), n-butanol (20 mL), and toluene (20 mL) was heated under argon at 100° C. for 16 hours. The reaction mixture was poured into water (200 mL), stirred for 1 hour, and extracted with (100 mL). The volatiles were removed under reduced pressure, and the residue was chromatographed (silica gel, dichloromethane/ethyl acetate 75:25). The obtained product was recrystallized from dichloromethane/ethanol to give 2,7-bis(7-(4-phenoxyphenyl)-2-(pyridin-4-yl)-2H-benzo[d][1,2,3]triazol-4-yl)-9,9-dihexyl-9H-fluorene (Example 23), yellow crystals, 182 mg (59%). $^1$H NMR (400 MHz, CDCl$_3$): δ 8.83 (m, 4H, pyridine), 8.37 (m, 4H, pyridine), 8.21 (s, 2H, fluorene), 8.14 (m, 6H, fluorene and p-phenylene), 7.95 (d, J=8.0 Hz, 2H, fluorene), 7.82 (d, J=7.3 Hz, 2H, benzotriazole), 7.74 (d, J=7.3 Hz, 2H, benzotriazole), 7.41 (m, 4H, Ph), 7.12-7.23 (m, 10H, Ph and p-phenylene), 2.20 (m, 4H, hexyl), 1.18 (m, 4H, hexyl), 1.13 (m, 8H, hexyl), 0.95 (m, 4H, hexyl), 0.73 (t, J=6.8 Hz, 6H, hexyl). UV-vis spectrum (dichloromethane): $\lambda_{max}$=417 nm. Fluorimetry (dichloromethane): $\lambda_{max}$=508 nm.

Example 24

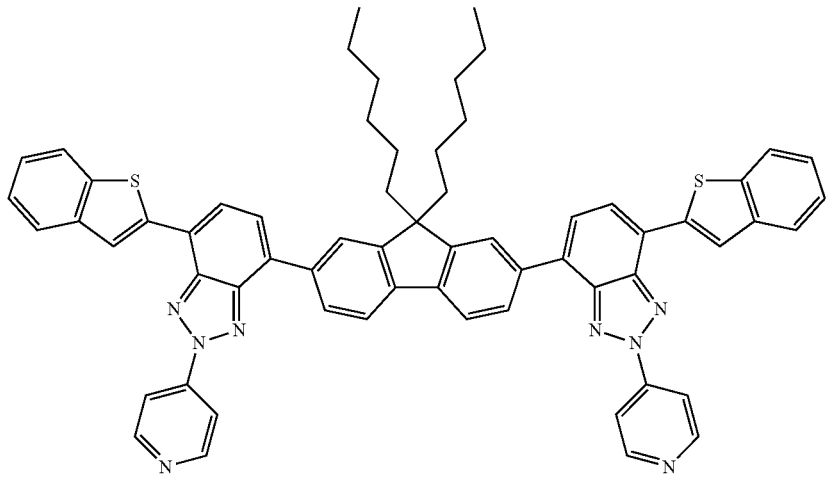

A mixture of Intermediate E (90%, 488 mg, 0.50 mmol),), benzo[b]thiophen-2-ylboronic acid (356 mg, 2.00 mmol), sodium carbonate (530 mg, 5 mmol) in water (4 mL), tetrakis (triphenylphosphine)palladium (0) (240 mg, 0.20 mmol), n-butanol (15 mL), and toluene (15 mL) was heated under argon at 110° C. for 24 hours. The reaction mixture was poured into water (200 mL), treated with 5N NaOH (25 mL), stirred for 1 hour, and extracted with dichloromethane (3×200 mL). The volatiles were removed under reduced pressure, and the residue was chromatographed (silica gel, dichloromethane/tetrahydrofuran 9:1). The obtained product was washed with ethyl acetate and dried in a vacuum oven to give 2,7-bis(7-(benzo[b]thiophen-2-yl)-2-(pyridin-4-yl)-2H-benzo[d][1,2,3]triazol-4-yl)-9,9-dihexyl-9H-fluorene (Example 24), orange crystals, 430 mg (87%). 1H NMR (400 MHz, CDCl$_3$): δ 8.89 (m, 4H, pyridine), 8.56 (s, 2H, benzothiophene), 8.44 (m, 4H, pyridine), 8.21 (s, 2H, fluorene), 8.14 (d, 2H, J=8.8 Hz, fluorene), 7.88-7.98 (m, 8H, benzothiophene, fluorene and benzotriazole), 7.79 (d, J=7.3 Hz, 2H, benzotriazole), 7.41 (m, 4H, benzothiophene), 2.20 (m, 4H, hexyl), 1.20 (m, 4H, hexyl), 1.14 (m, 8H, hexyl), 0.95 (m, 4H, hexyl), 0.74 (t, J=6.5 Hz, 6H, hexyl). UV-vis spectrum (dichloromethane): $\lambda_{max}$=440 nm. Fluorimetry (dichloromethane): $\lambda_{max}$=515 nm.

Example 25

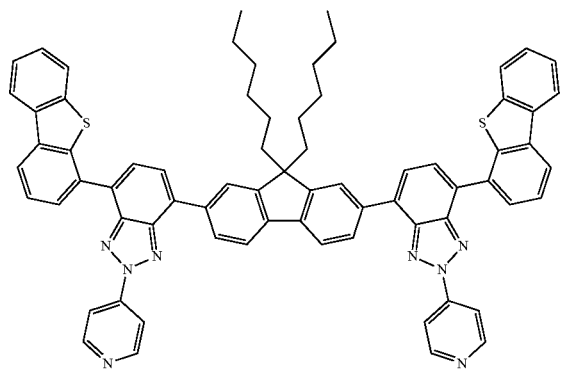

A mixture of Intermediate E (90%, 488 mg, 0.50 mmol), dibenzo[b,d]thiophen-4-ylboronic acid (456 mg, 2.00 mmol), sodium carbonate (530 mg, 5 mmol) in water (4 mL), tetrakis(triphenylphosphine)palladium (0) (240 mg, 0.20 mmol), n-butanol (20 mL), and toluene (20 mL) was stirred and heated under argon at 110° C. for 48 hours. The reaction mixture was poured into water (200 mL), treated with 5N NaOH (25 mL), stirred for 1 hour, and extracted with dichloromethane (3×200 mL). The volatiles were removed under reduced pressure, and the residue was chromatographed (silica gel, dichloromethane/tetrahydrofuran 9:1). The obtained product was recrystallized from acetone to give 2,7-bis(7-(dibenzo[b,d]thiophen-1-yl)-2-(pyridin-4-yl)-2H-benzo[d][1,2,3]triazol-4-yl)-9,9-dihexyl-9H-fluorene (Example 25), yellow-green crystals, 465 mg (85%). 1H NMR (400 MHz, CDCl$_3$): δ 8.80 (m, 4H, pyridine), 8.33 (m, 4H, pyridine), 8.30 (dd, J=7.7 Hz, 2H, dibenzothiophene), 8.27 (s, 2H, fluorene), 8.25 (m, 2H, dibenzothiophene), 8.22 (dd, J=8.1 and 2.4 Hz, 2H, fluorene), 8.10 (d, J=7.7 Hz, 2H, benzotriazole), 8.04 (dd, J=7.3 and 0.7 Hz, 2H, dibenzothiophene), 8.01 (d, J=8.1 Hz, 2H, fluorene) 7.92 (d, J=7.4 Hz, 2H, benzotriazole), 7.86 (m, 2H, dibenzothiophene), 7.51 (m, 4H, dibenzothiophene), 2.23 (m, 4H, hexyl), 1.21 (m, 4H, hexyl), 1.15 (m, 8H, hexyl), 0.97 (m, 4H, hexyl), 0.75 (t, J=7.0 Hz, 6H, hexyl). UV-vis spectrum (dichloromethane): $\lambda_{max}$=411 nm. Fluorimetry (dichloromethane): $\lambda_{max}$=496 nm.

Examples 26, 27, and 28

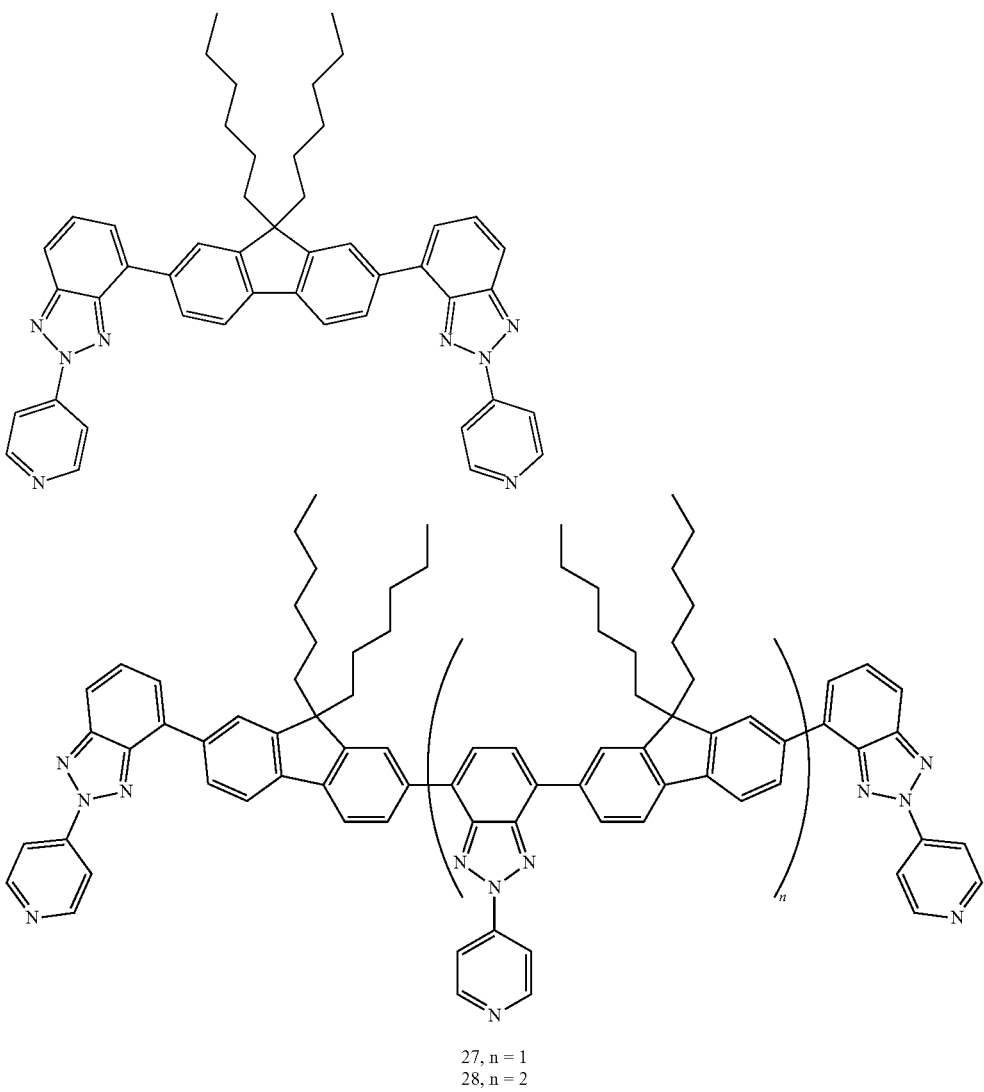

27, n = 1
28, n = 2

A mixture of Intermediate A (3.52 g, 10 mmol), 9,9-dihexylfluorene-2,7-diboronic acid (1.90 g, 4.5 mmol), sodium carbonate (2.12 g, 20 mmol) in water (10 mL), tetrakis(triphenylphosphine)palladium (0) (1.00 g, 0.86 mmol), n-butanol (80 mL), and toluene (20 mL) was stirred and heated under argon at 110° C. After 48 hours, 1-bromo-4-butylbenzene (3.0 mL, 17 mmol) was added followed by sodium carbonate (2.12 g, 20 mmol) in water (10 mL) and tetrakis(triphenylphosphine)palladium (0) (1.00 g, 0.86 mmol), and heating was continued for an additional 20 hours. The reaction mixture was poured into water (200 mL and extracted with ethyl acetate). The extract was dried over anhydrous sodium sulfate, the volatiles were removed under reduced pressure, and the residue was chromatographed (silica gel, dichloromethane/ethyl acetate 3:1). The first fraction gave Intermediate E (414 mg, 10%).

The material from the second fraction was recrystallized from ethanol to give 2,7-bis(2-(pyridin-4-yl)-2H-benzo[d][1,2,3]triazol-4-yl)-9,9-dihexylfluorene (Example 26) as yellow-green crystals (335 mg, 10%). $^1$H NMR (400 MHz, CDCl$_3$): δ 8.82 (m, 4H, pyridine), 8.33 (m, 4H, pyridine), 8.16 (d, J=1.1 Hz, 2H, fluorene), 8.09 (dd, J=8.0 and 1.4 Hz, 2H, fluorene), 7.93 (m, 4H, benzotriazole and fluorene), 7.73 (dd, J=8.0 and 0.8 Hz, 2H, benzotriazole), 7.59 (dd, J=8.4 and 8.0 Hz, 2H, benzotriazole), 2.16 (m, 4H, hexyl), 1.11-1.14 (m, 12H, hexyl), 0.89 (m, 4H, hexyl), 0.73 (t, J=6.8 Hz, 6H, hexyl). UV-vis spectrum (dichloromethane): $\lambda_{max}$=385 nm. Fluorimetry (dichloromethane): $\lambda_{max}$=480 nm.

The third fraction gave dye Example 27 as yellow crystals (480 mg, 12%). $^1$H NMR (400 MHz, CDCl$_3$): δ 8.84 (m, 6H, pyridine), 8.39 (m, 2H, pyridine), 8.34 (m, 4H, pyridine), 8.23 (s, 2H, fluorene), 8.15-8.18 (m, 4H), 8.11 (dd, J=7.7 and 1.5 Hz, 2H), 7.91-7.98 (m, 8H), 7.88 (s, 2H, benzotriazole), 7.75 (d, J=7.0 Hz, 2H, benzotriazole), 7.60 (dd, J=8.4 and 7.0 Hz, 2H, benzotriazole), 2.20 (m, 8H, hexyl), 1.13-1.24 (m, 24H, hexyl), 0.95 (m, 8H, hexyl), 0.74 (t, J=6.6 Hz, 12H, hexyl). UV-vis spectrum (dichloromethane): $\lambda_{max}$=421 nm. Fluorimetry (dichloromethane): $\lambda_{max}$=512 nm.

The forth fraction gave dye Example 28, yellow crystals (75 mg, 2%). $^1$H NMR (400 MHz, CDCl$_3$): δ 8.85 (m, 8H, pyridine), 8.41 (m, 4H, pyridine), 8.34 (m, 4H, pyridine), 8.24

(m, 4H), 8.15-8.19 (m, 6H), 8.11 (dd, J=7.6 and 1.5 Hz, 2H), 7.91-8.00 (m, 8H), 7.89 (s, 4H, benzotriazole), 7.75 (d, J=7.0 Hz, 2H, benzotriazole), 7.60 (dd, J=8.4 and 7.0 Hz, 2H, benzotriazole), 2.20 (m, 12H, hexyl), 1.14-1.21 (m, 36H, hexyl), 0.98 (m, 12H, hexyl), 0.74 (t, J=6.6 Hz, 18H, hexyl). UV-vis spectrum (dichloromethane): $\lambda_{max}$=430 nm. Fluorimetry (dichloromethane): $\lambda_{max}$=513 nm.

Example 29

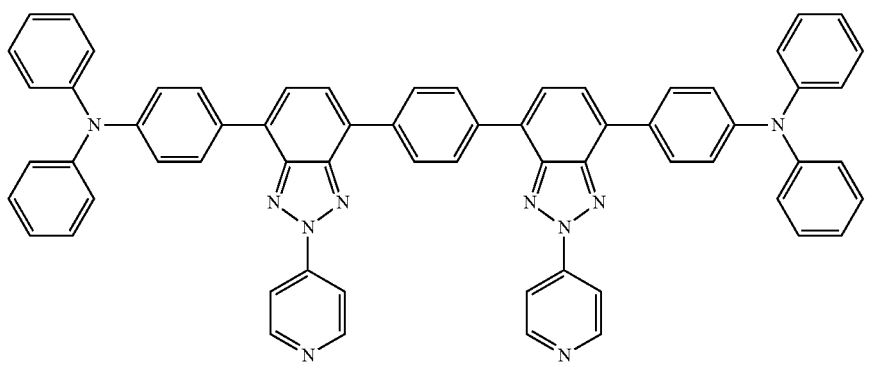

A mixture of Intermediate F (80%, 300 mg, 0.38 mmol), sodium carbonate (1.06 g, 10 mmol) in water (5 mL), 4-(diphenylamino)phenylboronic acid (1.00 g, 2.26 mmol), tetrakis(triphenylphosphine)palladium (0) (0.50 g, 0.43 mmol), n-butanol (20 mL), and toluene (20 mL) was heated under argon at 110° C. for 20 hours. The reaction mixture was poured into water (200 mL), treated with 5N NaOH (20 mL), stirred for 1 hour, and extracted with dichloromethane (5×300 mL). The volatiles were removed under reduced pressure, and the residue was chromatographed (silica gel, dichloromethane/tetrahydrofuran 4:1). The obtained product was triturated with hot ethanol (30 mL), cooled, and filtered off to give 1,4-bis(7-(4-N,N-diphenylaminophenyl)-2-(pyridin-4-yl)-2H-benzo[d][1,2,3]triazol-4-yl)benzene (Example 29), deep-red crystals, 250 mg (69%). 1H NMR (400 MHz, CDCl$_3$): δ 8.84 (m, 4H, pyridine), 8.40 (m, 4H, pyridine), 8.35 (s, 4H, benzene), 8.09 (d, J=8.8 Hz, 4H, phenylene), 7.84 (d, J=7.7 Hz, 2H, benzotriazole), 7.74 (d, J=7.3 Hz, 2H, benzotriazole), 7.30 (m, 8H, Ph), 7.22 (m, 12H, p-phenylene and Ph), 7.09 (tt, J=7.3 and 2.2 Hz, 4H, Ph). UV-vis spectrum (dichloromethane): $\lambda_{max}$=451 nm. Fluorimetry (dichloromethane): $\lambda_{max}$=587 nm.

Example 30

A mixture of Intermediate F (80%, 182 mg, 0.29 mmol), sodium carbonate (1.06 g, 10 mmol) in water (5 mL), (2,4-dimethoxyphenyl)boronic acid (364 mg, 2.00 mmol), tetrakis (triphenylphosphine)palladium (0) (0.50 g, 0.43 mmol), n-butanol (20 mL), and toluene (20 mL) was stirred and heated under argon at 110° C. for 20 hours. The reaction mixture was poured into water (200 mL), treated with 5N NaOH (20 mL), stirred for 1 hour, and extracted with dichloromethane (2×100 mL). The volatiles were removed under reduced pressure, and the residue was chromatographed (silica gel, dichloromethane/tetrahydrofuran 1:1). The obtained product was triturated with hot ethanol (20 mL), cooled, and filtered off to give 1,4-bis(7-(2,4-dimethoxyphenyl)-2-(pyridin-4-yl)-2H-benzo[d][1,2,3]triazol-4-yl)benzene (Example 30), yellow crystals, 90 mg (42%). 1H NMR (400 MHz, CDCl$_3$): δ 8.80 (m, 4H, pyridine), 8.32-8.36 (m, 8H, pyridine and benzene), 7.80 (d, J=7.3 Hz, 2H, benzotriazole), 7.74 (d, J=8.1 Hz, 2H, 2,4-dimethoxyphenyl), 7.73 (d, J=7.3 Hz, 2H, benzotriazole), 6.71 (dd, J=8.1 and 2.5 Hz, 2H, 2,4-dimethoxyphenyl), 6.70 (bs, 2H, 2,4-dimethoxyphenyl), 3.93 (s, 6H, methanol), 3.88 (s, 6H, methanol). UV-vis spectrum (dichloromethane): $\lambda_{max}$=403 nm. Fluorimetry (dichloromethane): $\lambda_{max}$=506 nm.

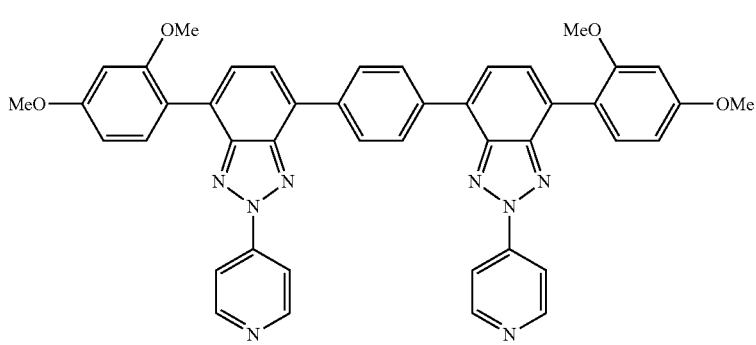

Example 31

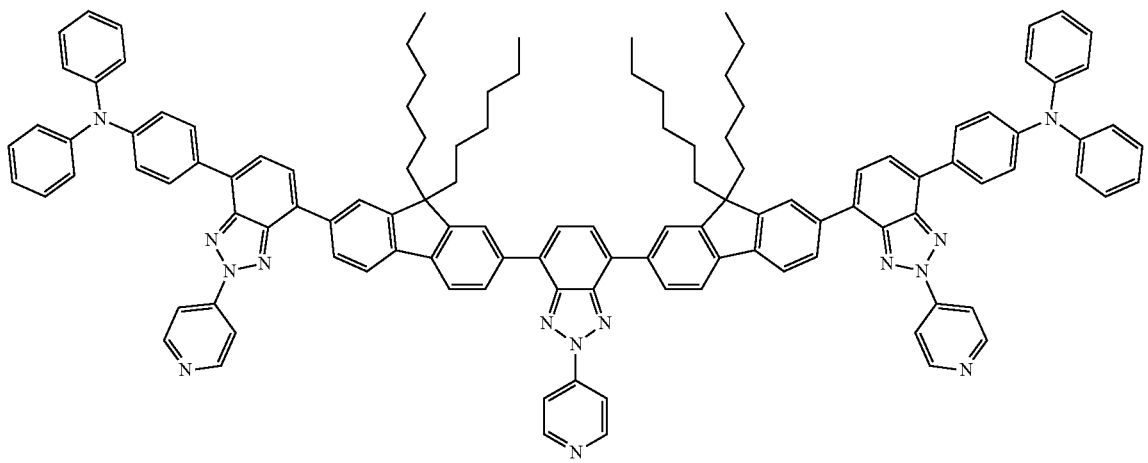

31

A mixture of Intermediate F (purity 80%, 703 mg, 0.4 mmol), sodium carbonate (530 mg, 5 mmol) in water (3 mL), 4-(diphenylamino)phenylboronic acid (463 mg, 1.6 mmol), tetrakis(triphenylphosphine)palladium (0) (240 mg, 0.2 mmol), n-butanol (20 mL), and toluene (30 mL) was stirred and heated under argon at 110° C. for 48 hours. The reaction mixture was poured into water (200 mL), treated with 5N NaOH (20 mL), stirred for 30 minutes, and extracted with chloroform (2×100 mL). The volatiles were removed under reduced pressure and the residue was subjected to column chromatography using silica gel and dichloromethane/tetrahydrofuran (3:1) as the eluent. The obtained product was further purified by recrystallization from acetone to give Example 31, yellow crystals, 420 mg (60%). $^1$H NMR (400 MHz, CDCl$_3$): δ 8.83 (m, 6H, pyridine), 8.37-8.41 (m, 6H, pyridine), 8.23 (s, 2H, fluorene), 8.22 (s, 2H, fluorene), 8.16 (m, 4H, fluorene), 8.09 (d, J=8.4 Hz, 4H, p-phenylene), 7.88 (s, 2H, benzotriazole), 7.82 (d, J=7.6 Hz, 2H, benzotriazole), 7.75 (d, J=7.6 Hz, 2H, benzotriazole), 7.30 (m, 8H, Ph), 7.22 (m, 12H, p-phenylene and Ph), 7.10 (t, J=7.3 and, 4H, Ph), 2.20 (m, 8H, hexyl), 1.14-1.21 (m, 24H, hexyl), 0.96 (m, 8H, hexyl), 0.73 (t, J=6.6 Hz, 12H, hexyl). UV-vis spectrum (dichloromethane): $\lambda_{max}$=452 nm. Fluorimetry (dichloromethane): $\lambda_{max}$=590 nm.

Example 32

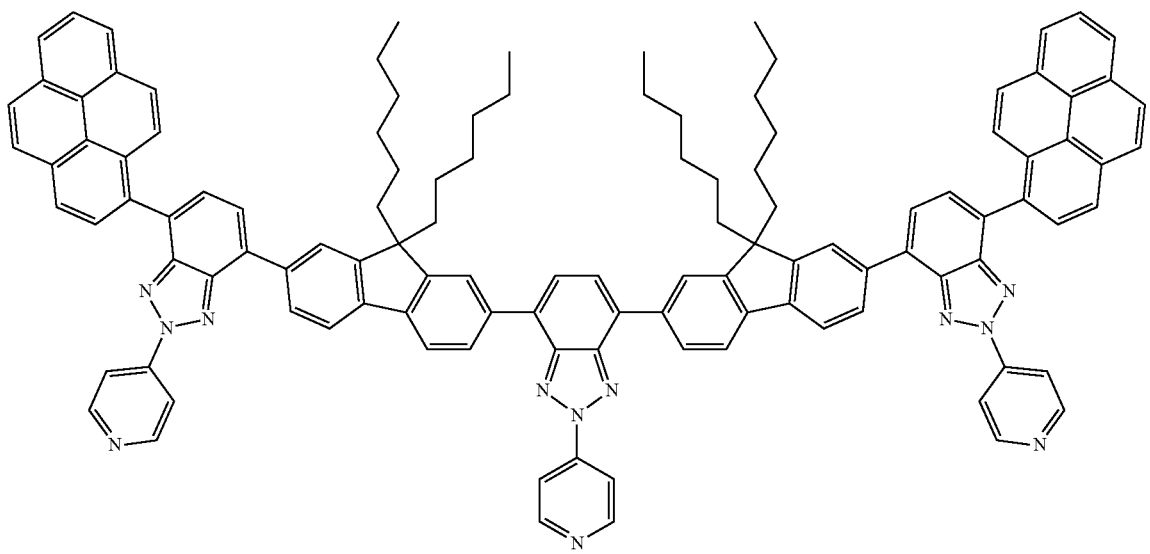

32

A mixture of Intermediate F (purity 60%, 1.40 g, 0.6 mmol), pyrene-1-boronic acid (0.98 g, 4.0 mmol), sodium carbonate (1.06 g, 10 mmol) in water (5 mL), tetrakis(triphenylphosphine)palladium (0) (0.48 g, 0.4 mmol), n-butanol (30 mL), and toluene (20 mL) was stirred and heated under argon at 100° C. for 48 hours. The reaction mixture was poured into water (200 mL), treated with 5N NaOH (20 mL), diluted with dichloromethane (100 mL), stirred for 1 hour, and extracted with chloroform (2×200 mL). The volatiles were removed under reduced pressure and the residue was subjected to column chromatography using silica gel and dichloromethane/ethyl acetate/triethylamine/methanol (50:43:5:2) as an eluent. The obtained product was further purified by recrystallization from toluene/ethyl acetate (10+10 mL) to give Example 32, orange crystals, 580 mg (58%). 1H NMR (400 MHz, CDCl$_3$): δ 8.86 (m, 2H, pyridine), 8.73 (m, 4H, pyridine), 8.41 (m, 2H, pyridine), 8.35 (d, J=8.1 Hz, 2H), 8.31 (m, 2H), 8.29 (d, J=7.7 Hz, 2H), 8.16-8.27 (m, 10H), 8.00-8.07 (m, 8H), 7.98 (d, J=6.9 Hz, 2H), 7.91 (s, 2H, benzotriazole), 7.82 (d, J=7.3 Hz, 2H, benzotriazole), 2.24 (m, 8H, hexyl), 1.23 (m, 8H, hexyl), 1.17 (m, 16H, hexyl), 1.01 (m, 8H, hexyl), 0.77 (t, J=6.6 Hz, 12H, hexyl).

Intermediate H

Common Intermediate H is synthesized in a two step process.

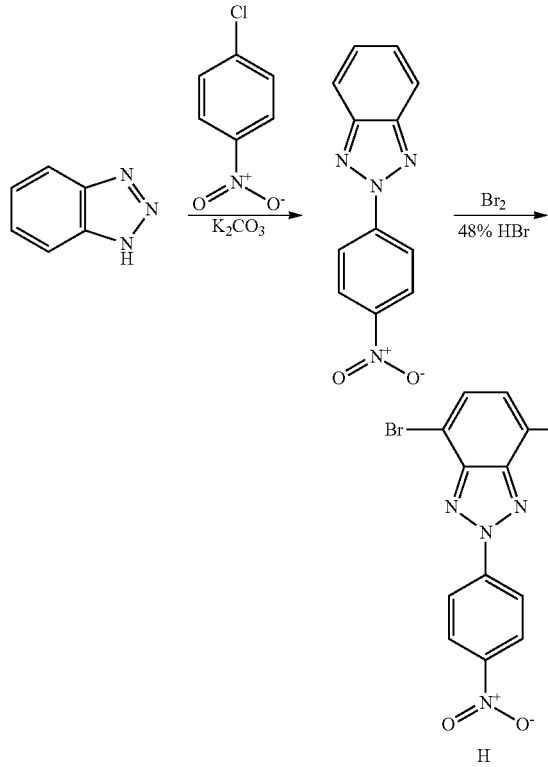

Step 1: Synthesis of 2-(4-Nitrophenyl)-2H-benzo[d][1,2,3]triazole

A mixture of 4-chloronitrobenzene (55.0 g, 349 mmol), benzotriazole (50.0 g, 420 mmol), potassium carbonate (200 g, 500 mmol), and NMP (500 mL) was stirred and heated under argon at 130° C. for 5 hours. Progress of the reaction was monitored by thin layer chromatography. The reaction mixture was poured onto crushed ice (2 kg). After all ice melted, the solid was filtered off and washed with water (200 mL). The product was suspended in methanol (1.5 L) and stirred for 30 minutes. The crystals were filtered off and dried in a vacuum oven. Column chromatography of the obtained material using silica gel and hot solution of ethyl acetate (1%) in toluene as an eluent gave 2-(4-nitrophenyl)-2H-benzo[d][1,2,3]triazole (24.24 g, 30% yield). $^1$H NMR (400 MHz, CDCl$_3$): δ 8.57 (d, J=9.2 Hz, 2H, 4-nitrophenyl), 8.44 (d, J=9.2 Hz, 2H, 4-nitrophenyl), 7.93 (m, 2H, benzotriazole), 7.47 (m, 2H, benzotriazole).

Step 2: Synthesis of 4,7-Dibromo-2-(4-nitrophenyl)-2H-benzo[d][1,2,3]triazole (Intermediate H)

A mixture of 2-(4-nitrophenyl)-2H-benzo[d][1,2,3]triazole (7.70 g, 31.2 mmol), bromine (4.8 mL, 94 mmol) and 48% HBr (120 mL) was heated at 130° C. for 20 hours under a reflux condenser connected with an HBr trap. The reaction mixture was poured onto crushed ice (800 g), decolorized with 5% solution of Na$_2$SO$_3$, and set aside at room temperature for 2 hours. The precipitate was filtered off, washed with water (200 mL) followed by 2% NaHCO$_3$ (200 mL) and again water (200 mL). The material was dried in a vacuum oven to give 4,7-dibromo-2-(4-nitrophenyl)-2H-benzo[d][1,2,3]triazole (Intermediate H, 13.47 g) of purity 90%. Yield 97%. $^1$H NMR (400 MHz, CDCl$_3$): δ 8.65 (m, 2H, 4-nitrophenyl), 8.44 (m, 2H, 4-nitrophenyl), 7.54 (s, 2H, benzotriazole).

Intermediate I

Intermediate I was synthesized using the following reaction scheme.

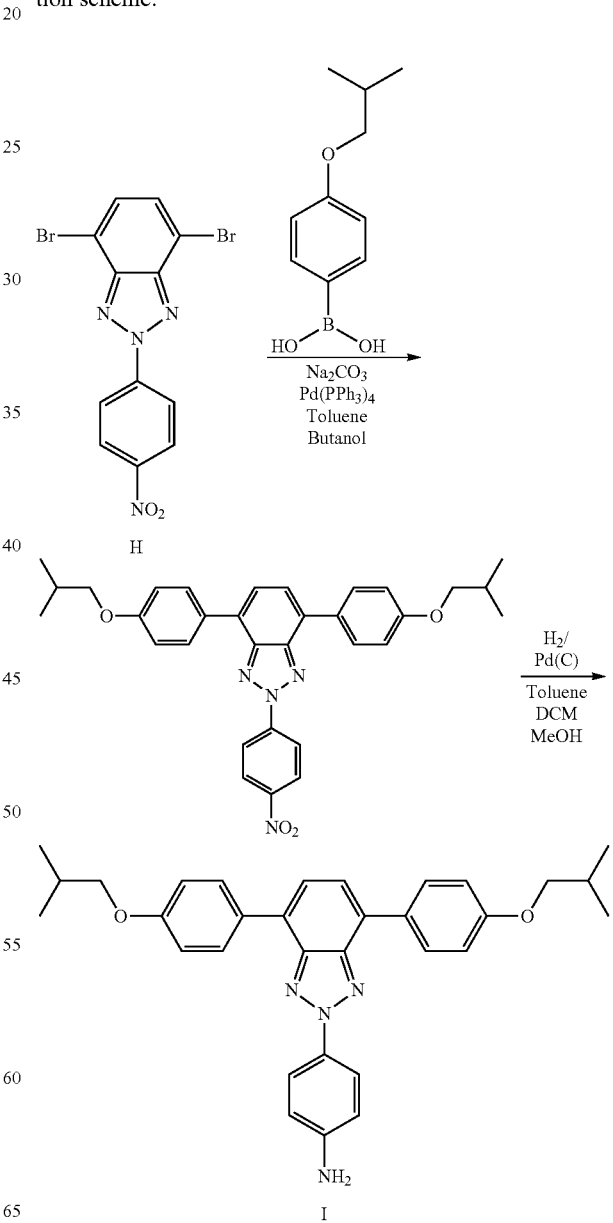

A mixture of Intermediate H (3.98 g, 10.0 mmol), 4-isobutoxyphenylboronic acid (5.00 g, 25.7 mmol), sodium carbonate (5.30 g, 50 mmol) in water (40 mL), tetrakis(triphenylphosphine)palladium(0) (2.00 g), n-butanol (60 mL), and toluene (30 mL) was stirred under argon and heated at 100° C. for 4 hours. The reaction mixture was poured into water (200 mL), stirred for 30 minutes and extracted with toluene (500 mL). The extract was washed with water (200 mL), concentrated to a volume of 100 mL and diluted with dichloromethane (200 mL) and methanol (200 mL). The obtained solution was hydrogenated for 20 minutes at 50 psi over 10% Pd/C (2 g), filtered through a layer of Celite, and the solvent was removed under reduced pressure. The residue was chromatographed (silica gel, hexane/dichloromethane/ethyl acetate, 35:50:5) to give 4,7-Bis(4-isobutoxyphenyl)-2-(4-aminophenyl)-2H-benzo[d][1,2,3]triazole (Intermediate I) (3.80 g, 75%). 1H NMR (400 MHz, CDCl$_3$): δ 8.22 (d, J=8.4 Hz, 2H, 4-aminophenyl), 8.09 (d, J=8.7 Hz, 4H, 4-i-BuOC$_6$H$_4$), 7.57 (s, 2H, benzotriazole), 7.06 (d, J=8.7 Hz, 4H, 4-i-BuOC$_6$H$_4$), 6.79 (d, J=8.5 Hz, 2H, 4-aminophenyl), 3.90 (bs, 2H, NH$_2$), 3.81 (d, J=6.6 Hz, 4H, i-BuO), 2.14 (m, 2H, i-BuO), 1.06 (d, J=7.0 Hz, 12H, i-BuO).

Intermediate J

Intermediate J was synthesized using the following reaction scheme.

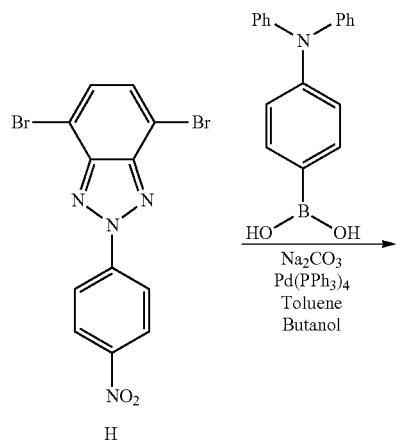

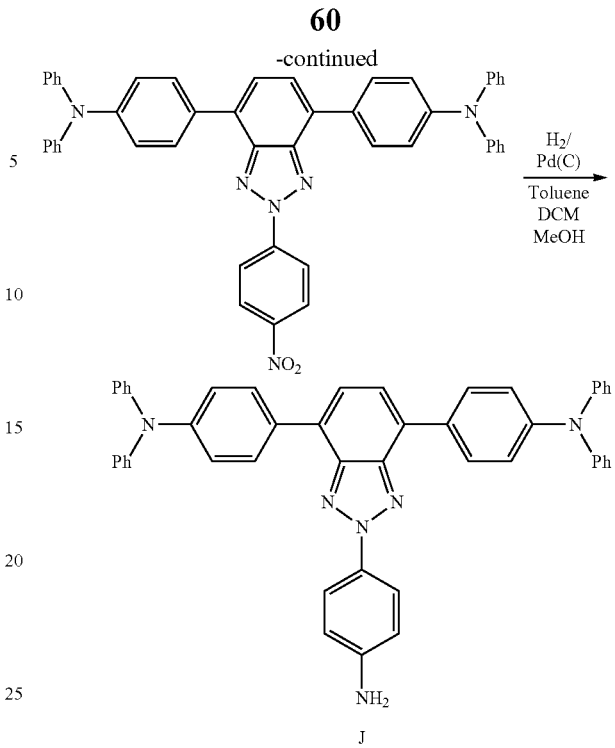

Starting from Intermediate H and 4-N,N-diphenylaminophenylboronic acid, and applying a procedure similar to the above, 4,7-Bis(4-N,N-diphenylaminophenyl)-2-(4-aminophenyl)-2H-benzo[d][1,2,3]triazole (Intermediate J) was obtained in 74% yield. $^1$H NMR (400 MHz, CDCl$_3$): δ 8.21 (d, J=8.8, 2H, 4-aminophenyl), 8.09 (d, J=8.8 Hz, 4H, 4-Ph$_2$NC$_6$H$_4$), 7.62 (s, 2H, benzotriazole), 7.28 (m, 8H, Ph), 7.22 (d, J=8.8 Hz, 4H, 4-Ph$_2$NC$_6$H$_4$), 7.19 (m, 8H, Ph), 7.05 (tt, 4H, J=7.3 and 1.1 Hz, Ph), 6.78 (d, J=8.8 Hz, 2H, 4-aminophenyl), 3.90 (bs, 2H, NH$_2$).

Example 33

Example Compound 33 was synthesized according to the following reaction scheme.

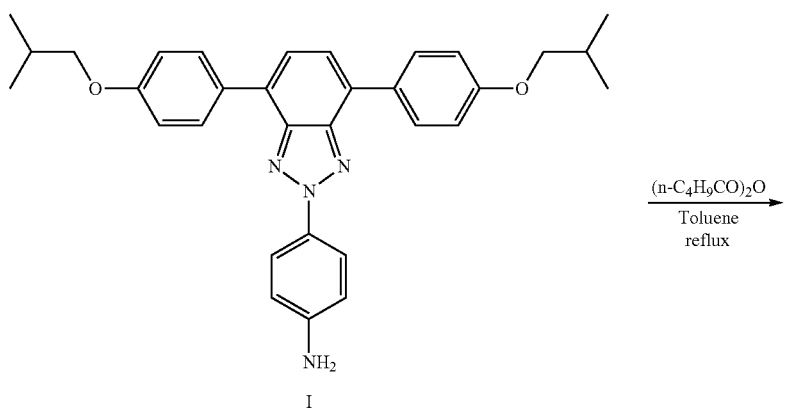

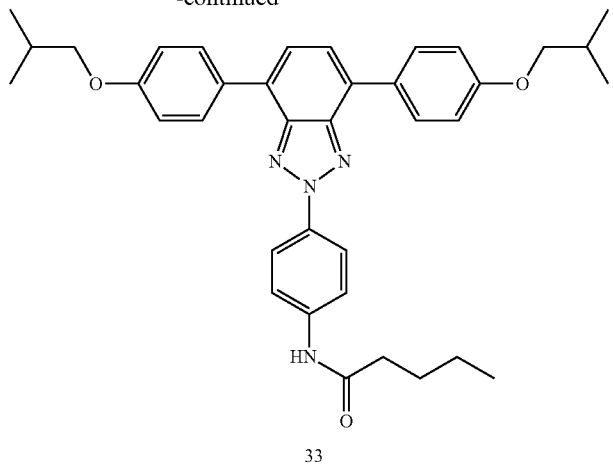

A mixture of Intermediate I (506 mg, 1.0 mmol), pentanoic anhydride (0.79 mL, 4.0 mmol), and toluene (10 mL) was heated under argon at 120° C. for 1 hour. The reaction mixture was chromatographed (silica gel, hexane/dichloromethane/ethyl acetate, 37:60:3), and the separated product was recrystallized from ethanol to give pure N-(4-(4,7-bis-4-isobutoxyphenyl-2H-benzo[d][1,2,3]triazol-2-yl)phenyl) pentanamide (Compound 33), yellow crystals, 350 mg (59%). %). $^1$H NMR (400 MHz, CDCl$_3$): δ 8.40 (d, J=9.1 Hz, 2H, 4-amidophenyl), 8.09 (d, J=8.8 Hz, 4H, 4-i-BuOC$_6$H$_4$), 7.72 (d, J=9.1 Hz, 2H, 4-amidophenyl), 7.60 (s, 2H, benzotriazole), 7.07 (d, J=8.8 Hz, 4H, 4-i-BuOC$_6$H$_4$), 3.82 (d, J=6.3 Hz, 4H, i-BuO), 2.41 (t, J=7.3 Hz, 2H, n-BuCO), 2.14 (m, 2H, i-BuO), 1.75 (quintet, J=7.7 Hz, 2H, n-BuCO), 1.43 (sextet, J=7.3 Hz, 2H, n-BuCO), 1.06 (d, J=7.0 Hz, 12H, i-BuO), 0.97 (t, J=7.3 Hz, 3H, n-BuCO). UV-vis spectrum (PVB): λ$_{max}$=394 nm. Fluorimetry (PVB): λ$_{max}$=468 nm.

Example 34

Example Compound 34 was synthesized according to the following reaction scheme.

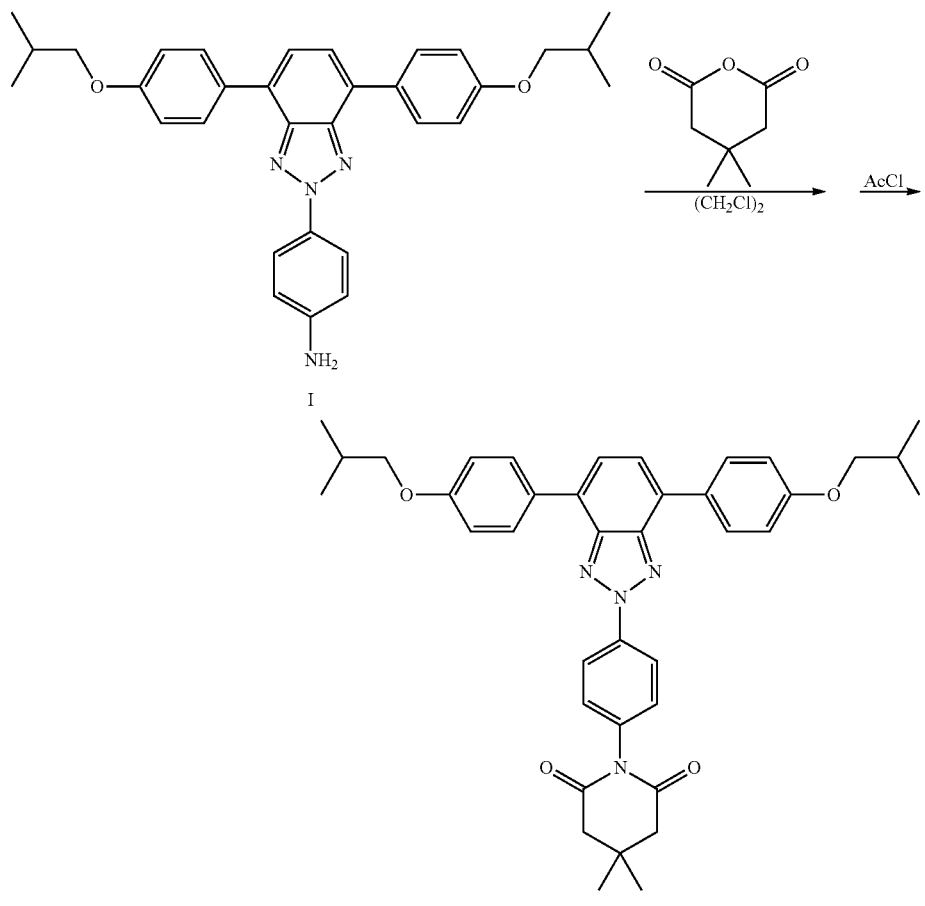

A solution of intermediate I (0.92 g, 1.82 mmol), 3,3-dimethylglutaric anhydride (284 mg, 2.0 mmol) in 1,2-dichloroethane (20 mL) was heated under a reflux condenser at 80° C. for 20 hours. After cooling to room temperature, acetyl chloride (0.28 mL, 4.0 mmol) was added, and the mixture was heated at 80° C. for 1 hour. The reaction mixture was diluted with dichloromethane (200 mL) and washed with saturated NaHCO$_3$ (100 mL). The solution was dried over MgSO$_4$, and the volatiles were removed under reduced pressure. The crude product was purified by column chromatography (silica gel, hexane/dichloromethane/ethyl acetate, 37:60:3) and crystallization from ethanol to give 1-(4-(4,7-bis(4-isobutoxyphenyl)-2H-benzo[d][1,2,3]triazol-2-yl)phenyl)-4,4-dimethylpiperidine-2,6-dione (Compound 34, 551 mg, 48% yield) as thin yellow needles. H NMR (400 MHz, CDCl$_3$): δ 8.53 (d, J=8.8 Hz, 2H, 4-imidophenyl), 8.08 (d, J=8.8 Hz, 4H, 4-i-BuOC$_6$H$_4$), 7.61 (s, 2H, benzotriazole), 7.26 (d, J=8.8 Hz, 2H, 4-imidophenyl), 7.07 (d, J=8.8 Hz, 4H, 4-i-BuOC$_6$H$_4$), 3.82 (d, J=6.6 Hz, 4H, i-BuO), 2.72 (s, 4H, 4,4-dimethylpiperidine-2,6-dione), 2.14 (m, 2H, i-BuO), 1.24 (s, 6H, 4,4-dimethylpiperidine-2,6-dione), 1.06 (d, J=7.0 Hz, 12H, i-BuO). UV-vis spectrum (PVB): $\lambda_{max}$=388 nm. Fluorimetry (PVB): $\lambda_{max}$=478 nm.

Example 35

Example Compound 35 was synthesized according to the following reaction scheme.

A mixture of Intermediate I (1.13 g, 2.0 mmol), 1,2-cyclohexanedicarboxylic anhydride (339 mg, 2.2 mmol) and dry chlorobenzene (20 mL) was heated under argon at 130° C. for 4 hours. After cooling, the mixture was diluted with dichloromethane/hexane (2:1, 75 mL) and chromatographed (silica gel, hexane/dichloromethane/ethyl acetate, 37:60:3). Triturating of the separated material with hot acetone (20 mL) and cooling resulted in yellow crystals of 2-(4-(4,7-bis(4-isobutoxyphenyl)-2H-benzo[d][1,2,3]triazol-2-yl)phenyl)hexahydro-1H-isoindole-1,3(2H)-dione (Compound 35, 632 mg, 49% yield). $^1$H NMR (400 MHz, CDCl$_3$): δ 8.55 (d, J=8.8 Hz, 2H, 4-imidophenyl), 8.08 (d, J=8.8 Hz, 4H, 4-i-BuOC$_6$H$_4$), 7.61 (s, 2H, benzotriazole), 7.53 (d, J=8.8 Hz, 2H, 4-imidophenyl), 7.08 (d, J=8.8 Hz, 4H, 4-i-BuOC$_6$H$_4$), 3.82 (d, J=6.3 Hz, 4H, i-BuO), 3.08 (m, 2H, hexahydro-1H-isoindole-1,3(2H)-dione), 2.14 (m, 2H, i-BuO), 1.94 (m, 4H, hexahydro-1H-isoindole-1,3(2H)-dione), 1.51 (m, 4H, hexahydro-1H-isoindole-1,3(2H)-dione), 1.06 (d, J=6.6 Hz, 12H, i-BuO). UV-vis spectrum (PVB): $\lambda_{max}$=390 nm. Fluorimetry (PVB): $\lambda_{max}$=475 nm.

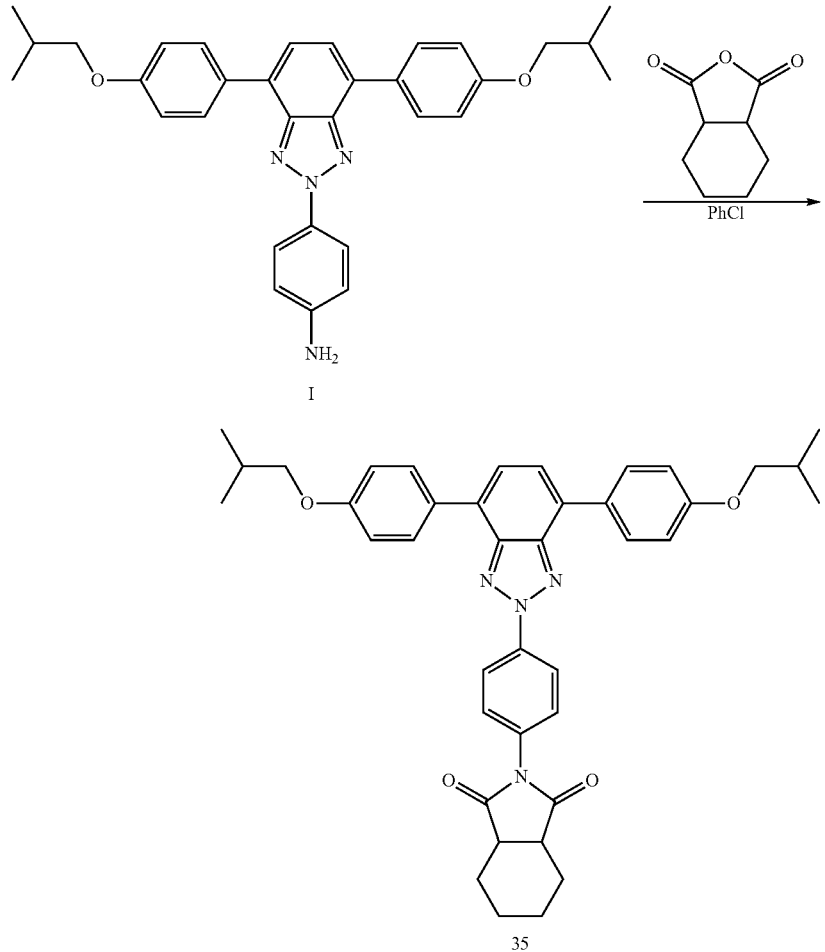

Examples 36

Example Compound 36 was synthesized according to the following reaction scheme.

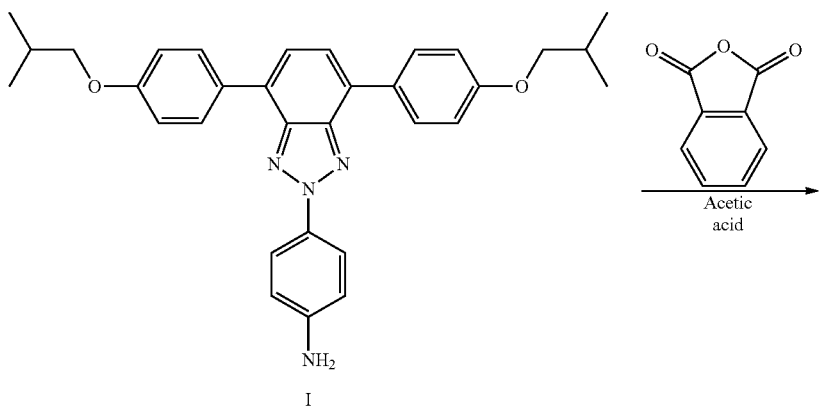

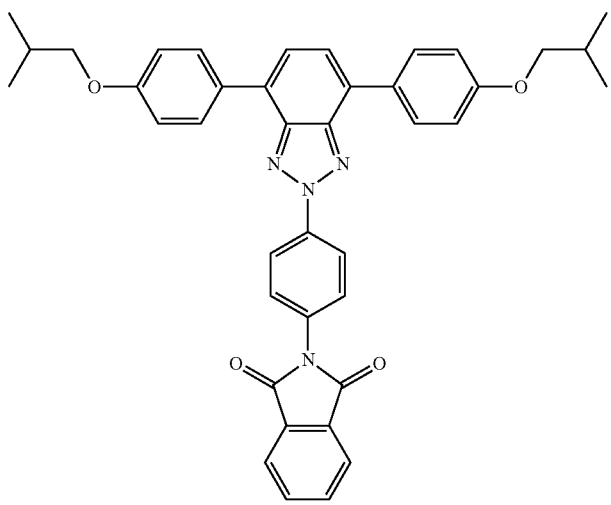

A mixture of Intermediate I (506 mg, 1.0 mmol), phthalic anhydride (339 mg, 2.2 mmol) and acetic acid (10 mL) was heated under argon at 120° C. for 16 hours. The reaction mixture was poured into water (200 mL), diluted with dichloromethane (200 mL), stirred and treated with 5 N NaOH to pH 10. After 30 minutes of stirring, the dichloromethane layer was separated, and the aqueous layer was washed with dichloromethane. The combined dichloromethane solutions were dried over anhydrous sodium sulfate, concentrated and chromatographed (silica gel, hexane/dichloromethane/ethyl acetate, 35:60:5). Triturating of the separated material with hot acetone (20 mL) and cooling resulted in yellow crystals of 2-(4-(4,7-bis(4-isobutoxyphenyl)-2H-benzo[d][1,2,3]triazol-2-yl)phenyl)-1H-isoindole-1,3 (2H)-dione (Compound 36, 296 mg, 46% yield). $^1$H NMR (400 MHz, CDCl$_3$): δ 8.60 (d, J=8.8 Hz, 2H, 4-imidophenyl), 8.10 (d, J=8.8 Hz, 4H, 4-i-BuOC$_6$H$_4$), 7.99 (m, 2H, phthalimide), 7.83 (m, 2H, phthalimide), 7.69 (d, J=8.8 Hz, 2H, 4-imidophenyl), 7.62 (s, 2H, benzotriazole), 7.08 (d, J=8.8 Hz, 4H, 4-i-BuOC$_6$H$_4$), 3.82 (d, J=6.2 Hz, 4H, i-BuO), 2.14 (m, 2H, i-BuO), 1.06 (d, J=6.6 Hz, 12H, i-BuO). UV-vis spectrum (PVB): $\lambda_{max}$=389 nm. Fluorimetry (PVB): $\lambda_{max}$=476 nm.

Example 37

Example Compound 37 was synthesized according to the following reaction scheme.

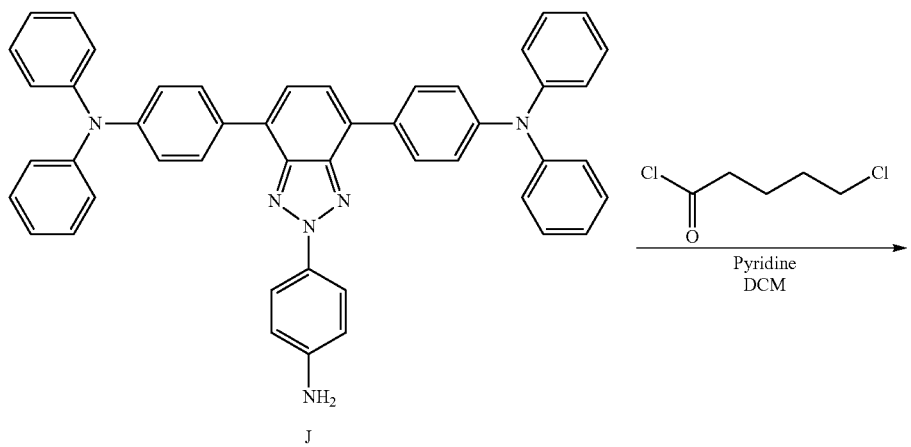

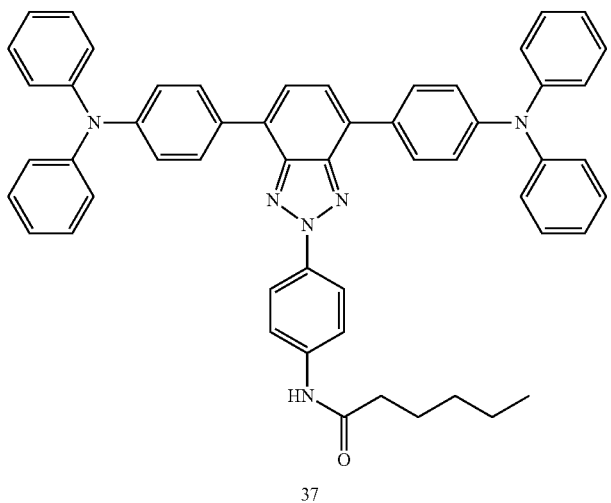

A solution of Intermediate J (430 mg, 0.59 mmol), hexanoyl chloride (0.50 mL, 3.58 mmol) and pyridine (1.0 mL, 12.4 mmol) in dichloromethane (15 mL) was stirred at 20° C. for 20 hours. The reaction mixture was poured into water (200 mL), treated with 5% $NaHCO_3$ to pH 8, stirred for 30 minutes, and extracted with dichloromethane (2×100 mL). The extract was washed with 10% ammonium chloride (50 mL), dried over anhydrous magnesium sulfate, and the solvent was evaporated. The residue was chromatographed (silica gel, hexane/dichloromethane/ethyl acetate, 48:50:2). The obtained product was triturated with hot ethanol (10 mL) and the suspension was set aside at room temperature for 1 hour. The orange crystals were filtered off and dried in a vacuum oven to give N-(4-(4,7-bis(4-diphenylamino)phenyl-2H-benzo[d][1,2,3]triazol-2-yl)phenyl)hexanamide (Compound 37, 395 mg, 84% yield). $^1$H NMR (400 MHz, $CDCl_3$): δ 8.38 (d, J=8.8, 2H, 4-amidophenyl), 8.08 (d, J=8.8 Hz, 4H, 4-$Ph_2NC_6H_4$), 7.71 (d, J=8.8 Hz, 2H, 4-aminophenyl), 7.64 (s, 2H, benzotriazole), 7.28 (m, 8H, Ph), 7.22 (d, J=8.8 Hz, 4H, 4-$Ph_2NC_6H_4$), 7.19 (m, 8H, Ph), 7.06 (tt, J=7.5 and 1.1 Hz, 4H, Ph), 2.39 (t, J=7.4 Hz, 2H, hexanoyl), 1.75 (m, 2H, hexanoyl), 1.37 (m, 4H, hexanoyl), 0.92 (t, J=7.0 Hz, 3H, hexanoyl). UV-vis spectrum (PVB): $\lambda_{max}$=436 nm. Fluorimetry (PVB): $\lambda_{max}$=521 nm.

Examples 38 and 39
Example Compound 38 and Compound 39 were synthesized according to the following reaction scheme.
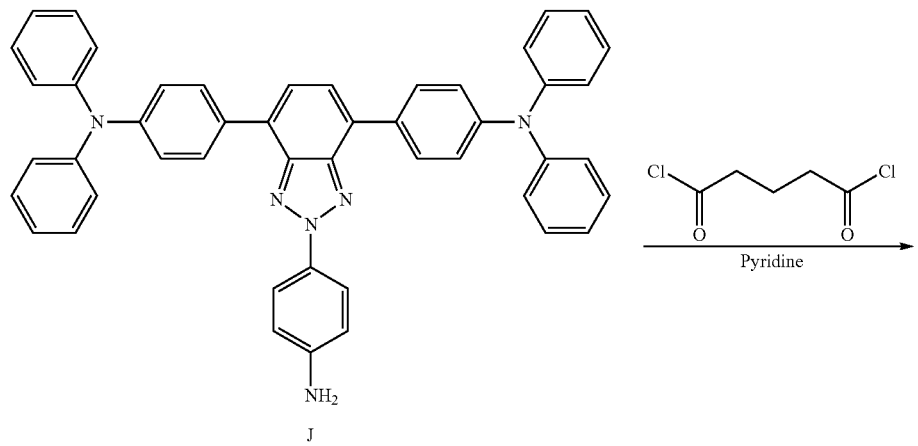
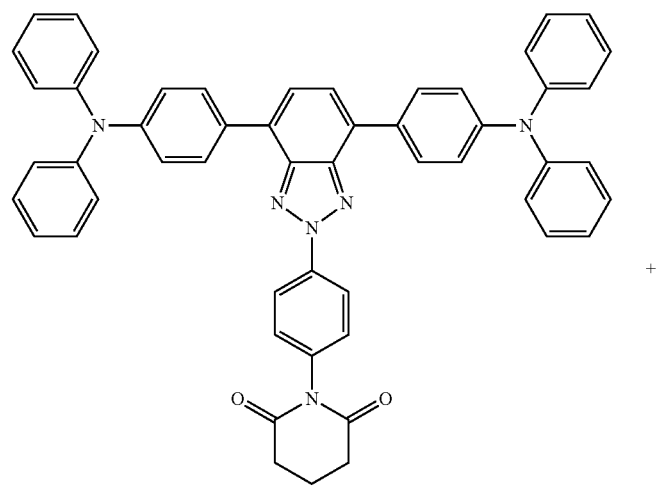

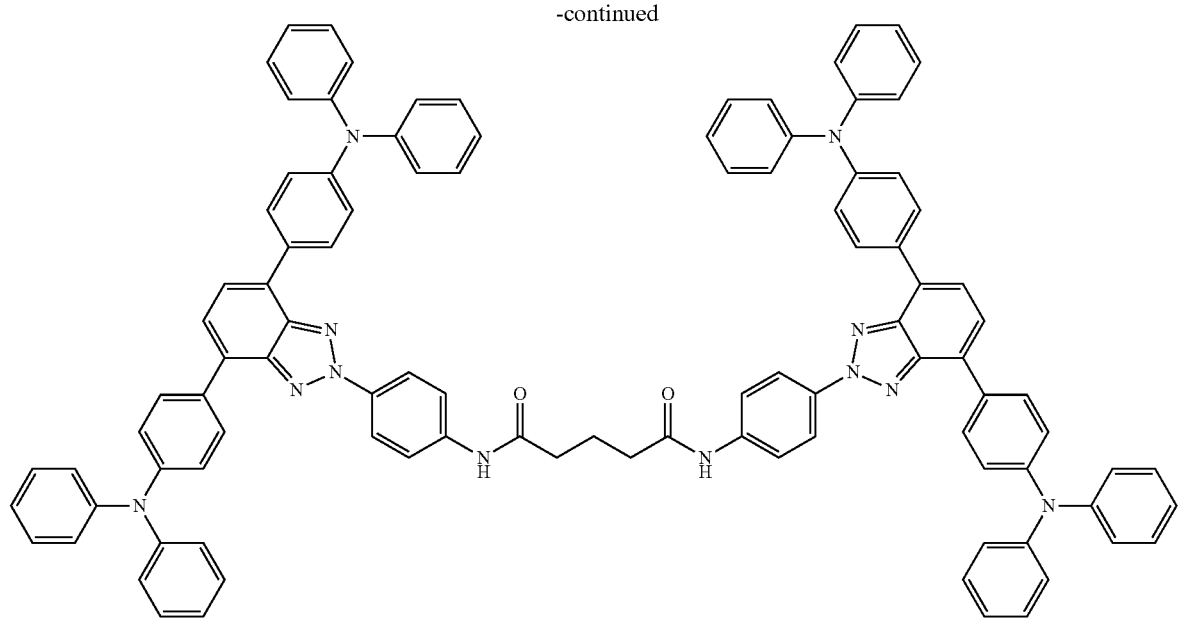

39

A mixture of Intermediate J (1.39 g, 2.0 mmol), glutaryl chloride (0.32 mL, 2.5 mmol) and pyridine (10 mL) was stirred under argon and heated at 100° C. for 16 hours. The reaction mixture was poured into water (100 mL), treated with 5% NaHCO₃ (100 mL), heated to 80° C., and stirred for 30 minutes. The obtained precipitate was filtered off, washed with water (50 mL) followed by methanol (50 mL) and dried in a vacuum oven. The crude product was chromatographed (silica gel, dichloromethane/ethyl acetate, 9:1) to give, as the first fraction, 1-(4-(4,7-bis(4-diphenylaminophenyl)-2H-benzo[d][1,2,3]triazol-2-yl)phenyl)piperidine-2,6-dione (Compound 38, 201, 25% yield). $^1$H NMR (400 MHz, CDCl₃): δ 8.53 (d, J=8.8, 2H, 4-imidophenyl), 8.08 (d, J=8.8 Hz, 4H, 4-Ph₂NC₆H₄), 7.65 (s, 2H, benzotriazole), 7.28 (m, 8H, Ph), 7.18-7.32 (m, 14H), 7.06 (tt, J=7.3 and 1.1 Hz, 4H, Ph), 2.86 (t, J=6.4 Hz, 4H, piperidine-2,6-dione), 2.14 (m, 2H, piperidine-2,6-dione). UV-vis spectrum (PVB): $\lambda_{max}$=440 nm. Fluorimetry (PVB): $\lambda_{max}$=529 nm.

The second fraction from chromatography gave chromophore Compound 39 (770 mg, 52% yield). $^1$H NMR (400 MHz, CDCl₃): δ 8.39 (d, J=8.7 Hz, 4H, 4-amidophenyl), 8.07 (d, J=8.8 Hz, 8H, 4-Ph₂NC₆H₄), 7.90 (bs, 2H, NH), 7.73 (d, J=9.2 Hz, 4H, 4-amidophenyl), 7.63 (s, 4H, benzotriazole), 7.28 (m, 16H, Ph), 7.21 (d, J=8.8 Hz, 8H, 4-Ph₂NC₆H₄), 7.18 (m, 16H, Ph), 7.05 (t, J=7.3 Hz, 8H, Ph), 2.58 (t, J=6.6 Hz, 4H, glutaryl), 2.17 (m, 2H, glutaryl). UV-vis spectrum (PVB): $\lambda_{max}$=435 nm. Fluorimetry (PVB): $\lambda_{max}$=527 nm.

Examples 40 and 41

Example Compound 40 and Compound 41 were synthesized according to the following reaction scheme.

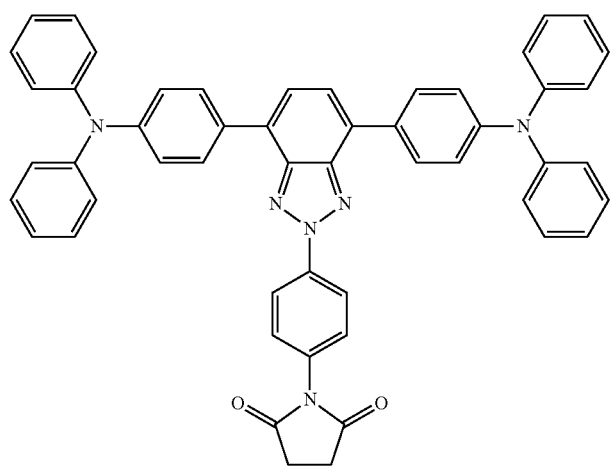

40

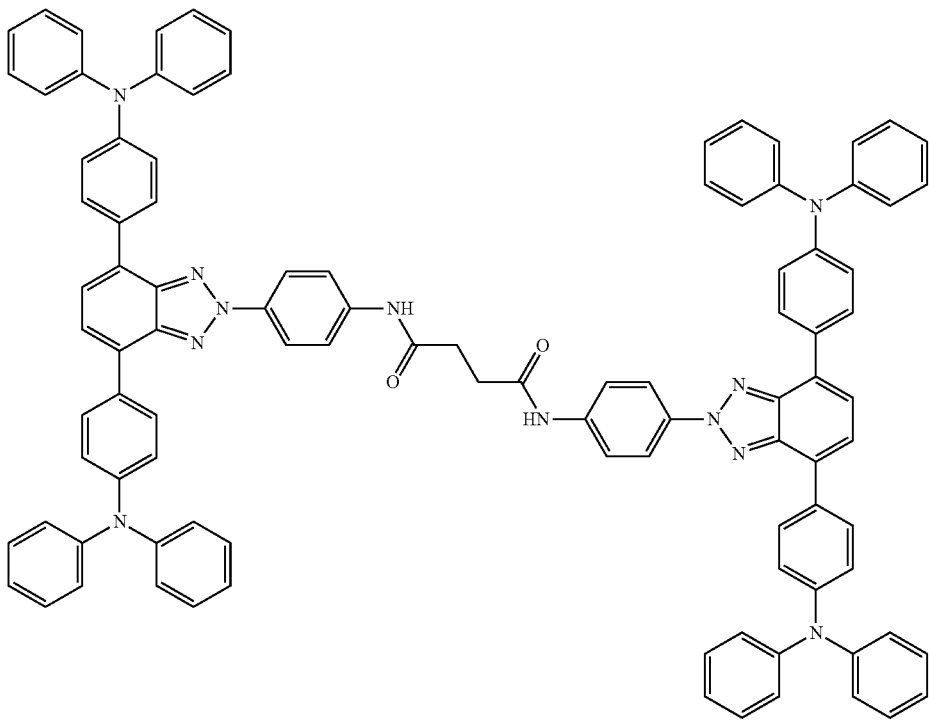

41

A mixture of Intermediate J (700 mg, 1.0 mmol), succinic anhydride (110 mg, 1.1 mmol) and acetic acid (10 mL) was heated under argon at 120° C. for 24 hours. The reaction mixture was poured into water (100 mL) and stirred for 30 minutes. The precipitate was filtered off, dried in vacuum oven and subjected to column chromatography. The material obtained from the first fraction was triturated with hot ethanol (10 ml), the suspension was set aside at room temperature for 2 hours, and the crystals were filtered off and dried in a vacuum oven to give 1-(4-(4,7-bis(4-diphenylaminophenyl)-2H-benzo[d][1,2,3]triazol-2-yl)phenyl)pyrrolidine-2,5-dione (Compound 40, 98 mg, 13% yield). $^1$H NMR (400 MHz, CDCl$_3$): δ 8.56 (d, J=9.3, 2H, 4-imidophenyl), 8.07 (d, J=8.8 Hz, 4H, 4-Ph$_2$NC$_6$H$_4$), 7.66 (s, 2H, benzotriazole), 7.51 (d, J=8.8 Hz, 2H, 4-imidophenyl) 7.30 (m, 8H, Ph), 7.22 (d, J=8.8 Hz, 4H, 4-Ph$_2$NC$_6$H$_4$) 7.19 (m, 8H, pH), 7.06 (tt, J=7.5 and 1.1 Hz, 4H, Ph), 2.94 (s, 4H, pyrrolidine-2,5-dione). UV-vis spectrum (PVB): $\lambda_{max}$=441 nm. Fluorimetry (PVB): $\lambda_{max}$=532 nm.

The second fraction from chromatography gave chromophore Compound 41 (85 mg, 12% yield). $^1$H NMR (400 MHz, CDCl$_3$): δ 8.39 (d, J=9.1, 4H, 4-amidophenyl), 8.08 (d, J=8.8 Hz, 8H, 4-Ph$_2$NC$_6$H$_4$), 7.69 (d, J=8.8 Hz, 4H, 4-aminophenyl), 7.64 (s, 4H, benzotriazole), 7.29 (m, 16H, Ph), 7.22 (d, J=8.8 Hz, 8H, 4-Ph$_2$NC$_6$H$_4$), 7.19 (m, 16H, Ph), 7.06 (tt, J=7.5 and 1.1 Hz, 8H, Ph), 2.22 (s, 4H, succinyl). UV-vis spectrum (PVB): $\lambda_{max}$=436 nm. Fluorimetry (PVB): $\lambda_{max}$=527 nm.

Intermediate K

Common Intermediate A was synthesized according to the following scheme.

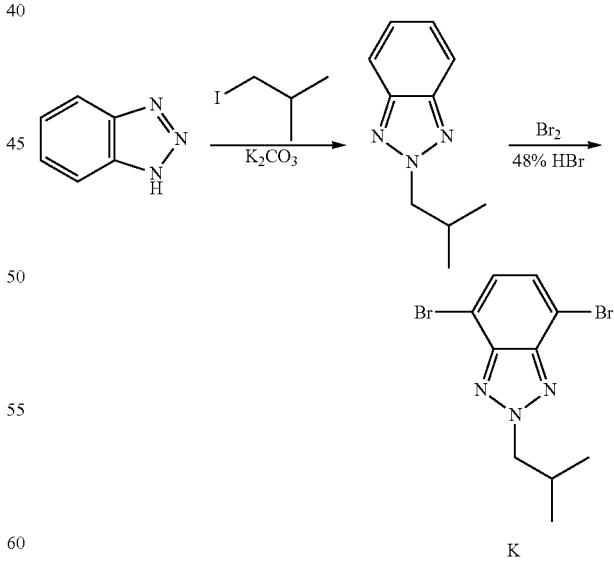

Step 1: 2-Isobutyl-2H-benzo[d][1,2,3]triazole

A mixture of benzotriazole (11.91 g, 100 mmol), 1-iodo-2-methylpropane (13.8 mL, 120 mmol), potassium carbonate (41.46 g, 300 mmol), and dimethylformamide (200 mL) was stirred and heated under argon at 40° C. for 2 days. The reaction mixture was poured into ice/water (1 L) and extracted with toluene/hexanes (2:1, 2×500 mL). The extract was washed with 1 N HCl (2×200 mL) followed by brine (100 mL), dried over anhydrous magnesium sulfate, and the solvent was removed under reduced pressure. The residue was triturated with hexane (200 mL) and set aside at room temperature for 2 hours. The precipitate was separated and discarded, and the solution was filtered through a layer of silica gel (200 g). The silica gel was washed with hexane/dichloromethane/ethyl acetate (37:50:3, 2 L). The filtrate and washings were combined, and the solvent was removed under reduced pressure to give 2-isobutyl-2H-benzo[d][1,2,3]triazole (8.81 g, 50% yield) as an oily product. $^1$H NMR (400 MHz, CDCl$_3$): δ 7.86 (m, 2H, benzotriazole), 7.37 (m, 2H, benzotriazole), 4.53 (d, J=7.3 Hz, 2H, i-Bu), 2.52 (m, 1H, i-Bu), 0.97 (d, J=7.0 Hz, 6H, i-Bu).

Step 2:
4,7-Dibromo-2-isobutyl-2H-benzo[d][1,2,3]triazole (Intermediate K)

A mixture of 2-isobutyl-2H-benzo[d][1,2,3]triazole (8.80 g, 50 mmol), bromine (7.7 mL, 150 mmol) and 48% HBr (50 mL) was heated at 130° C. for 24 hours under a reflux condenser connected with an HBr trap. The reaction mixture was poured into ice/water (200 mL), treated with 5 N NaOH (100 mL) and extracted with dichloromethane (2×200 mL). The extract was dried over anhydrous magnesium sulfate, and the solvent was removed under reduced pressure. A solution of the residue in hexane/dichloromethane (1:1, 200 mL) was filtered through a layer of silica gel and concentrated to give 4,7-dibromo-2-isobutyl-2H-benzo[d][1,2,3]triazole, Intermediate K (11.14 g, 63% yield) as an oil that slowly solidified upon storage at room temperature. $^1$H NMR (400 MHz, CDCl$_3$): δ 7.44 (s, 2H, benzotriazole), 4.58 (d, J=7.3 Hz, 2H, i-Bu), 2.58 (m, 1H, i-Bu), 0.98 (d, J=6.6 Hz, 6H, i-Bu).

Intermediate L

Common Intermediate L was synthesized according to the following reaction scheme.

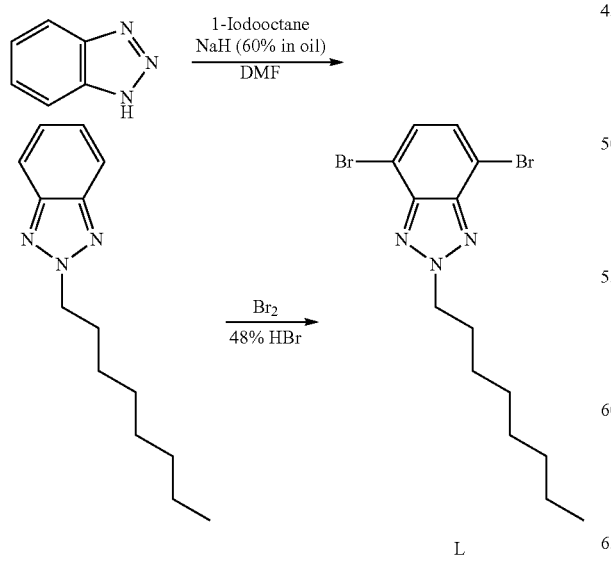

Step 1: 2-Octyl-2H-benzo[d][1,2,3]triazole

Sodium hydride (60% in oil, 4.00 g, 100 mmol) was added in small portions within 1 hours to a solution of benzotriazole (14.3 g, 120 mmol) and 1-iodooctane (25 g, 104 mmol) in anhydrous dimethylformamide (100 mL) stirred under argon at room temperature. After the addition, stirring was continued for 3 days. The reaction mixture was poured into ice/water (100 mL), treated with 2 N NaOH (100 mL) and extracted with hexane/ethyl ether (1:1, 3×200 mL). The extract was washed with water (200 mL), dried over anhydrous sodium carbonate, and the solvent was removed under reduced pressure. The residue was chromatographed using silica gel (500 g) and hexane/dichloromethane (1:1) as an eluent. The first fraction gave 2-octyl-2H-benzo[d][1,2,3]triazole (8.16 g, 35% yield) as an oily product. $^1$H NMR (400 MHz, CDCl$_3$): δ 7.85 (m, 2H, benzotriazole), 7.37 (m, 2H, benzotriazole), 4.71 (t, J=7.3 Hz, 2H, octyl), 2.10 (m, 2H, octyl), 1.32 (m, 4H, octyl), 1.23 (m, 6H, octyl), 0.85 (t, J=7.3 Hz, 3H, octyl).

Step 2:
4,7-Dibromo-2-octyl-2H-benzo[d][1,2,3]triazole (Intermediate L)

A mixture of 2-octyl-2H-benzo[d][1,2,3]triazole (8.16 g, 35.3 mmol), bromine (7.17 mL, 140 mmol) and 48% HBr (30 mL) was heated at 125° C. for 48 hours under a reflux condenser connected with an HBr trap. The reaction mixture was poured into ice/water (200 mL), treated with 5 N NaOH (100 mL) and extracted with dichloromethane (2×200 mL). The extract was dried over anhydrous magnesium sulfate, the solvent was removed under reduced pressure, and the residue was chromatographed (silica gel, hexane/dichloromethane, 3:1) to give 4,7-dibromo-2-octyl-2H-benzo[d][1,2,3]triazole, Intermediate L (7.83 g, 57% yield) as an oil. 1H NMR (400 MHz, CDCl$_3$): δ 7.43 (s, 2H, benzotriazole), 4.76 (t, J=7.3 Hz, 2H, octyl), 2.13 (m, 2H, octyl), 1.34 (m, 4H, octyl), 1.25 (m, 6H, octyl), 0.85 (t, J=7.3 Hz, 3H, octyl).

Example 42

Example Compound 42 was synthesized according to the following reaction scheme.

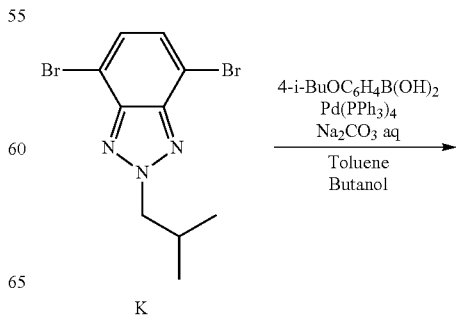

-continued

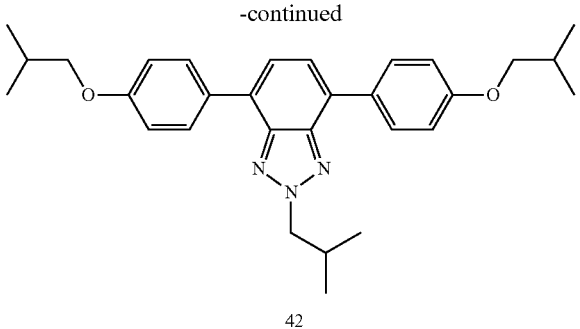

42

A mixture of Intermediate K (1.32 g, 4.0 mmol), 4-isobutoxyphenylboronic acid (1.94 g, 10.0 mmol), tetrakis(triphenylphosphine)palladium(0) (1.00 g, 0.86 mmol), solution of sodium carbonate (2.12 g, 20 mmol) in water (15 mL), butanol (50 mL), and toluene (30 mL) was vigorously stirred and heated under argon at 100° C. for 16 hours. The reaction mixture was poured into water (300 mL), stirred for 30 minutes and extracted with toluene/ethyl acetate/hexane (5:3:2, 500 mL). The volatiles were removed under reduced pressure, and the residue was chromatographed (silica gel, hexane/dichloromethane, 1:1). The separated product was recrystallized from ethanol to give pure 4,7-bis(4-isobutoxyphenyl)-2-isobutyl-2H-benzo[d][1,2,3]triazole, Compound 42 (1.57 g, 83% yield). $^1$H NMR (400 MHz, CDCl$_3$): δ 7.99 (d, J=8.7 Hz, 4H, 4-i-BuOC$_6$H$_4$), 7.55 (s, 2H, benzotriazole), 7.04 (d, J=8.8 Hz, 4H, 4-i-BuOC$_6$H$_4$), 4.58 (d, J=7.3 Hz, 2H, i-Bu), 3.79 (d, J=6.6 Hz, 4H, 4-i-BuOC$_6$H$_4$), 2.59 (m, 1H, i-Bu), 2.13 (m, 2H, 4-i-BuOC$_6$H$_4$), 1.04 (d, J=6.6 Hz, 12H, 4-i-BuOC$_6$H$_4$), 1.00 (d, J=6.6 Hz, 6H, i-Bu). UV-vis spectrum (PVB): λ$_{max}$=359 nm. Fluorimetry (PVB): λ$_{max}$=434 nm.

Example 43

Example Compound 43 was synthesized according to the following reaction scheme.

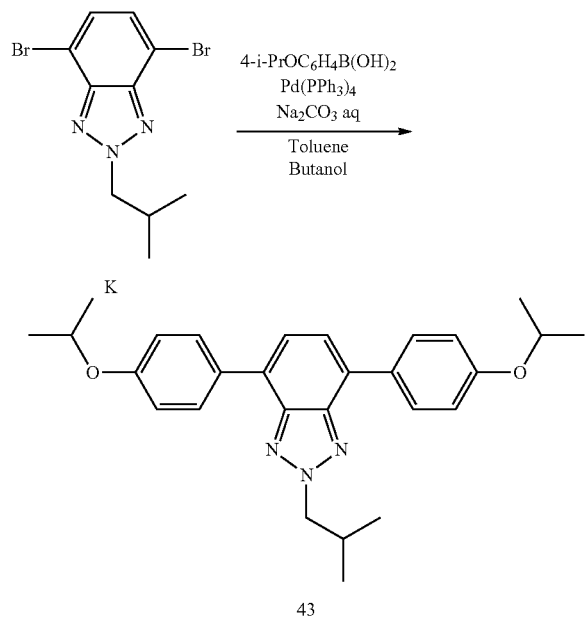

43

A mixture of Intermediate K (666 mg, 2.0 mmol), 4-isopropoxyphenylboronic acid (1.00 g, 5.5 mmol), tetrakis(triphenylphosphine)palladium(0) (0.50 g, 0.43 mmol), solution of sodium carbonate (1.06 g, 10 mmol) in water (8 mL), butanol (30 mL), and toluene (20 mL) was vigorously stirred and heated under argon at 100° C. for 20 hours. The reaction mixture was poured into water (300 mL), stirred for 30 minutes and extracted with toluene/ethyl acetate (1:1, 300 mL). The volatiles were removed under reduced pressure, and the residue was chromatographed (silica gel, hexane/dichloromethane, 1:1). The separated product was recrystallized from ethanol to give pure 4,7-bis(4-isopropoxyphenyl)-2-isobutyl-2H-benzo[d][1,2,3]triazole, Compound 43 (655 mg, 74% yield). 1H NMR (400 MHz, CDCl$_3$): δ 8.00 (d, J=8.7 Hz, 4H, 4-i-PrOC$_6$H$_4$), 7.55 (s, 2H, benzotriazole), 7.02 (d, J=8.8 Hz, 4H, 4-i-PrOC$_6$H$_4$), 4.64 (septet, J=6.2 Hz, 2H, 4-i-PrOC$_6$H$_4$), 4.59 (d, J=7.7 Hz, 2H, i-Bu), 2.61 (m, 1H, i-Bu), 1.38 (d, J=6.2 Hz, 12H, 4-i-PrOC$_6$H$_4$), 1.01 (d, J=6.6 Hz, 6H, i-Bu). UV-vis spectrum (PVB): λ$_{max}$=360 nm. Fluorimetry (PVB): λ$_{max}$=435 nm.

Example 44

Example Compound 44 was synthesized according to the following reaction scheme.

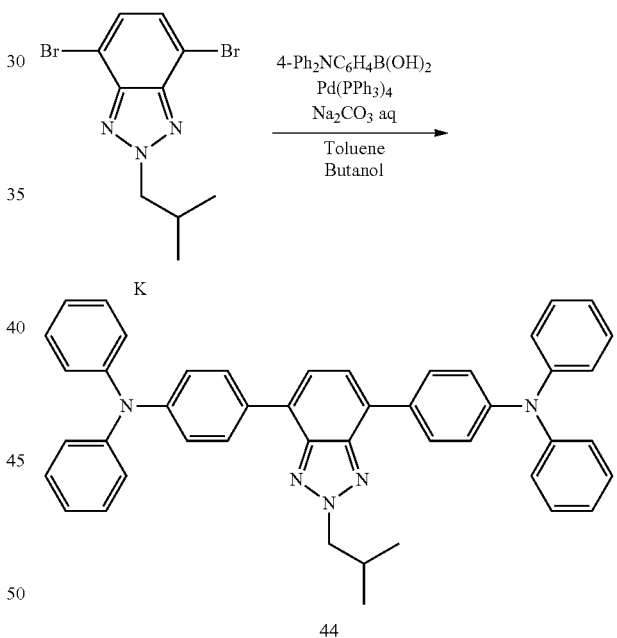

44

A mixture of Intermediate K (1.66 g, 5.0 mmol), 4-(diphenylamino)phenylboronic acid (3.47 g, 12 mmol), tetrakis(triphenylphosphine)palladium(0) (1.00 g, 0.86 mmol), solution of sodium carbonate (2.12 g, 20 mmol) in water (15 mL), butanol (50 mL), and toluene (30 mL) was stirred vigorously and heated under argon at 105° C. for 16 hours. The reaction mixture was poured into water (200 mL), stirred for 30 minutes and extracted with toluene/ethyl acetate (3:1, 400 mL). The volatiles were removed under reduced pressure, and the residue was chromatographed (silica gel, hexane/dichloromethane, 1:1). The separated product was recrystallized from acetone to give pure 4,7-bis(4-N,N-diphenylaminophenyl)-2-isobutyl-2H-benzo[d][1,2,3]triazole, Compound 44 (2.81 g, 85% yield). $^1$H NMR (400 MHz, CDCl$_3$): δ 7.99 (d, J=8.4 Hz, 4H, 4-Ph$_2$NC$_6$H$_4$), 7.59 (s, 2H, benzotriazole), 7.28 (t, J=7.3 Hz, 8H, Ph), 7.18 (m, 12H, 4-Ph$_2$NC$_6$H$_4$ and Ph), 7.04 (t, J=7.4 Hz, 4H, Ph), 4.58 (d, J=7.3 Hz, 2H, i-Bu), 2.58 (m, 1H, i-Bu), 0.98 (d, J=6.9 Hz, 6H, i-Bu). UV-vis spectrum (PVB): $\lambda_{max}$=409 nm. Fluorimetry (PVB): $\lambda_{max}$=473 nm.

Example 45

Example Compound 45 was synthesized according to the following reaction scheme.

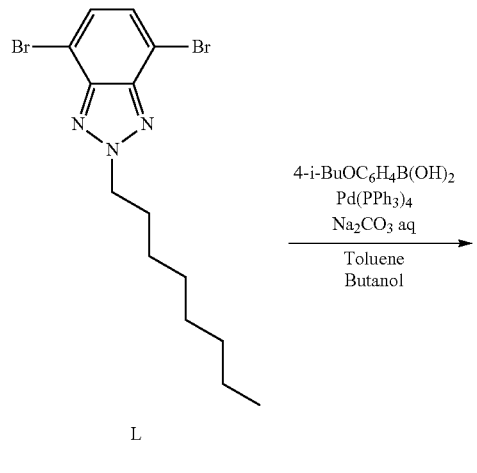

L

45

A mixture of Intermediate L (778 mg, 2.0 mmol), 4-isobutoxyphenylboronic acid (970 mg, 5.0 mmol), tetrakis(triphenylphosphine)palladium(0) (500 mg, 0.43 mmol), solution of sodium carbonate (2.12 g, 20 mmol) in water (15 mL), butanol (50 mL), and toluene (30 mL) was vigorously stirred and heated under argon at 105° C. for 16 hours. The reaction mixture was poured into water (200 mL), stirred for 30 minutes and extracted with toluene/ethyl acetate/hexane (2:1:1, 400 mL). The extract was dried over magnesium sulfate, the volatiles were removed under reduced pressure, and the residue was chromatographed (silica gel, hexane/dichloromethane, 1:1). The separated product was crystallized from acetonitrile to give pure 4,7-bis(4-isobutoxyphenyl)-2-octyl-2H-benzo[d][1,2,3]triazole, Compound 45 (1.57 g, 62% yield). $^1$H NMR (400 MHz, CDCl$_3$): δ 7.99 (d, J=8.8 Hz, 4H, 4-i-BuOC$_6$H$_4$), 7.54 (s, 2H, benzotriazole), 7.04 (d, J=8.8 Hz, 4H, 4-i-BuOC$_6$H$_4$), 4.76 (t, J=7.0 Hz, 2H, octyl), 3.79 (d, J=6.2 Hz, 4H, 4-i-BuOC$_6$H$_4$), 2.13 (m, 4H, octyl), 1.28 (m, 2H, octyl), 1.25 (m, 6H, octyl), 1.04 (d, J=6.6 Hz, 12H, 4-i-BuOC$_6$H$_4$), 0.86 (t, J=6.6 Hz, 3H, octyl). UV-vis spectrum (PVB): $\lambda_{max}$=359 nm. Fluorimetry (PVB): $\lambda_{max}$=431 nm.

Example 46

Example Compound 46 was synthesized according to the following reaction scheme.

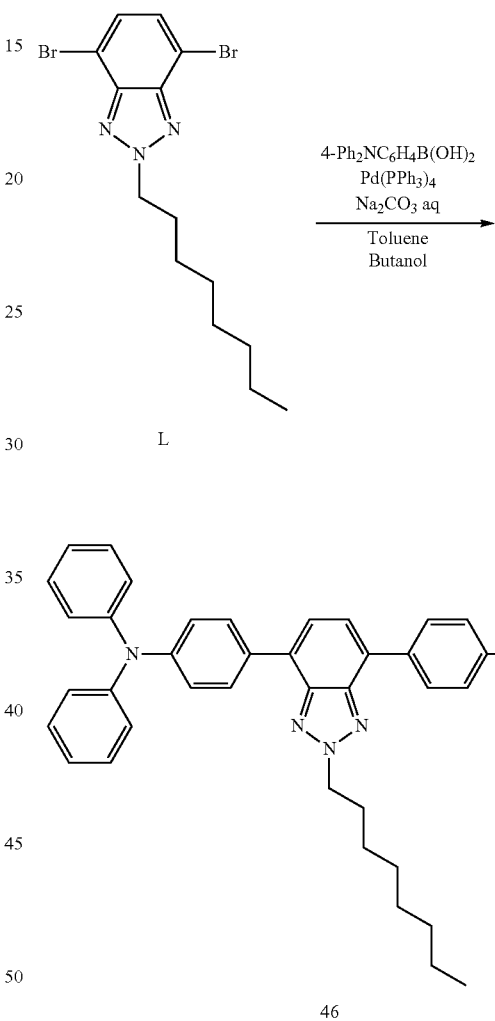

L

46

A reaction procedure, work-up and purification analogous to those in example 3 were applied starting from Intermediate L (1.95 g, 5 mmol) and 4-(diphenylamino)-phenylboronic acid (3.47 g, 12 mmol). The separated product was triturated with acetone to give yellow crystals of pure 4,7-bis(4-N,N-diphenylaminophenyl)-2-octyl-2H-benzo[d][1,2,3]triazole, Compound 46 (2.81 g, 85% yield). 1H NMR (400 MHz, CDCl$_3$): δ 7.98 (d, J=8.7 Hz, 4H, 4-Ph$_2$NC$_6$H$_4$), 7.59 (s, 2H, benzotriazole), 7.28 (t, J=7.3 Hz, 8H, Ph), 7.18 (m, 12H, 4-Ph$_2$NC$_6$H$_4$ and Ph), 7.04 (t, J=7.3 Hz, 4H, Ph), 4.76 (t, J=7.3 Hz, 2H, octyl), 2.14 (m, 4H, octyl), 1.36 (m, 2H, octyl), 1.23 (m, 6H, octyl), 0.83 (t, J=6.6 Hz, 3H, octyl). UV-vis spectrum (PVB): $\lambda_{max}$=408 nm. Fluorimetry (PVB): $\lambda_{max}$=474 nm.

Example 47

Example Compound 47 was synthesized according to the following reaction scheme.

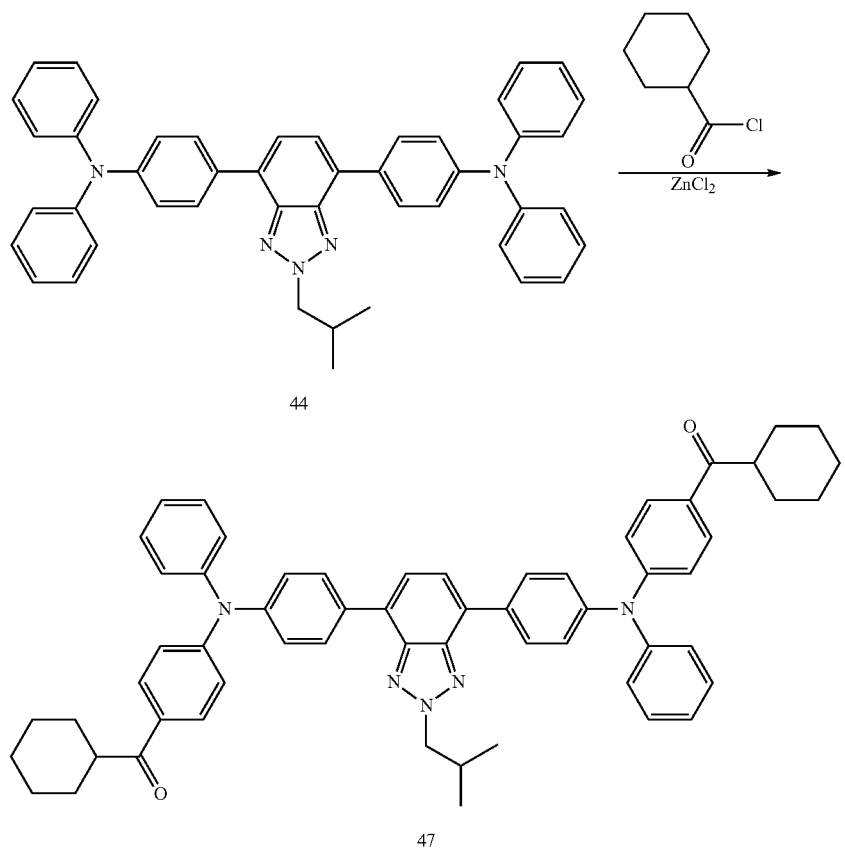

A solution of chromophore Compound 44 (662 mg, 1.0 mmol) and cyclohexanecarbonyl chloride (0.80 mL, 6 mmol) in anhydrous dichloromethane (20 mL) was treated with 1 M zinc chloride in ethyl ether (10 mL, 10 mmol) and stirred under argon at room temperature for 16 hours. Thin layer chromotography indicated no starting material left. The reaction mixture was poured into water (200 mL), treated with 1 M sodium carbonate (50 mL), diluted with dichloromethane (200 mL), and stirred for 30 minutes. The dichloromethane layer was separated and dried over anhydrous magnesium sulfate. The solvent was removed under reduced pressure, and the residue was subjected to column chromatography (silica gel, hexane/dichloromethane/ethyl acetate, 37:60:3). The obtained product was recrystallized from ethanol to give pure Compound 47 (550 mg, 62% yield). $^1$H NMR (400 MHz, CDCl$_3$): δ 8.06 (d, J=8.8 Hz, 4H), 7.83 (d, J=9.2 Hz, 4H), 7.63 (s, 2H, benzotriazole), 7.34 (t, J=7.3 Hz, 4H, Ph), 7.27 (d, J=8.8 Hz, 4H), 7.23 (m, 4H, Ph), 7.16 (t, J=7.4 Hz, 2H, Ph), 7.10 (d, J=8.8 Hz, 4H), 4.59 (d, J=7.3 Hz, 2H, i-Bu), 3.20 (tt, J=11.3 and 3.1 Hz, 2H, cyclohexyl), 2.60 (m, 1H, i-Bu), 1.86 (m, 8H, cyclohexyl), 1.20-1.73 (m, 12H, cyclohexyl), 1.00 (d, J=7.0 Hz, 6H, i-Bu). UV-vis spectrum (PVB): λ$_{max}$=405 nm. Fluorimetry (PVB): λ$_{max}$=468 nm.

Examples 48 and 49

Examples 48 and 49 are synthesized in a two step process.

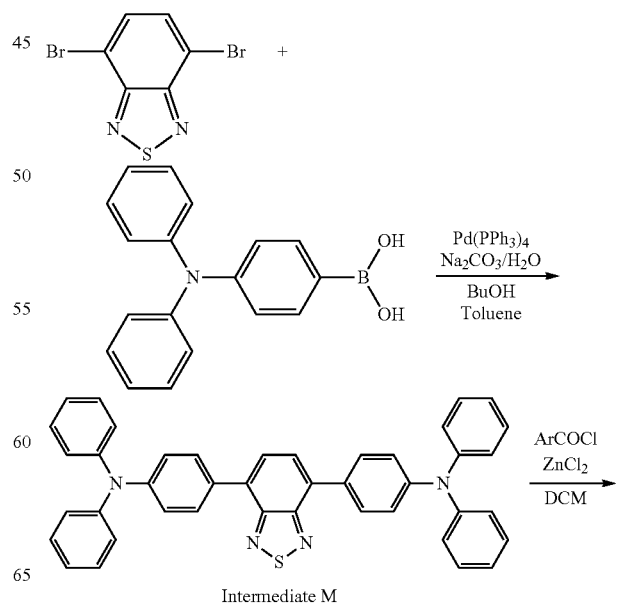

Intermediate M

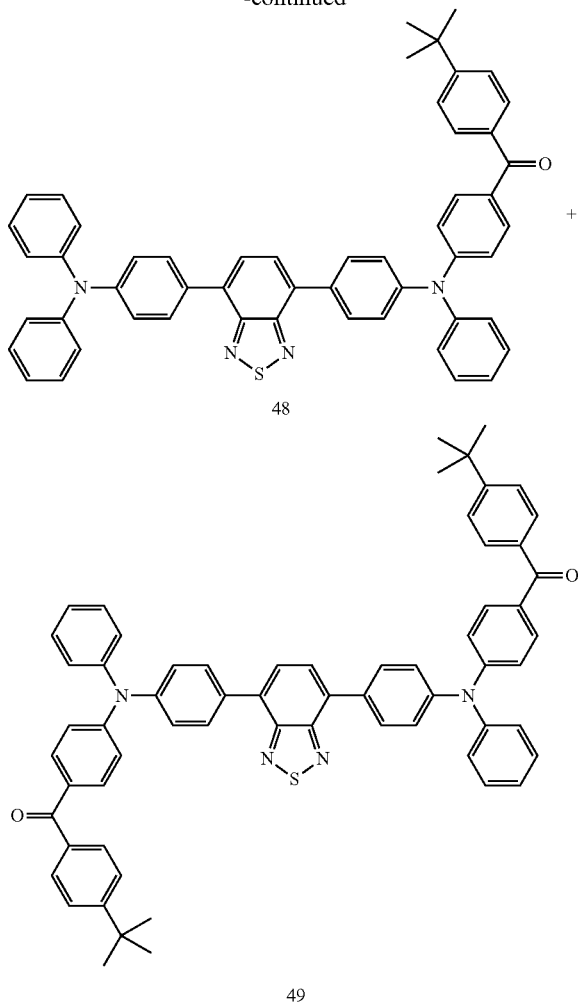

(400 mL) was stirred under argon and heated at 100° C. for 20 hours. After cooling to room temperature, the mixture was diluted with water (600 mL) and stirred for 2 hours. Finally, the reaction mixture was extracted with toluene (2 L), and the volatiles were removed under reduced pressure. The residue was chromatographed using silica gel and hexane/dichloromethane (1:1) as an eluent to give 26.96 g (43.3 mmol, 96%) of 4,7-bis[(N,N-diphenylamino)phenyl)]benzo[2,1,3]thiadiazole (Intermediate M).

Step 2: Synthesis of Examples 48 and 49

To a solution of 4,7-bis[(N,N-diphenylamino)phenyl)]benzo[2,1,3]thiadiazole (22.0 g, 35.3 mmol) in dichloromethane (800 mL) stirred under argon and cooled in an ice/water bath were added in small portions 4-t-butylbenzoyl chloride (97.4 mL, 500 mmol) and 1M solution of zinc chloride in ethyl ether (700 mL, 700 mmol). The obtained mixture was stirred and heated at 44° C. for 68 hours. The reaction mixture was poured onto crushed ice (2 kg), stirred, treated with saturated sodium carbonate to pH 8, diluted with dichloromethane (2 L) and filtered through a frit-glass funnel under atmospheric pressure. The dichloromethane layer was separated, dried over magnesium sulfate, and the solvent was evaporated. Column chromatography of the residue (silica gel, hexane/dichloromethane/ethyl acetate 48:50:2) followed by recrystallization of the first fraction from ethanol gave pure chromophore Example 48, 7.72 g (28% yield). $^1$H NMR (400 MHz, CDCl$_3$): δ 7.95 (d, 2H, J=8.8 Hz), 7.88 (d, 2H, J=8.7 Hz), 7.76 (m, 2H), 7.74 (d, 4H, J=8.4 Hz), 7.48 (d, 2H, J=8.4 Hz), 7.36 (dd, 2H, J=7.3 and 8.0 Hz), 7.29 (m, 8H), 7.20 (m, 7H), 7.14 (d, 2H, J=8.8 Hz), 7.07 (t, 2H, J=1.1 and 7.3 Hz), 1.36 (s, 9H). UV-vis spectrum: $\lambda_{max}$=448 nm (dichloromethane), 456 nm (PVB film). Fluorimetry: $\lambda_{max}$=618 nm (dichloromethane), 582 nm (PVB film).

The second fraction gave chromophore Example 49, 12.35 g (37% yield). $^1$H NMR (400 MHz, CDCl$_3$): δ 7.95 (d, 4H, J=8.4 Hz), 7.79-7.73 (m, 10H), 7.48 (d, 4H, J=7.7 Hz), 7.36 (t, 4H, J=7.7 Hz), 7.31 (d, 4H, J=8.4 Hz), 7.25 (d, 4H, J=7.7 Hz), 7.18 (t, J=7.3, 2H, Ph), 7.14 (d, 4H, J=8.8 Hz), 1.35 (s, 18H). UV-vis spectrum: $\lambda_{max}$=437 nm (dichloromethane), 441 nm (PVB film). Fluorimetry: $\lambda_{max}$=607 nm (dichloromethane), 547 nm (PVB film).

Examples 50 and 51

Examples 50 and 51 are synthesized in a four step process.

Step 1: Synthesis of Intermediate M—4,7-bis[(N,N-diphenylamino)phenyl)]benzo[2,1,3]thiadiazole A mixture of 4,7-dibromobenzo[2,1,3]thiadiazole (13.2 g, 45 mmol), 4-(N,N-diphenylamino)phenylboronic acid (30.0 g, 104 mmol), a solution of sodium carbonate (21.2 g, 200 mmol) in water (80 mL), tetrakis(triphenylphosphine)palladium(0) (5.0 g, 4.3 mmol), n-butanol (800 mL), and toluene

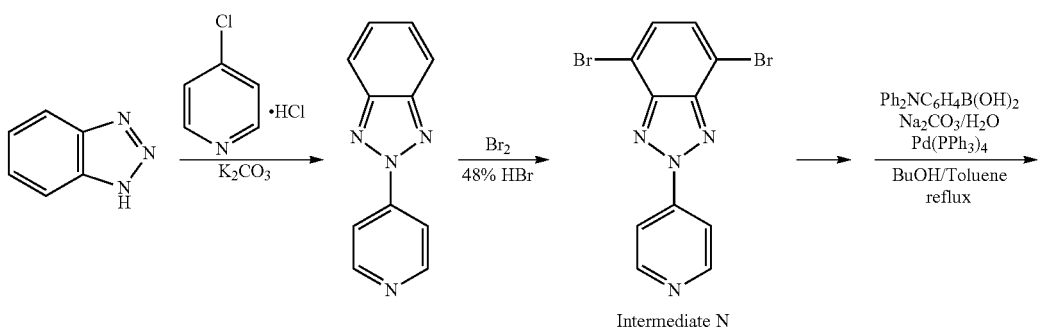

-continued

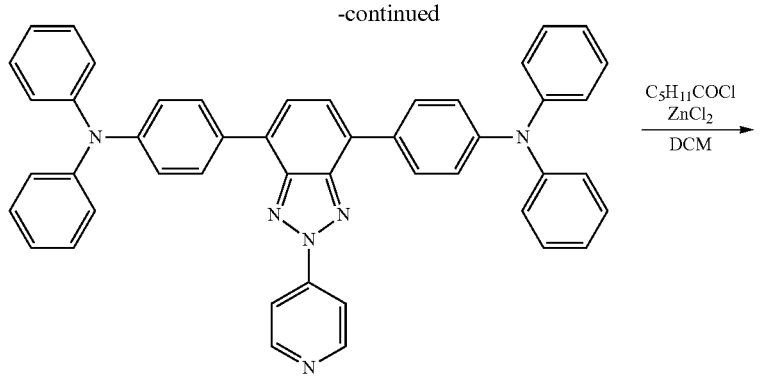

Intermediate O

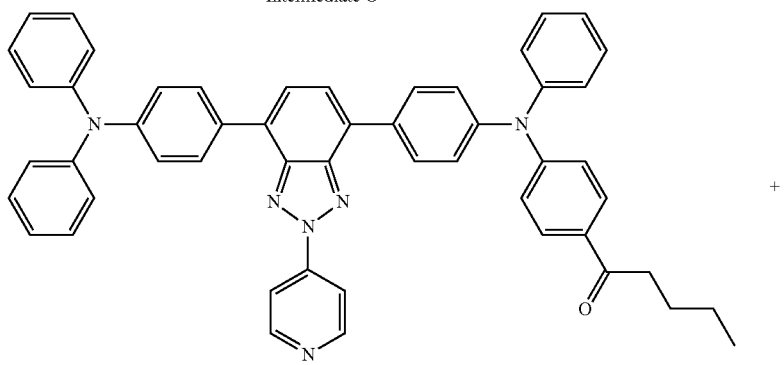

51

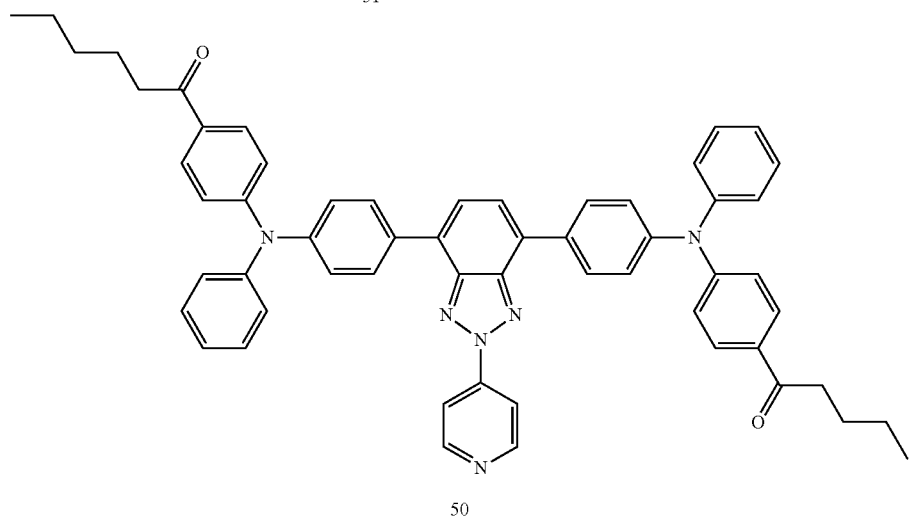

50

Step 1: Synthesis of 2-(pyridin-4-yl)-2H-benzo[d][1,2,3]triazole

A mixture of 4-chloropyridinium hydrochloride (25.0 g, 166 mmol), benzotriazole (29.6 g, 249 mmol), potassium carbonate (69.1 g, 500 mmol), and dimethylformamide (DMF) (500 mL) was stirred and heated under argon at 130° C. for 3 days. After cooling, the solid was filtered off, and the solvent was evaporated under reduced pressure. The residue was treated with dichloromethane (200 mL), filtered and chromatographed using a column filled with silica gel (500 mL) and hexane/ethyl acetate (1:1) as an eluent. Fractions containing the desired product were combined, and the solvent was distilled off. The residue was triturated with ethanol, the solid was filtered off and dried in a vacuum oven to give 2-(pyridin-4-yl)-2H-benzo[d][1,2,3]triazole, 6.45 g, 20%). $^1$H NMR (400 MHz, CDCl$_3$): δ 8.80 (m, 2H, pyridine), 8.26 (m, 2H, pyridine), 7.93 (m, 2H, benzotriazole), 7.46 (m, 2H, benzotriazole).

Step 2: Synthesis of Intermediate N—4,7-dibromo-2-(pyridin-4-yl)-2H-benzo[d][1,2,3]triazole A mixture of 2-(pyridin-4-yl)-2H-benzo[d][1,2,3]triazole (6.42 g, 32.7 mmol), bromine (5.20 mL, 100 mmol) and 48% HBr (50 mL) was heated at 120° C. for 40 hours. The reaction mixture was poured into ice/water (500 mL), treated with 5N NaOH to pH 8, and the excess of bromine was removed by addition of 1 M sodium thiosulfate (test with KI/starch paper). After stirring for 30 minutes, the solid was filtered off, washed with water and dried in a vacuum oven. The crude product was purified by column chromatography (silica gel, dichloromethane/ethyl acetate 9:1) and washing with ethyl acetate (50 mL) to give 4,7-dibromo-2-(pyridin-4-yl)-2H-benzo[d][1,2,3]triazole (Intermediate B), 5.00 g (43%). $^1$H NMR (400 MHz, CDCl$_3$): δ 8.85 (m, 2H, pyridine), 8.33 (m, 2H, pyridine), 7.53 (s, 2H, benzotriazole).

Step 3: Synthesis of Intermediate O-4,7-bis(4-(N,N-diphenylamino)phenyl)-2-(pyridin-4-yl)-2H-benzo[d][1,2,3]triazole A mixture of Intermediate N (purity 90%, 1.95 g, 5 mmol), sodium carbonate (2.69 g, 25 mmol), 4-(diphenylamino)phenylboronic acid (3.47 g, 12 mmol), tetrakis(triphenylphosphine)palladium (0) (0.58 g, 0.5 mmol), water (20 mL), dioxane (80 mL), and toluene (10 mL) was heated under argon at 110° C. for 48 hours. The reaction mixture was poured into water (200 mL), diluted with dichloromethane (200 mL), treated with 2N NaOH (50 mL), stirred for 1 hour, and the dichloromethane layer was separated. The aqueous phase was washed with dichloromethane (200 mL). Both dichloromethane solutions were combined, dried over anhydrous sodium sulfate, and the solvent was removed under reduced pressure. The crude product was purified by column chromatography and recrystallization from ethyl acetate/ethanol (1:1) to give 4,7-bis(4-(N,N-diphenylamino)phenyl)-2-(pyridin-4-yl)-2H-benzo[d][1,2,3]triazole (Intermediate C), orange crystals, 1.71 g (50%). $^1$H NMR (400 MHz, CDCl$_3$): δ 8.80 (m, 2H, pyridine), 8.34 (m, 2H, pyridine), 8.06 (d, J=8.7 Hz, 4H, p-phenylene), 7.67 (s, 2H, benzotriazole), 7.31 (m, 8H, Ph), 7.21 (m, 12H, p-phenylene and Ph), 7.08 (tt, J=7.3 and 2.2 Hz, 4H, Ph). UV-vis spectrum (dichloromethane): λ$_{max}$=451 nm. Fluorimetry (dichloromethane): λ$_{max}$=593 nm. UV-vis spectrum: λ$_{max}$=437 nm (dichloromethane), 455 nm (PVB film). Fluorimetry: λ$_{max}$=607 nm (dichloromethane), 547 nm (PVB film).

Step 4: Synthesis of Examples 50 and 51

To a solution of Intermediate O (580 mg, 0.85 mmol) in anhydrous dichloromethane (40 mL) stirred under argon was added 1 M zinc chloride in ethyl ether (10 mL) followed by hexanoyl chloride (0.56 mL, 4.0 mmol). The obtained mixture was stirred and heated at 40° C. for 16 hours. The reaction mixture was poured into water (100 mL), diluted with dichloromethane (100 mL), treated with 5 N sodium hydroxide to pH 12, and stirred for 1 hour. The organic layer was separated, and the aqueous layer was washed with dichloromethane (50 mL). Combined dichloromethane solutions were washed with saturated sodium bicarbonate (100 mL), dried over anhydrous sodium carbonate, and the solvent was evaporated. The residue was chromatographed (silica gel, dichloromethane/ethyl acetate 9:1). Recrystallization of the first fraction from ethanol gave chromophore Example 50 (445 mg, 59% yield). 1H NMR (400 MHz, CDCl$_3$): δ 8.80 (m, 2H), 8.34 (m, 2H), 8.11 (d, 4H, J=8.8 Hz), 7.85 (d, 4H, J=8.8 Hz), 7.71 (s, 2H), 7.37 (t, 4H, J=7.7 Hz), 7.30 (d, 4H, J=8.4 Hz), 7.23 (m, 4H), 7.19 (t, 2H, J=7.7 Hz), 7.12 (d, 4H, J=8.8 Hz), 2.89 (t, 4H, J=7.5 Hz), 1.73 (m, 4H), 1.35 (m, 8H), 0.90 (t, 6H, J=7.0 Hz). UV-vis spectrum: λ$_{max}$=432 nm (dichloromethane), 442 nm (PVB film). Fluorimetry: λ$_{max}$=572 nm (dichloromethane), 535 nm (PVB film).

The second fraction gave chromophore Example 51 (320 mg, 41%). $^1$H NMR (400 MHz, CDCl$_3$): δ 8.79 (m, 2H), 8.33 (m, 2H), 8.10 (d, 2H, J=8.8 Hz), 8.07 (m, 2H), 7.85 (d, 2H, J=8.8 Hz), 7.69 (s, 2H), 7.35 (m, 3H), 7.29 (m, 3H, J=8.4 Hz), 7.23 (m, 8H), 7.18 (m, 2H), 7.11 (m, 5H), 2.89 (t, 2H, J=7.4 Hz), 1.72 (m, 2H), 1.36 (m, 4H), 0.90 (t, 3H, J=7.0 Hz). UV-vis spectrum: λ$_{max}$=445 nm (dichloromethane), 448 nm (PVB film). Fluorimetry: λ$_{max}$=594 nm (dichloromethane), 550 nm (PVB film).

Example 52

Example 52 is synthesized in a four step process.

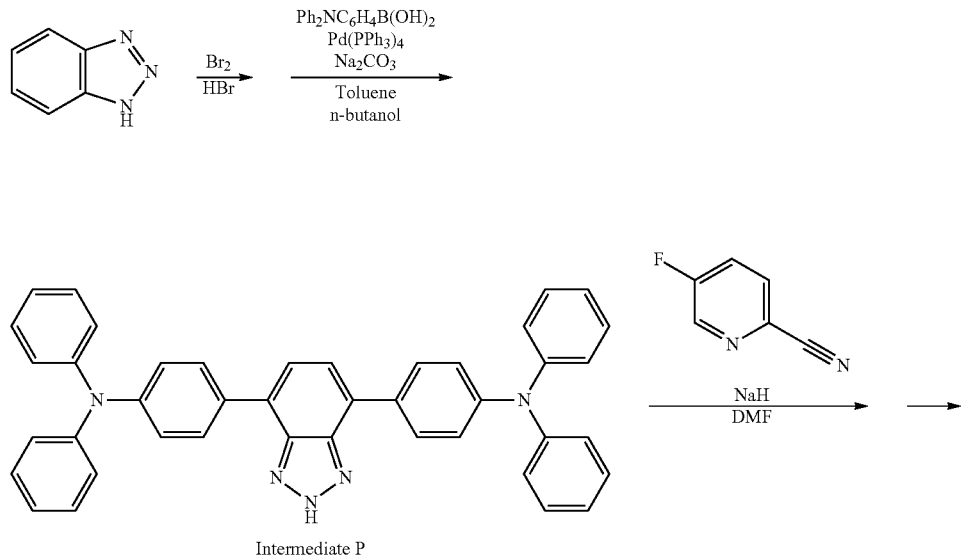

Intermediate P

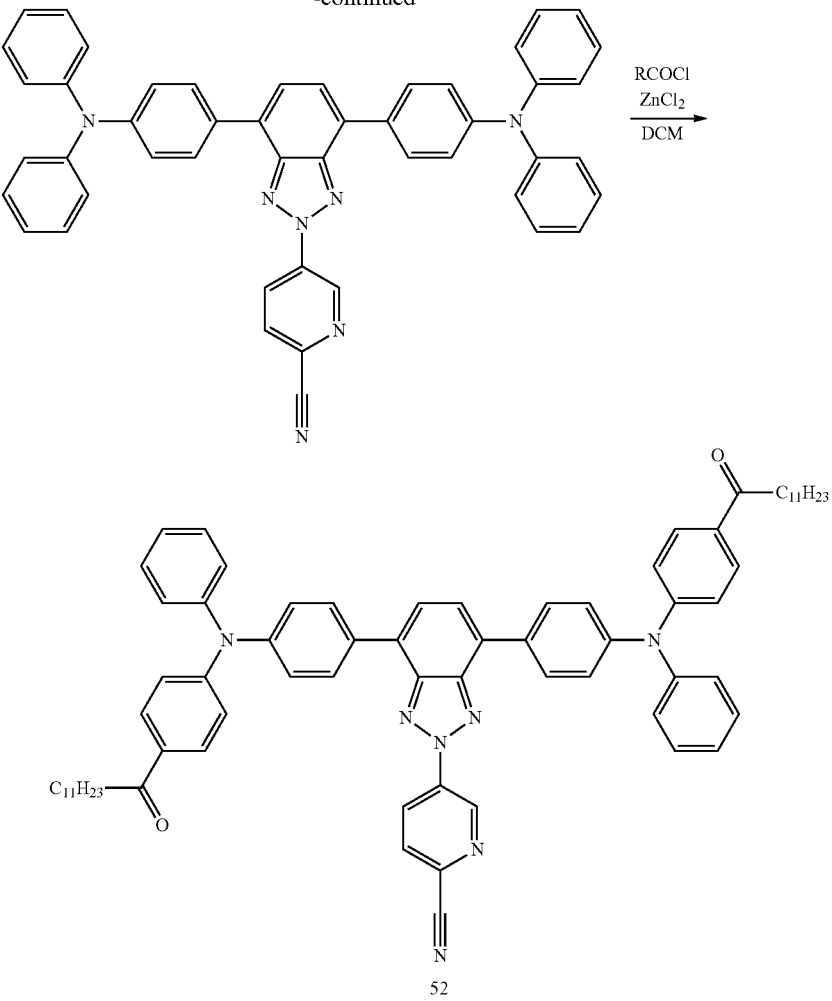

Step 1: Synthesis of 4,7-dibromo-2H-benzo[d][1,2,3]triazole

A mixture of benzotriazole (5.96 g, 50 mmol), bromine (7.7 mL, 150 mmol) and 48% HBr (30 mL) was heated at 120° C. for 24 hours. The reaction mixture was poured into ice/water (200 mL), neutralized with 5N NaOH, and the excess of bromine was removed by addition of 1M sodium thiosulfate (test with KI/starch paper). After stirring for 30 minutes, the solid was filtered off, washed with water and dried in a vacuum oven. The crude product was purified by column chromatography (silica gel, dichloromethane/ethyl acetate 75:25) and washing with ethyl acetate (50 mL) to give 4,7-dibromo-2H-benzo[d][1,2,3]triazole, 2.65 g (19%).

Step 2: Synthesis of Intermediate P-4,7-bis(4-(N,N-diphenylamino)phenyl)-2H-benzo[d][1,2,3]triazole A mixture of 4,7-dibromo-2H-benzo[d][1,2,3]triazole (1.37 g, 5.5 mmol), 4-(diphenylamino)phenylboronic acid (3.47 g, 12 mmol), sodium carbonate (5.30 g, 50 mmol) in water (10 mL), tetrakis(triphenylphosphine)palladium (0) (1.15 g, 1.0 mmol), n-butanol (80 mL), and toluene (10 mL) was stirred and heated under argon at 120° C. for 4 days. The reaction mixture was poured into water (300 mL), stirred for 15 minutes, and extracted with dichloromethane (2×300 mL). The solution was dried over anhydrous sodium sulfate, the solvent was removed under reduced pressure, and the residue was chromatographed (silica gel, dichloromethane/ethyl acetate 95:5) to give 4,7-bis(4-(N,N-diphenylamino)phenyl)-2H-benzo[d][1,2,3]triazole (Intermediate P), 1.85 g (56%).

Step 3: Synthesis of 4,7-bis(4-(N,N-diphenylamino)phenyl)-2-(6-cyanopyridin-3-yl)-2H-benzo[d][1,2,3]triazole Sodium hydride (60%, 120 mg, 3 mmol) was added to a solution of Intermediate P (1.21 g, 2.0 mmol) and 5-fluoro-2-pyridinecarbonitrile (0.61 g, 5.0 mmol) in anhydrous dimethylformamide (20 mL), stirred under argon, and the obtained mixture was heated at 80° C. for 16 hours. The reaction mixture was poured into ice/water (200 mL), and extracted with dichloromethane (200 mL). The extract was dried over sodium sulfate, and the solvent was evaporated. The residue was diluted with chlorobenzene (50 mL), and the volatiles were removed under high vacuum. The crude product was purified by chromatography (dichloromethane/hexane 2:1) to give 4,7-bis(4-(N,N-diphenylamino)phenyl)-2-(6-cyanopyridin-3-yl)-2H-benzo[d][1,2,3]triazole, dark-red crystals, 1.20 g (85%).

Step 4: Synthesis of Example 52

A solution of 4,7-bis(4-(N,N-diphenylamino)phenyl)-2-(6-cyanopyridin-3-yl)-2H-benzo[d][1,2,3]triazole (708 mg, 1.0 mmol), lauroyl chloride (2.3 mL, 10 mmol) and 1M zinc chloride in ethyl ether (15 mL) in dichloromethane (30 mL) was stirred and heated at 40° C. for 48 hours. The reaction mixture was poured into ice/water (200 mL), diluted with dichloromethane (200 mL), stirred and treated with 1M sodium carbonate to pH 8. The organic layer was separated, washed with brine (100 mL), and the solvent and volatiles were evaporated under reduced pressure. The residue was chromatographed (silica gel, dichloromethane/hexane/ethyl acetate 48:50:2) to give crude chromophore Example 52, red oil, as the first fraction. Slow addition of a solution of this oil in acetone into ethanol resulted in crystalline Example 52, 284 mg (26%). $^1$H NMR (400 MHz, CDCl$_3$): δ 9.81 (d, 1H, J=2.6 Hz), 8.85 (dd, 1H, J=2.7 and 8.8 Hz), 8.08 (d, 4H, J=8.8 Hz), 7.89 (d, 1H, J=8.4 Hz), 7.86 (d, 4H, J=8.8 Hz), 7.73 (s, 2H), 7.37 (t, 4H, J=7.9 Hz) 7.16-7.23 (m, 16H, p-phenylene and Ph), 7.07 (t, J=7.3, 4H, Ph), 7.02 (bs, 1H, N—H). $^1$H NMR (400 MHz, CDCl$_3$): δ 9.81 (d, 1H, J=2.6 Hz), 8.85 (dd, 1H, J=2.7 and 8.8 Hz), 8.08 (d, 4H, J=8.8 Hz), 7.89 (d, 1H, J=8.4 Hz), 7.86 (d, 4H, J=8.8 Hz), 7.73 (s, 2H), 7.37 (t, 4H, J=7.9 Hz), 7.30 (d, 4H, J=8.8 Hz), 7.24 (m, 4H), 7.20 (t, 2H, J=7.3 Hz), 7.13 (d, 4H, J=8.8 Hz), 2.90 (t, 4H, J=7.5 Hz), 1.72 (m, 4H), 1.26 (m, 32H), 0.87 (t, 6H, J=7.0 Hz). UV-vis spectrum: $\lambda_{max}$=447 nm (dichloromethane), 458 nm (PVB film). Fluorimetry: $\lambda_{max}$=610 nm (dichloromethane), 559 nm (PVB film).

Example 53

Example 53 is synthesized in a three step process.

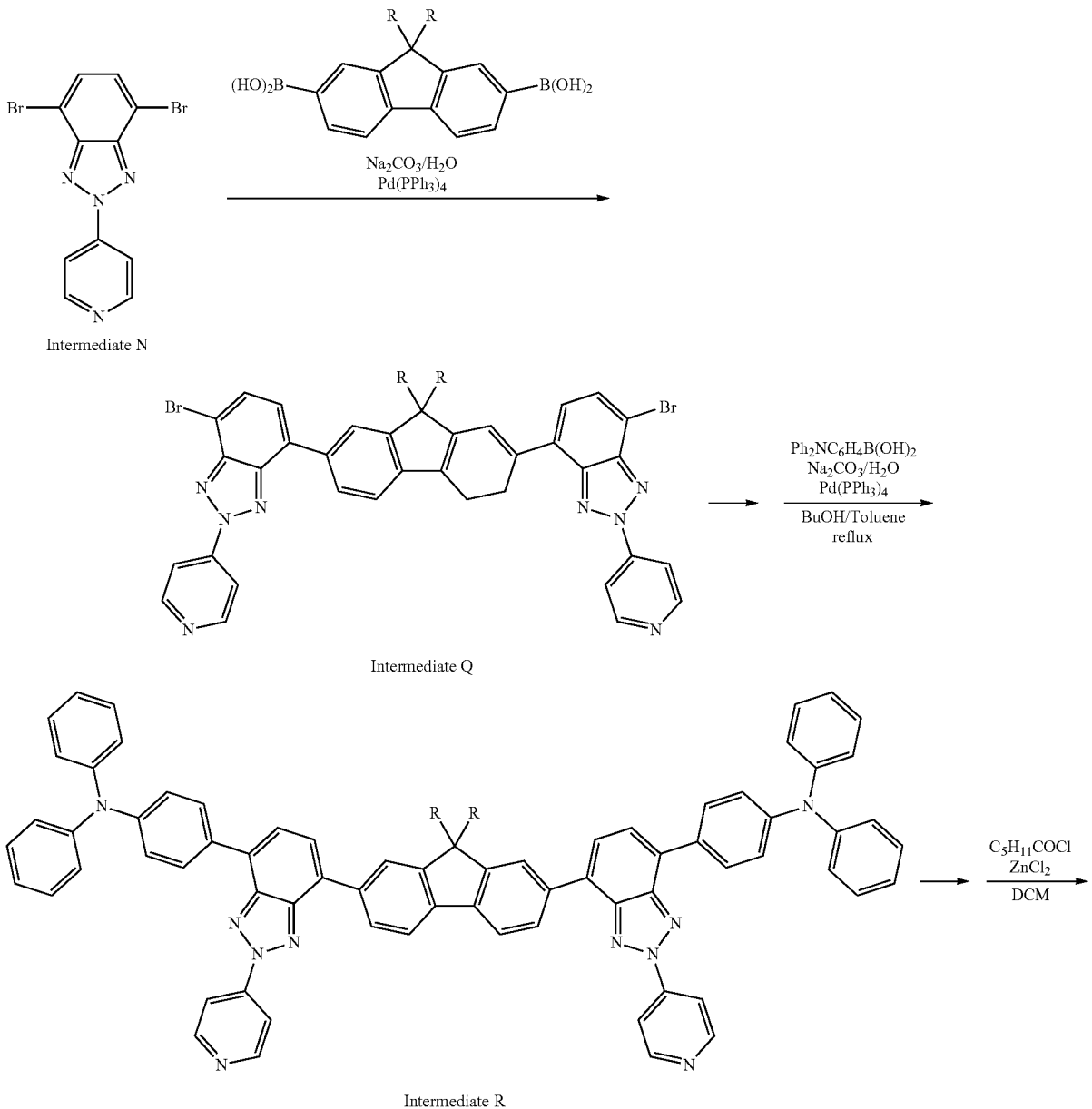

Intermediate N

Intermediate Q

Intermediate R

-continued

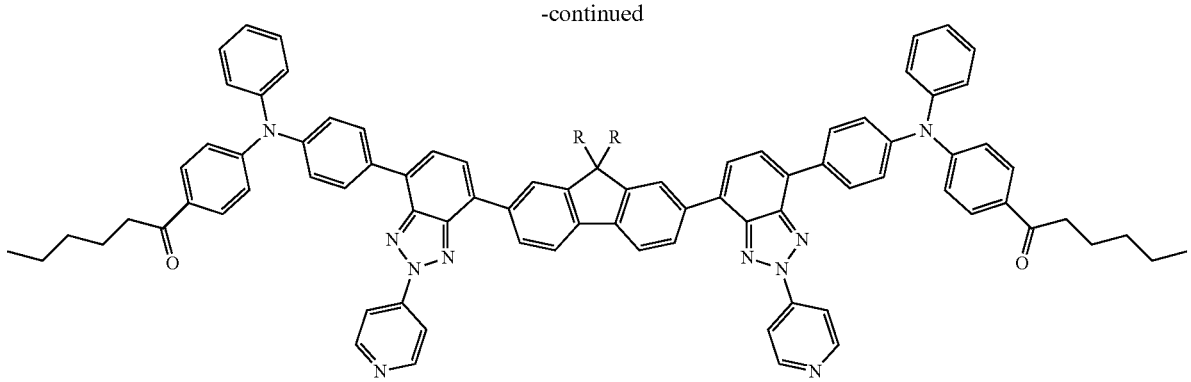

53

R = n-hexyl

Step 1: Synthesis of Intermediate Q—2,7-bis(7-bromo-2-(pyridin-4-yl)-2H-benzo[d][1,2,3]triazol-4-yl)-9,9-dihexylfluorene A mixture of Intermediate N (90%, 13.77 g, 35 mmol), 9,9-dihexylfluorene-2,7-diboronic acid (5.06 g, 12 mmol), sodium carbonate (4.24 g, 40 mmol) in water (25 mL), tetrakis(triphenylphosphine)palladium (0) (2.00 g, 1.72 mmol), n-butanol (60 mL), and toluene (80 mL) was stirred and heated under argon at 110° C. for 48 hours. The reaction mixture was poured into water (300 mL), treated with 5N NaOH (30 mL), stirred for 1 hour, and extracted with dichloromethane (4×400 mL). The volatiles were removed under reduced pressure, and the residue was chromatographed (silica gel, dichloromethane/tetrahydrofuran 9:1). The first fraction gave recovered starting material Intermediate N (5.00 g, 36%).

The material from the second fraction was washed with acetone (20 mL) and dried in a vacuum oven to give 2,7-bis(7-bromo-2-(pyridin-4-yl)-2H-benzo[d][1,2,3]triazol-4-yl)-9,9-dihexylfluorene (Intermediate Q), yellow crystals, 4.52 g (purity 90%, yield 39%). $^1$H NMR (400 MHz, CDCl$_3$): 8.84 (m, 4H, pyridine), 8.36 (m, 4H, pyridine), 8.10 (s, 2H, fluorene), 8.06 (d, 2H, benzotriazole), 7.93 (d, J=8.0 Hz, 2H, benzotriazole), 7.77 (d, J=7.7 Hz, 2H, fluorene), 7.59 (d, J=7.7 Hz, 2H, fluorene), 2.15 (m, 4H, hexyl), 1.13-1.15 (m, 12H, hexyl), 0.89 (m, 4H, hexyl), 0.72 (t, J=6.6 Hz, 6H, hexyl).

Step 2: Synthesis of Intermediate R—2,7-bis(7-(4-(diphenylamino)phenyl)-2-(pyridin-4-yl)-2H-benzo[d][1,2,3]triazol-4-yl)-9,9-dihexyl-9H-fluorene A mixture of Intermediate Q (90%, 400 mg, 0.41 mmol), sodium carbonate (1.06 g, 10 mmol) in water (5 mL), 4-(diphenylamino)phenylboronic acid (1.00 g, 2.26 mmol), tetrakis(triphenylphosphine)palladium (0) (0.50 g, 0.43 mmol), n-butanol (20 mL), and toluene (10 mL) was heated under argon at 100° C. for 4 hours. The reaction mixture was poured into water (200 mL), diluted with dichloromethane (100 mL), stirred for 1 hour, and the dichloromethane layer was separated. The aqueous phase was washed with dichloromethane (100 mL). Both dichloromethane solutions were combined, dried over anhydrous sodium sulfate, and the solvent was removed under reduced pressure. The crude product was purified by column chromatography (silica gel, dichloromethane/ethyl acetate 1:1) and recrystallization from ethanol to give 2,7-bis(7-(4-(diphenylamino)phenyl)-2-(pyridin-4-yl)-2H-benzo[d][1,2,3]triazol-4-yl)-9,9-dihexyl-9H-fluorene (Intermediate R), orange crystals, 350 mg (71%). 1H NMR (400 MHz, CDCl$_3$): δ 8.82 (m, 4H, pyridine), 8.37 (m, 4H, pyridine), 8.21 (d, J=1.1 Hz, 2H, fluorene), 8.14 (dd, J=8.1 and 1.5 Hz, 2H, fluorene), 8.09 (d, J=8.8 Hz, 4H, p-phenylene), 7.94 (d, J=8.0 Hz, 2H, fluorene), 7.81 (d, J=7.3 Hz, 2H, benzotriazole), 7.74 (d, J=7.3 Hz, 2H, benzotriazole), 7.30-7.34 (m, 8H, Ph), 7.25 (d, J=8.8 Hz, 4H, p-phenylene), 7.21 (m, 8H, Ph), 7.09 (tt, J=7.3 and 1.1 Hz, 4H, Ph), 2.19 (m, 4H, hexyl), 1.12 (m, 12H, hexyl), 0.95 (m, 4H, hexyl), 0.73 (t, J=6.6 Hz, 6H, hexyl). UV-vis spectrum (dichloromethane): $\lambda_{max}$=449 nm. Fluorimetry (dichloromethane): $\lambda_{max}$=585 nm.

Step 3: Synthesis of Example 53

A solution of Intermediate R (1.07 G, 0.88 mmol), hexanoyl chloride (2.2 mL, 16 mmol) and 1 M zinc chloride in ethyl ether (30 mL, 30 mmol) in dichloromethane (40 mL) was stirred under argon and heated at 40° C. for 6 hours. The reaction mixture was poured into water (200 mL), diluted with dichloromethane (200 mL), treated with 5 N sodium hydroxide (20 mL), and stirred for 30 minutes. The organic phase was separated, and the aqueous phase was washed with dichloromethane (100 mL). Combined dichloromethane solutions were washed with 2% sodium bicarbonate (100 mL), dried over sodium sulfate, and the solvent was removed under reduced pressure. The crude product was purified by column chromatography (silica gel, dichloromethane/ethyl acetate, 2:1) and recrystallization from ethyl acetate to give chromophore Example 53 (770 mg, 62%). $^1$H NMR (400 MHz, CDCl$_3$): 6808.83 (m, 4H), 8.37 (m, 4H), 8.21 (s, 2H), 8.15 (m, 2H), 8.14 (d, 4H, J=8.4 Hz), 7.95 (d, 2H, J=8.1 Hz), 7.86 (d, 4H, J=8.4 Hz), 7.83 (d, 2H, J=7.7 Hz), 7.77 (d, 2H, J=7.7 Hz), 7.38 (t, 4H, J=7.9 Hz), 7.32 (d, 4H, J=8.5 Hz), 7.25 (d, 4H, J=8.1 Hz), 7.20 (t, 2H, J=7.3 Hz), 7.14 (d, 4H, J=8.5 Hz), 2.90 (t, 4H, J=7.5 Hz), 2.19 (m, 4H), 1.74 (m, 4H), 1.36 (m, 8H), 1.19 (m, 4H), 1.13 (m, 8H), 1.07 (m, 10H), 0.73 (t, 6H, J=7.0 Hz). UV-vis spectrum: $\lambda_{max}$=442 nm (dichloromethane), 459 nm (PVB film). Fluorimetry: $\lambda_{max}$=585 nm (dichloromethane), 530 nm (PVB film).

Examples 54 and 55

Examples 54 and 55 were synthesized in a three step process.

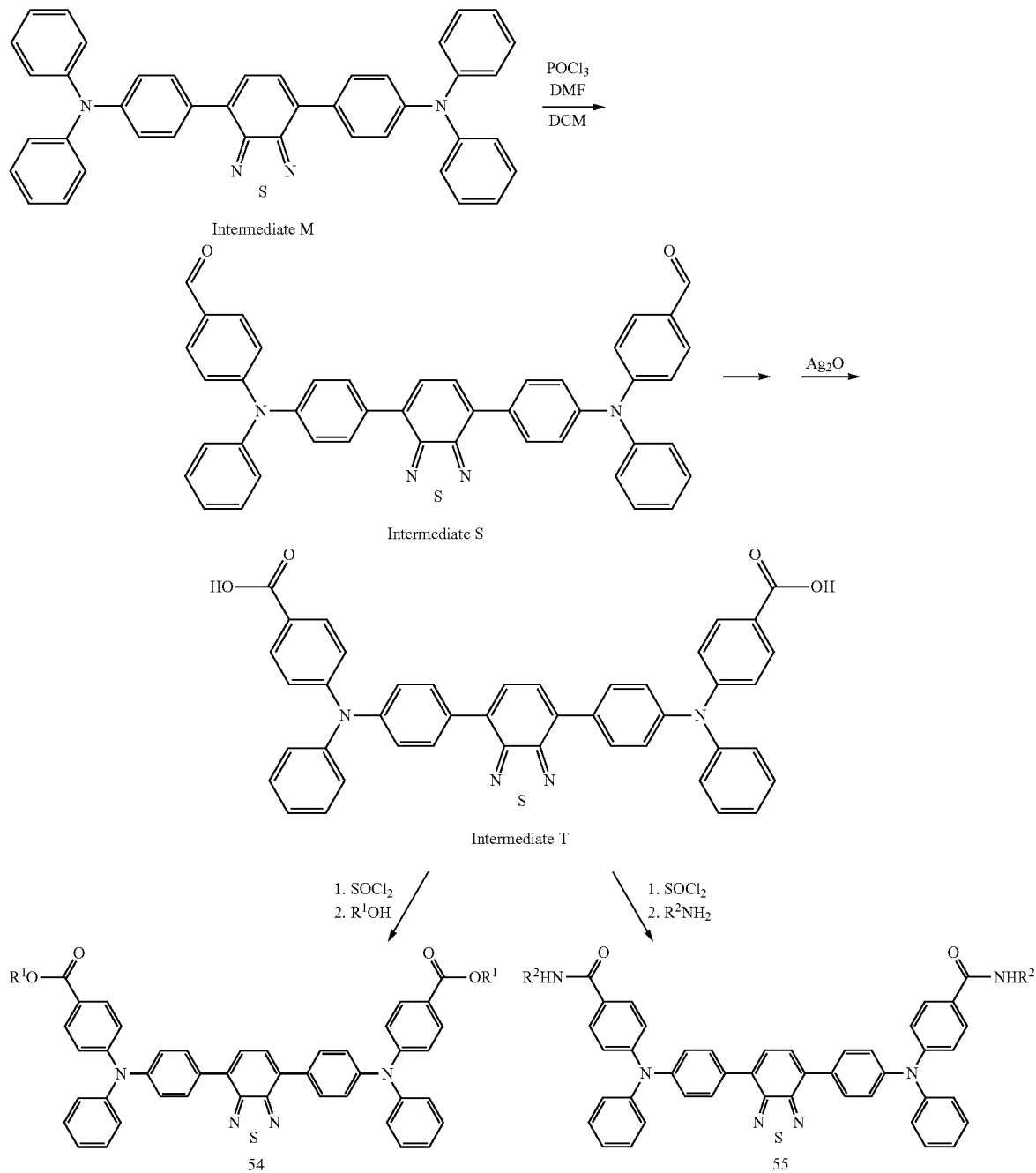

$R^1$ = 2-ethylhexyl
$R^2$ = hexyl

Step 1: Synthesis of Intermediate S

A mixture of Intermediate M (2.48 g, 4 mmol), POCl$_3$ (3.60 mL, 40 mmol), dimethylformamide (4.62 mL, 60 mmol), and dichloromethane (100 mL) was heated under argon at 40° C. for 20 hours. The reaction mixture was poured into ice/water (200 mL), treated with saturated sodium bicarbonate to pH 8, and stirred for 1 hour. The obtained mixture was extracted with dichloromethane (2×200 mL). The extract was dried over sodium sulfate, the solvent was evaporated, and the remaining volatiles were removed under high vacuum. The crude product was purified by column chromatography (silica gel, dichloromethane/hexane/ethyl acetate 60:37:3) to give pure dialdehyde (Intermediate S), orange crystals, 2.35 g (yield 86%).

Step 2: Synthesis of Intermediate T

Intermediate S (2.35 G, 3.5 mmol) was added to a suspension of Ag$_2$O (8.06 G, 35 mmol) and NaOH (5.60 G, 140 mmol) in ethanol (200 mL), and the obtained mixture was stirred vigorously and heated at 40° C. for 16 hours. The reaction mixture was poured into ice/water (800 mL), acidified with concentrated hydrochloric acid to pH 2, stirred for 30 minutes, and extracted with ethyl acetate/toluene (2:1, 2×400 mL). The extract was dried over sodium sulfate, and the solvent was removed under reduced pressure to give diacid, Intermediate T (2.06 G, 83% yield).

Step 3a: Synthesis of Example 54

Thionyl chloride (0.29 mL, 4 mmol) was added to a suspension of Intermediate H (0.71 G, 1.0 mmol) and benzotriazole (0.24 G, 2 mmol) in toluene/dichloromethane (1:1, 20 mL), and the obtained mixture was heated under argon at 40° C. for 1 hour. 2-Ethylhexanol was then added, and the mixture was stirred at room temperature for 3 days. The reaction mixture was poured into water (100 mL), neutralized with saturated sodium bicarbonate, stirred for 30 minutes and extracted with dichloromethane (2×100 mL). The extract was dried over magnesium sulfate, the volatiles were removed under reduced pressure and the residue was chromatographed (silica gel, hexane/dichloromethane 1:2). The fractions containing a fluorescent material were combined, the solvent was evaporated and the residue was dried in a vacuum oven to provide chromophore Example 54 (661, mg, 71% yield) as an orange glassy foam. $^1$H NMR (400 MHz, CDCl$_3$): δ 7.93 (d, 4H, J=8.8 Hz), 7.90 (d, 4H, J=8.8 Hz), 7.78 (s, 2H), 7.35 (dd, 4H, J=7.3 and 8.4 Hz), 7.28 (d, 4H, J=8.5 Hz), 7.22 (dd, 4H, J=1.5 and 8.8 Hz), 7.16 (tt, 2H, J=7.4 and 1.1 Hz), 7.12 (d, 4H, J=8.5 Hz), 4.20 (m, 4H), 1.69 (m, 2H), 1.44-1.30 (m, 16H), 0.94 (t, 6H, J=7.3 Hz), 0.89 (t, 6H, J=7.3 Hz). UV-vis spectrum: $\lambda_{max}$=442 nm (dichloromethane), 446 nm (PVB film). Fluorimetry: $\lambda_{max}$=606 nm (dichloromethane), 558 nm (PVB film).

Step 3b: Synthesis of Example 55

A solution of Intermediate T (0.50 G, 0.70 mmol) and pyridine (1.0 mL) in chloroform (30 mL) was treated with thionyl chloride (0.50 mL, 6.9 mmol) and stirred under argon at room temperature for 1 hour. Hexylamine (2.0 mL, 15 mmol) was added, and the obtained mixture was stirred for 16 hours. The reaction mixture was poured into water (100 mL), diluted with dichloromethane (100 mL), treated with 1M sodium carbonate to pH 10, and stirred for 1 hour. The dichloromethane phase was separated and the aqueous phase was washed with dichloromethane. Both dichloromethane solutions were combined, washed with water (100 mL) and dried over magnesium sulfate. The solvent was removed under reduced pressure, and the residue was chromatographed (silica gel, dichloromethane/ethyl acetate 9:1). The crude product was recrystallized from ethanol to give chromophore Example 55, red crystals, (0.60 G, 98% yield). $^1$H NMR (400 MHz, CDCl$_3$): δ 7.91 (d, 4H, J=8.8 Hz), 7.77 (s, 2H), 7.64 (d, 4H, J=8.8 Hz), 7.33 (dd, 4H, J=7.4 and 8.5 Hz), 7.25 (d, 4H, J=8.8 Hz), 7.20 (dd, 4H, J=1.1 and 8.4 Hz), 7.15 (d, 4H, J=8.4 Hz), 7.14 (tt, 2H, J=7.4 and 1.1 Hz), 6.02 (t, 2H, J=5.5 Hz), 3.43 (m, 4H), 1.59 (m, 4H), 1.32 (m, 12H), 0.89 (t, 6H, J=7.3 Hz). UV-vis spectrum: $\lambda_{max}$=446 nm (dichloromethane), 455 nm (PVB film). Fluorimetry: $\lambda_{max}$=611 nm (dichloromethane), 569 nm (PVB film).

Examples 56 and 57

Examples 56 and 57 are synthesized in a two step process.

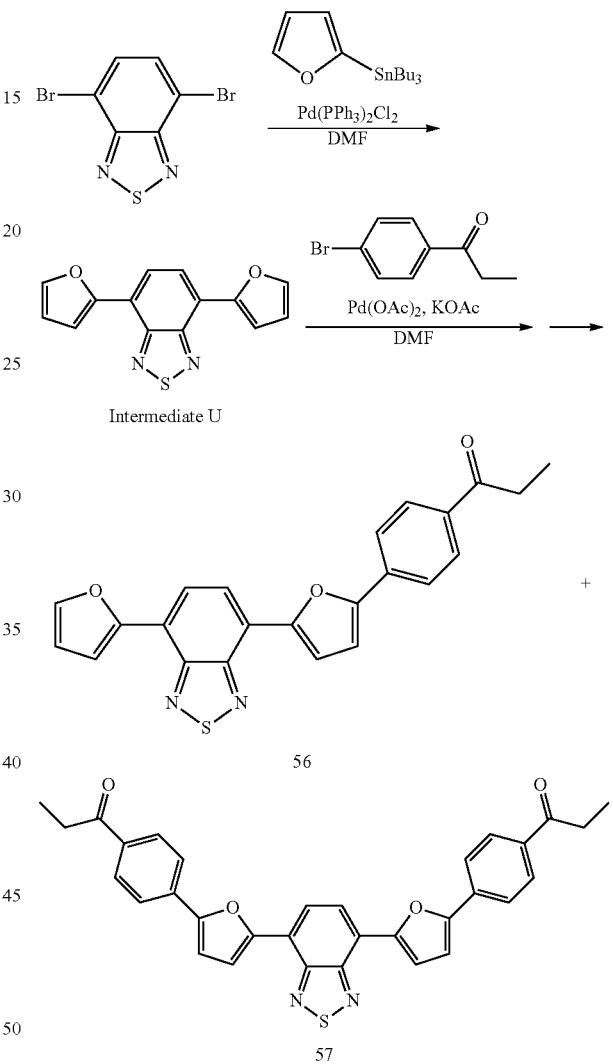

Step 1: Synthesis of Intermediate U

A solution of 4,7-dibromobenzothiadiazole (1.17 g, 4 mmol), 2-(tributylstannyl)furan (5 mL, 15.9 mmol), and bis(triphenylphosphine)palladium dichloride (0.70 g, 1.0 mmol) in anhydrous dimethylformamide (20 mL) was stirred under nitrogen and heated at 40° C. for 2 hours. The reaction mixture was poured into water (200 mL), stirred for 30 minutes and extracted with dichloromethane (2×200 mL). The extract was concentrated under reduced pressure, the residue was diluted with chlorobenzene (100 mL), and the volatiles were removed under high vacuum. The final residue was chromatographed using silica gel and hexane/dichloromethane 2:1) as an eluent. The obtained product was recrystallized from ethanol to give pure Intermediate U (0.84 g, 78%). $^1$H NMR (400 MHz, CDCl$_3$): δ 8.04 (s, 2H), 7.68 (dd, 2H, J=3.3 and 0.7 Hz), 7.58 (dd, 2H, J=1.8 and 0.7 Hz), 6.63 (dd, 2H, J=3.6 and 1.8 Hz).

Step 2: Synthesis of Examples 56 and 57

A solution of Intermediate U (500 mg, 1.86 mmol), ethyl 4-bromopropiophenone (846 mg, 4 mmol), potassium acetate (588 mg, 6 mmol), and palladium acetate (112 mg, 0.5 mmol) in dimethylformamide (10 mL) was stirred under argon and heated at 80° C. for 4 hours. The reaction mixture was poured into water (200 mL) and stirred for 30 minutes. The precipitate was filtered off, washed with methanol (20 mL) and dried in a vacuum oven. Column chromatography of this material using silica gel and hexane/dichloromethane/ethyl acetate (37:60:3) gave crude chromophore Example 56 as the first fraction. Recrystallization of this product from acetone gave pure Example 9, 79 mg (20% yield). $^1$H NMR (400 MHz, CDCl$_3$): δ 8.15 (d, 1H, J=7.6 Hz), 8.06 (d, 1H, J=7.6 Hz), 8.03 (d, 2H, J=8.7 Hz), 7.86 (d, 2H, J=8.7 Hz), 7.80 (d, 1H, J=3.6 Hz), 7.70 (d, 1H, J=3.3 Hz), 7.60 (d, 1H, J=1.1 Hz), 7.02 (d, 1H, J=3.7 Hz), 6.64 (dd, 1H, J=3.3 and 1.9 Hz), 3.03 (q, 2H, J=6.9 Hz), and 1.25 (t, 3H, J=7.4 Hz).

Recrystallized from acetone, the material from the second fraction gave chromophore Example 57, 45 mg (8% yield). 1H NMR (400 MHz, CDCl$_3$): 6808.19 (s, 2H), 8.04 (d, 4H, J=8.4 Hz), 7.87 (d, 4H, J=8.4 Hz), 7.82 (d, 2H, J=3.6 Hz), 7.03 (d, 2H, J=3.7 Hz), 3.03 (q, 4H, J=7.2 Hz), 1.26 (t, 6H, J=7.2 Hz).

Example 58

Example 58 is synthesized in a two step process.

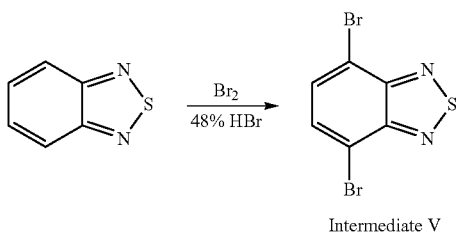

Step 1: Synthesis of Intermediate V

A mixture of benzothiadiazole (5.00 G, 36.7 mmol), 48% HBr (50 mL) and bromine (4.1 mL, 80 mmol) was stirred and heated at 120° C. under a reflux condenser for 16 hours. The hot reaction mixture was poured slowly into a mixture of crushed ice (1 kG) and sodium bicarbonate (0.2 kG) in a 4 L beaker, stirred for 1 hour and extracted with 20% THF in DCM (2×500 mL). The extract was dried over magnesium sulfate, and the solvent was removed under reduced pressure. The residue was triturated with hot ethanol (100 mL) and set aside at room temperature for 2 hours. The crystals were filtered off and dried to give 4,7-dibromobenzothiadiazole (9.65 G, 89% yield).

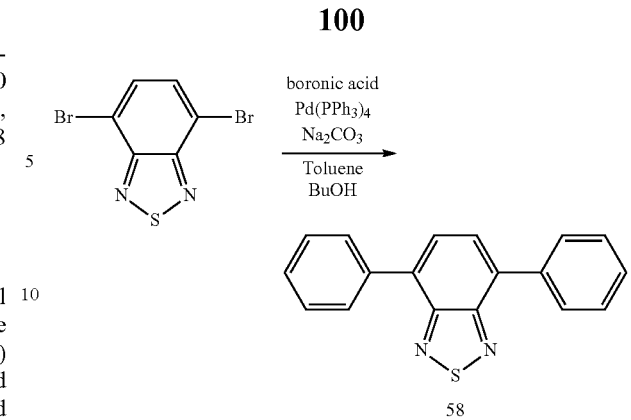

Step 2: Synthesis of Example 58

A mixture of 4,7-dibromobenzothiadiazole (1.47 G, 5 mmol), phenylboronic acid (1.22 g, 10 mmol), saturated aqueous solution of sodium carbonate (2.12 g, 20 mmol), palladium catalyst (0.50 g, 0.43 mmol) butanol (30 mL) and toluene (30 mL) was stirred under argon and heated at 100° C. for 16 hours. The reaction mixture was diluted with toluene (200 mL), poured into water (200 mL) and stirred for 30 minutes. The organic layer was separated, and the volatiles were removed under reduced pressure. The crude product was purified by column chromatography using silica gel and hexane/DCM (4:1→1:1). The obtained material was recrystallized from ethanol (100 mL) to give pure chromophore Example 58 (1.17 g, 81%).

Example 59

Example 59 is synthesized according to the following reaction scheme.

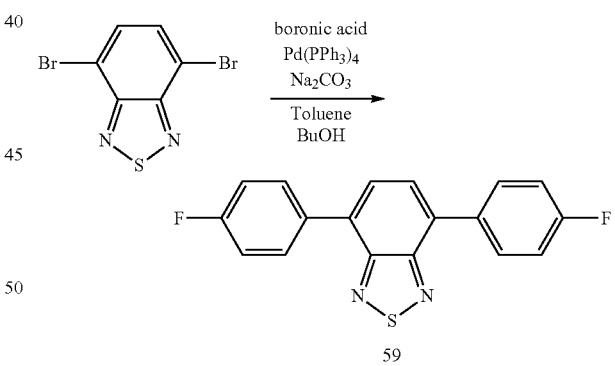

Using 4-fluorophenylboronic acid and applying a procedure analogous to the Example 58 procedure, chromophore Example 59 was obtained in 82% yield.

Luminescent Medium Examples

It has been discovered that the chromophore derivatives, as disclosed herein, can be combined with a polymer matrix to form an organic down-shifting luminescent medium, which when applied to the light incident surface or encapsulated into the photovoltaic device or solar cell during fabrication, can enhance the photoelectric conversion efficiency by greater than 0.2%, greater than 0.5%, greater than 1.0%, greater than 2.0%, greater than 5.0%, or greater than 10.0%. This results in a lower cost device, compared to devices which use an inorganic down-shifting medium, in which the device also meets the solar cell industry lifetime standard.

These benefits are further described by the following examples, which are intended to be illustrative of the embodiments of the disclosure, but are not intended to limit the scope or underlying principles in any way.

Luminescent Medium Example 1

Preparation of a Thin Film Organic Wavelength Conversion Luminescent Medium

The thin film organic wavelength conversion luminescent medium, which comprises an optically transparent polymer matrix material and at least one luminescent dye, was fabricated by (i) preparing a Polyvinyl butyral (PVB) polymer solution by dissolving a PVB powder (from Aldrich and used as received) in cyclopentanone (from Aldrich and used as received) at a predetermined ratio of 20 wt %; (ii) preparing a luminescent dye containing a PVB matrix by mixing the PVB polymer solution with the synthesized Example 6 compound at a weight ratio (Example 6 Compound/PVB) of 0.5:99.5 to obtain a dye-containing polymer solution; (iii) forming the dye/polymer thin film by directly casting the dye-containing polymer solution onto a glass substrate, then heat treating the substrate from room temperature up to 100° C. in 2 hours, completely removing the remaining solvent by further vacuum heating at 130° C. overnight; and (iv) peeling off the dye/polymer thin film under the water and then drying out the free-standing polymer film before use in the following experiments; (v) the film thickness was 250 m, which was obtained by varying the dye/polymer solution concentration and evaporation speed.

Measurement of the Efficiency Enhancement

The solar cell photoelectric conversion efficiency was measured by a Newport 300W full spectrum solar simulator system. The light intensity was adjusted to one sun (AM1.5G) by a 2×2 cm calibrated reference monocrystaline silicon solar cell. Then the I-V characterization of the CdS/CdTe solar cell was performed under the same irradiation and its efficiency is calculated by the Newport software program which is installed in the simulator. The CdS/CdTe solar cell used in this study has an efficiency ηcell of 11.3%, which is similar to the efficiency level achieved in most commercially available CdS/CdTe cells. After determining the stand alone efficiency of the cell, the Luminescent Medium Example 1 thin film organic wavelength conversion luminescent medium as manufactured above, which was cut to the same shape and size of the light incident active window of the CdS/CdTe cell, was attached to the light incident front glass substrate of the CdS/CdTe cell as illustrated in FIG. 1, using a refractive index matching liquid (n=1.500) fill in between the luminescent film and the light incident glass surface of the CdS/CdTe solar cell. The solar cell efficiency with the luminescent film ηcell+luminescent film was measured again under same one sun exposure. The efficiency enhancement of the CdS/CdTe solar cell due to the attached luminescent film was determined using the following equation:

Efficiency Enhancement=(ηcell+luminescent film−ηcell)/ηcell*100%

The efficiency enhancement for Luminescent Medium Example 1 was determined to be 6.0%.

Luminescent Medium Example 2

A thin film organic wavelength conversion luminescent medium was obtained in the same manner as in Luminescent Medium Example 1 except that the solar cell was a thin film CIGS cell with an efficiency ηcell of 14.0%, which was higher than the efficiency level achieved in various commercial CIGS cells. The efficiency enhancement for Luminescent Medium Example 2 was determined to be 6.7%.

Luminescent Medium Example 3

A thin film organic wavelength conversion luminescent medium was obtained in the same manner as in Luminescent Medium Example 1 except that the luminescent dye used was the Example 26 compound. The efficiency enhancement for Luminescent Medium Example 3 was determined to be 2.4%.

Luminescent Medium Example 4

A thin film organic wavelength conversion luminescent medium was obtained in the same manner as in Luminescent Medium Example 3 except that the solar cell was a thin film CIGS cell with an efficiency ηcell of 14.0%, which was higher than the efficiency level achieved in various commercial CIGS cells. The efficiency enhancement for Luminescent Medium Example 4 was determined to be 6.1%.

Luminescent Medium Example 5

A thin film organic wavelength conversion luminescent medium was obtained in the same manner as in Luminescent Medium Example 1 except that the luminescent dye used was the Example 28 compound. The efficiency enhancement for Luminescent Medium Example 5 was determined to be 12.2%.

Luminescent Medium Example 6

A thin film organic wavelength conversion luminescent medium was obtained in the same manner as in Luminescent Medium Example 5 except that the solar cell was a thin film CIGS cell with an efficiency $\eta_{cell}$ of 14.0%, which was higher than the efficiency level achieved in various commercial CIGS cells. The efficiency enhancement for Luminescent Medium Example 6 was determined to be 10.6%.

Luminescent Medium Example 7

A thin film organic wavelength conversion luminescent medium was obtained in the same manner as in Luminescent Medium Example 1 except that the luminescent dye used was the Example 33 compound, and the film was applied to a crystalline Silicon solar cell. The efficiency enhancement for Luminescent Medium Example 7 was determined to be 1.2%.

Luminescent Medium Example 8

A thin film organic wavelength conversion luminescent medium was obtained in the same manner as in Luminescent Medium Example 7 except that Example Compound 34 was used instead of Compound 33. The efficiency enhancement for Luminescent Medium Example 11 was determined to be 1.4%.

Luminescent Medium Example 9

A thin film organic wavelength conversion luminescent medium was obtained in the same manner as in Luminescent Medium Example 1 except that the luminescent dye used was the Example 42 compound, and the film was applied to a crystalline Silicon solar cell. The efficiency enhancement for Luminescent Medium Example 9 was determined to be 0.9%.

Luminescent Medium Example 10

A thin film organic wavelength conversion luminescent medium was obtained in the same manner as in Luminescent Medium Example 9 except that Example Compound 44 was used instead of Compound 42. The efficiency enhancement for Luminescent Medium Example 10 was determined to be 0.4%.

Luminescent Medium Example 11

A thin film organic wavelength conversion luminescent medium was obtained in the same manner as in Luminescent Medium Example 9 except that Example Compound 45 was used instead of Compound 42. The efficiency enhancement for Luminescent Medium Example 11 was determined to be 0.8%.

Luminescent Medium Example 12

A thin film organic wavelength conversion luminescent medium was obtained in the same manner as in Luminescent Medium Example 9 except that Example Compound 46 was used instead of Compound 42. The efficiency enhancement for Luminescent Medium Example 12 was determined to be 0.4%.

Luminescent Medium Example 13

A thin film organic wavelength conversion luminescent medium was obtained in the same manner as in Luminescent Medium Example 1 except that Example Compound 48 was used instead of Compound 1. The efficiency enhancement for Luminescent Medium Example 13 was determined to be 14.9%.

Luminescent Medium Example 14

A thin film organic wavelength conversion luminescent medium was obtained in the same manner as in Luminescent Medium Example 14 except that the solar cell was a thin film CIGS cell with an efficiency $\eta_{cell}$ of 14.0%, which was higher than the efficiency level achieved in various commercial CIGS cells. The efficiency enhancement for Luminescent Medium Example 14 was determined to be 11.6%.

Luminescent Medium Example 15

A thin film organic wavelength conversion luminescent medium was obtained in the same manner as in Luminescent Medium Example 13 except that the luminescent dye used was the Example 49 Compound. The efficiency enhancement for Luminescent Medium Example 15 was determined to be 15.0%.

Luminescent Medium Example 16

A thin film organic wavelength conversion luminescent medium was obtained in the same manner as in Luminescent Medium Example 15 except that the solar cell was a thin film CIGS cell with an efficiency $\eta_{cell}$ of 14.0%, which was higher than the efficiency level achieved in various commercial CIGS cells. The efficiency enhancement for Luminescent Medium Example 16 was determined to be 12.0%.

Luminescent Medium Example 17

A thin film organic wavelength conversion luminescent medium was obtained in the same manner as in Luminescent Medium Example 13 except that the luminescent dye used was the Example 52 Compound. The efficiency enhancement for Luminescent Medium Example 17 was determined to be 13.6%.

Luminescent Medium Example 18

A thin film organic wavelength conversion luminescent medium was obtained in the same manner as in Luminescent Medium Example 17 except that the solar cell was a thin film CIGS cell with an efficiency $\eta_{cell}$ of 14.0%, which was higher than the efficiency level achieved in various commercial CIGS cells. The efficiency enhancement for Luminescent Medium Example 18 was determined to be 7.3%.

Luminescent Medium Example 19

A thin film organic wavelength conversion luminescent medium was obtained in the same manner as in Luminescent Medium Example 13 except that the luminescent dye used was the Example 54 Compound. The efficiency enhancement for Luminescent Medium Example 19 was determined to be 15.2%.

Luminescent Medium Example 20

A thin film organic wavelength conversion luminescent medium was obtained in the same manner as in Luminescent Medium Example 19 except that the solar cell was a thin film CIGS cell with an efficiency $\eta_{cell}$ of 14.0%, which was higher than the efficiency level achieved in various commercial CIGS cells. The efficiency enhancement for Luminescent Medium Example 20 was determined to be 6.0%.

Luminescent Medium Example 21

A thin film organic wavelength conversion luminescent medium was obtained in the same manner as in Luminescent Medium Example 13 except that the luminescent dye used was the Example 55 Compound. The efficiency enhancement for Luminescent Medium Example 21 was determined to be 14.4%.

Luminescent Medium Example 22

A thin film organic wavelength conversion luminescent medium was obtained in the same manner as in Luminescent Medium Example 21 except that the solar cell was a thin film CIGS cell with an efficiency $\eta_{cell}$ of 14.0%, which was higher than the efficiency level achieved in various commercial CIGS cells. The efficiency enhancement for Luminescent Medium Example 22 was determined to be 6.6%.

Luminescent Medium Example 23

A thin film organic wavelength conversion luminescent medium was obtained in the same manner as in Luminescent Medium Example 1 except that the luminescent dye used was the Example 58 compound, and the film was applied to a crystalline Silicon solar cell. The efficiency enhancement for Luminescent Medium Example 23 was determined to be 0.9%.

Luminescent Medium Example 24

A thin film organic wavelength conversion luminescent medium was obtained in the same manner as in Luminescent Medium Example 1 except that the luminescent dye used was the Example 59 compound, and the film was applied to a crystalline Silicon solar cell. The efficiency enhancement for Luminescent Medium Example 24 was determined to be 0.9%.

Table 1 below shows the measured efficiency enhancement for each of the example luminescent mediums.

TABLE 1

Efficiency enhancement of example luminescent films.

| Luminescent Medium | Polymer Matrix | Luminescent Dye | Solar cells | Efficiency Enhancement |
|---|---|---|---|---|
| Medium 1 | PVB | Example Compound 6 | CdS/CdTe | 6% |
| Medium 2 | PVB | Example Compound 6 | CIGS | 6.7% |
| Medium 3 | PVB | Example Compound 26 | CdS/CdTe | 2.4% |
| Medium 4 | PVB | Example Compound 26 | CIGS | 6.1% |
| Medium 5 | PVB | Example Compound 28 | CdS/CdTe | 12.2% |
| Medium 6 | PVB | Example Compound 28 | CIGS | 10.6% |
| Medium 7 | PVB | Example Compound 33 | c-Silicon | 1.2% |
| Medium 8 | PVB | Example Compound 34 | c-Silicon | 1.4% |
| Medium 9 | PVB | Example Compound 42 | c-Silicon | 0.9% |
| Medium 10 | PVB | Example Compound 44 | c-Silicon | 0.4% |
| Medium 11 | PVB | Example Compound 45 | c-Silicon | 0.8% |
| Medium 12 | PVB | Example Compound 46 | c-Silicon | 0.4% |
| Medium 13 | PVB | Example Compound 48 | CdS/CdTe | 14.9% |
| Medium 14 | PVB | Example Compound 48 | CIGS | 11.6% |
| Medium 15 | PVB | Example Compound 49 | CdS/CdTe | 15.0% |
| Medium 16 | PVB | Example Compound 49 | CIGS | 12.0% |
| Medium 17 | PVB | Example Compound 52 | CdS/CdTe | 13.6% |
| Medium 18 | PVB | Example Compound 52 | CIGS | 7.3% |
| Medium 19 | PVB | Example Compound 54 | CdS/CdTe | 15.2% |
| Medium 20 | PVB | Example Compound 54 | CIGS | 6.0% |
| Medium 21 | PVB | Example Compound 55 | CdS/CdTe | 14.4% |
| Medium 22 | PVB | Example Compound 55 | CIGS | 6.6% |
| Medium 23 | PVB | Example Compound 58 | c-Silicon | 0.9% |
| Medium 24 | PVB | Example Compound 59 | c-Silicon | 0.9% |

As illustrated in Table 1, the solar photoelectric conversion efficiency of CdS/CdTe and CIGS solar cells is enhanced by applying the thin film organic wavelength conversion luminescent medium, as disclosed herein, to the solar cell. All prepared examples using the medium disclosed herein show an efficiency enhancement of greater than 0.4% for crystalline Silicon solar cells, and greater than 2% for CdS/CdTe and CIGS solar cells.

The solar photoelectric conversion efficiency of crystalline Silicon solar cells is enhanced by greater than 0.4% by applying the thin film organic wavelength conversion luminescent medium. Due to the high cost of Silicon solar cells, even small improvements in efficiency may provide a significant improvement in the price per watt of electricity generated by these devices. These results also illustrate that further optimization of the chromophore and film components of the medium disclosed herein, could potentially provide even greater efficiency enhancements of more than 1.0%, or more than 1.5%, or more than 2%, improvement, depending on the Silicon solar cell device that is used.

The solar photoelectric conversion efficiency of CdS/CdTe and CIGS solar cells is enhanced by greater than 2% by applying the thin film organic wavelength conversion luminescent medium to the solar cell. Mediums 5, 6, 13-17, 19, and 20 provided greater than 10% efficiency enhancement, with several of these mediums providing greater than 14% efficiency enhancement. These results also illustrate that further optimization of the chromophore and film components of the medium disclosed herein, could potentially provide even greater efficiency enhancements for the CdS/CdTe and CIGS solar cells of more than 20%, or more than 25%, improvement, depending on the photovoltaic device that is used.

Although the foregoing description has shown, described, and pointed out the fundamental novel features of the present teachings, it will be understood that various omissions, substitutions, and changes in the form of the detail of the invention as illustrated, as well as the uses thereof, may be made by those skilled in the art, without departing from the scope of the present teachings. Consequently, the scope of the present teachings should not be limited to the foregoing discussion, but should be defined by the appended claims. All patents, patent publications and other documents referred to herein are hereby incorporated by reference in their entirety.

What is claimed is:

1. A chromophore represented by formula I-a:

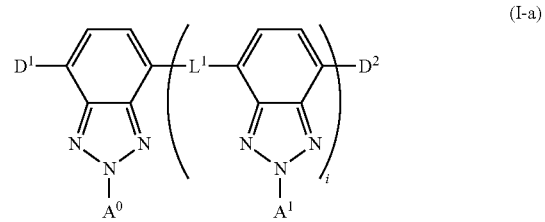

(I-a)

wherein:

i is 0;

$A^0$ is alkyl optionally substituted by a moiety selected from the group consisting of —NRR", —OR, —COOR, —COR, —CONHR, —CONRR", and —CN; wherein R is $C_1$-$C_{20}$ alkyl, and R" is hydrogen or $C_1$-$C_{20}$ alkyl; and $D^1$ and $D^2$ are each optionally substituted aryl, wherein the optionally substituted aryl group is independently selected from the group consisting of optionally substituted phenyl, optionally substituted naphthyl, optionally substituted phenanthrenyl, optionally substituted naphthacenyl, optionally substituted anthracenyl, and optionally substituted perylenyl.

2. The chromophore of claim 1, wherein $A^0$ is an optionally substituted $C_{1-8}$ alkyl.

3. The chromophore of claim 1, wherein the substituent for optionally substituted aryl, optionally substituted phenanthrenyl, optionally substituted naphthacenyl, optionally substituted anthracenyl, or optionally substituted perylenyl is selected from the group consisting of alkoxy, aryloxy, aryl, heteroaryl, and amino.

4. The chromophore of claim 1, wherein $D^1$ and $D^2$ are each independently phenyl optionally substituted by alkoxy or amino.

5. The chromophore of claim 1, further represented by formula (III-a):

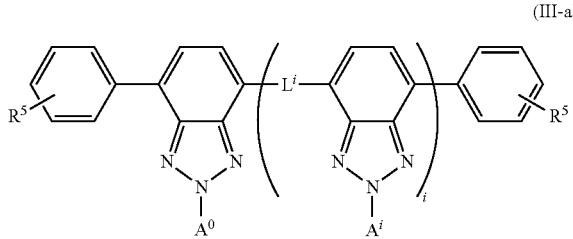

wherein:
each $R^5$ is independently selected from the group consisting of alkyl, optionally substituted alkoxy, optionally substituted aryloxy, optionally substituted acyloxy, and amino.

6. A chromophore represented by formula (III-a):

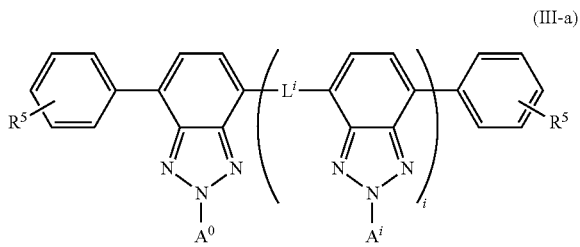

wherein:
each R5 is independently selected from the group consisting of alkyl, optionally substituted alkoxy, optionally substituted aryloxy, optionally substituted acyloxy, and amino;
$A^0$ is $C_1$-$C_{40}$ alkyl or $C_1$-$C_{20}$ haloalkyl; and
i is 0.

7. A wavelength conversion luminescent medium comprising an optically transparent polymer matrix and at least one luminescent dye comprising a chromophore of claim 1.

8. The wavelength conversion luminescent medium of claim 7, wherein the polymer matrix comprises a substance selected from the group consisting of polyethylene terephthalate, polymethyl methacrylate, polyvinyl butyral, ethylene vinyl acetate, ethylene tetrafluoroethylene, polyimide, amorphous polycarbonate, polystyrene, siloxane sol-gel, polyurethane, polyacrylate, and combinations thereof.

9. The wavelength conversion luminescent medium of claim 7, wherein the refractive index of the polymer matrix material is in the range of about 1.4 to about 1.7.

10. The wavelength conversion luminescent medium of claim 7, wherein the luminescent dye is present in the polymer matrix in an amount in the range of about 0.01 wt % to about 3 wt %.

11. A photovoltaic module comprising at least one photovoltaic device or solar cell, and a wavelength conversion luminescent medium according to claim 7, wherein the wavelength conversion luminescent medium is positioned such that the incident light passes through the wavelength conversion luminescent medium prior to reaching the photovoltaic device or solar cell.

12. The photovoltaic module of claim 11, wherein the wavelength conversion luminescent medium is a film having a thickness in the range of about 0.1 m to about 1 mm.

13. The photovoltaic module of claim 11, wherein the photovoltaic device or solar cell comprises at least one device selected from the group consisting of a Cadmium Sulfide/Cadmium Telluride solar cell, a Copper Indium Gallium Diselenide solar cell, an amorphous Silicon solar cell, a microcrystalline Silicon solar cell, or a crystalline Silicon solar cell.

14. The photovoltaic module of claim 11, further comprising a refractive index matching liquid or optical adhesive that is used to attach the wavelength conversion luminescent medium to a light incident surface of the photovoltaic device or solar cell.

15. The chromophore of claim 1, represented by formula:

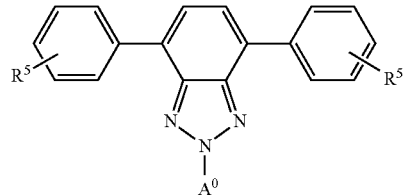

wherein:
$A^0$ is $C_1$-$C_8$ alkyl; and
each $R^5$ is independently selected from the group consisting of alkyl and alkoxy.

* * * * *